US006632636B1

(12) United States Patent
Lagace et al.

(10) Patent No.: US 6,632,636 B1
(45) Date of Patent: Oct. 14, 2003

(54) **NUCLEIC ACIDS ENCODING 3-KETOACYL-ACP REDUCTASE FROM *MORAXELLA CATARRAHALIS***

(75) Inventors: Robert E. Lagace, Belmont, CA (US); Chandra Patterson, Menlo Park, CA (US); Kim L. Berg, Palo Alto, CA (US)

(73) Assignee: Elitra Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 09/596,002

(22) Filed: Jun. 16, 2000

Related U.S. Application Data
(60) Provisional application No. 60/140,121, filed on Jun. 18, 1999.

(51) Int. Cl.$^7$ .................. C12P 21/06; C12N 15/00; C12N 5/00; C12N 1/20; C07H 21/04
(52) U.S. Cl. .................. 435/69.1; 435/70.1; 435/71.1; 435/189; 435/252.3; 435/254.11; 435/320.1; 435/325; 435/440; 536/23.2; 536/24.32
(58) Field of Search .................. 435/69.1, 69.3, 435/69.7, 70.1, 71.1, 71.2, 320.1, 325, 183, 440, 455, 189, 252.3, 254.11, 257.2; 536/23.2, 23.7; 534/24.32

(56) References Cited

U.S. PATENT DOCUMENTS

| | | | |
|---|---|---|---|
| 5,474,796 A | 12/1995 | Brennan | |
| 5,605,662 A | 2/1997 | Heller et al. | |
| 5,830,721 A | 11/1998 | Stemmer et al. | |
| 5,876,946 A | 3/1999 | Burbaum et al. | |
| 6,110,704 A | 8/2000 | Huang et al. | |
| 6,348,328 B1 | * 2/2002 | Black et al. | |

OTHER PUBLICATIONS

Kennell, D.E. Prog. Nucl. Acid Res. Mol. Biol. 11:259–301, 1971.*
Bhushan R. et al., Molecular Cloning and Characterization of Outer Membrane Protein E of Moraxella (Branhamella) catarrhalis, (1994) Journal of Bacteriology, vol. 176, No. 21, pp. 6636–6643.
Helminen, M. E. et al., A Large Antigenically Conserved Protein on the Surface of *Moraxella catarrhalis* Is a Target for Protective Antibodies, (1994) Journal of Infectious Disease, 170:867–872.
Athauda, et al. 1993. Entrapment and inhibition of human immunodeficiency virus proteinase by $\alpha_2$–macroglobulin and structural changes in the inhibitor. *J. Biochem.*, 113:742–746.
Blattner, et al. 1993. Analysis of the *Escherichia coli* genome. IV. DNA sequence of the region from 89.2 to 92.8 minutes. *Nucleic Acids Research*, 21(23):5408–5417.
Braxton, et al. 1992. Incorporation of a stabilizing $Ca^{2+}$–binding loop into subtilisin BPN'. *Biochemistry*, 31:7796–7801.

Bult, et al. 1996. Complete genome sequence of the methanogenic archaeon, *Methanococcus jannaschii*, *Science*. 273:1058, 1067–1073.
Cote, et al. 1983. Generation of human monoclonal antibodies reactive with cellular antigens. *Proc. Natl. Acad. Sci. USA*, 80:2026–2030.
Fleischmann, et al. 1995. Whole–genome random sequencing and assembly of Haemophilus influenzae Rd. *Science*, 269:496–498, 507–512.
Fraser, et al. 1995. The minimal gene complement of *Mycoplasma genitalium*. *Science*. 270:397–403.
Gee, et al. 1994. Potential therapeutic usefulness of intermolecular triplex DNA. in Huber, B. E. (Ed.). Cancer Therapy in the Twenty–First Century, vol. I: Molecular & Immunologic Approaches, pp. 163–177. Mount Kisco: Futura Publishing Co., Inc.
Gordon, et al. 1998. *Consed*: A graphical tool for sequence finishing. *Genome Research*, 8:195–202.
Heller, et al. 1997. Discovery and analysis of inflammatory disease–related genes using cDNA microarrays. *Proc. Natl. Acad. Sci. USA*, 94:2150–2155.
Hensel, et al. 1995. Simultaneous identification of bacterial virulence genes by negative selection. *Science*, 269:400–403.
Huse, et al. 1989. Generation of a large combinatorial library of the immunoglobulin repertoire in Phage Lambda. *Science*, 246:1275–1281.
Kozbor, et al. 1985. Specific immunoglobulin production and enhanced tumorigenicity following ascites growth of human hybridomes. *Journal of Immunological Methods*, 81:31–42.
Lander, et al. 1988. Genomic mapping by fingerprinting random clones: A mathematical analysis. *Genomics*, 2:231–239.
Mahan, et al. 1993. Selection of bacterial virulence genes that are specifically induced in host tissues. *Science*, 259:686–688.
Sanger, et al. 1975. A rapid method for determining sequences in DNA by primed synthesis with DNA polymerase. *J. Mol. Biol.*, 94:441–448.

(List continued on next page.)

*Primary Examiner*—Patricia A. Duffy
(74) *Attorney, Agent, or Firm*—Knobbe, Martens, Olson & Bear, LLP

(57) ABSTRACT

The present invention provides the genomic sequences of a library of purified nucleic acid molecules, or their complements, comprising the genome of *Moraxella catarrhalis*. The invention also provides the identification of open reading frames contained within the nucleic acid molecules of the library. The present invention further provides for the use of the nucleic acid molecules, their complements or fragments, and proteins or portions thereof for identifying ligands and useful diagnostic and therapeutic compositions. In addition the invention provides for vectors, host cells and methods for producing *M. catarrhalis* proteins or portions thereof.

14 Claims, No Drawings

OTHER PUBLICATIONS

Schena, et al., 1996. Parallel human genome analysis: Microarray–based expression monitoring of 1000 genes. *Proc. Natl. Acad. Sci. USA*, 93:10614–10619.

Kohler, et al. 1975. Continuous cultures of fused cells secreting antibody of predefined specificity. *Nature*, 256:495–497.

* cited by examiner

NUCLEIC ACIDS ENCODING 3-KETOACYL-ACP REDUCTASE FROM *MORAXELLA CATARRHALIS*

CROSS-REFERENCE TO RELATED APPLICATION

This application claims priority under 35 U.S.C.§119(e) to U. S. Provisional Application Serial No. 60/140,121, filed Jun. 18, 1999.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF INVENTION

The present invention discloses nucleotide sequences from the genome of *Moraxella catarrhalis*. These sequences may be used in various assays and in the development of diagnostic and therapeutic agents.

BACKGROUND OF INVENTION

All animals coexist with an indigenous microflora. Beginning shortly after birth, the gastrointestinal tract, lungs, and other areas of the human body are colonized by different bacterial species. A large number of factors operate to maintain symbiotic, host-microbe balance. These include the physical barriers of skin and mucosal surfaces and both nonspecific and highly specific aspects of the immune system. When host-microbe balance becomes disturbed, infection may ensue. Virulence, the ability of a microbe to produce infection, is related to a variety of complex mechanisms of disease induction. Some organisms are highly virulent and cause clinical illness when they colonize most or all hosts. Alternatively, when host defenses are compromised, normally symbiotic microbes can induce serious, or even life-threatening, infections. Thus, infection is generally a consequence of the interaction between a relatively virulent microbe and a normal host or between a relatively less virulent microbe and a host with some degree of transient or permanent immunological impairment.

*M. catarrhalis (Branhamella catarrhalis)* is a large, aerobic, gram-negative diplococcus normally found among the bacterial flora of human upper airways. It is nonmotile and possesses fimbriae. Collonies are regularly friable and nonadherent and grow well on blood or chocolate agar. Unlike many other pathogenic bacteria, *M. catarrhalis* shows a high degree of homogeneity in its outer membrane proteins. This usually harmless parasite of the mucous membranes may behave as an opportunistic pathogen when microbe-host balance is perturbed. Following infection, host antibodies directed against one or more of the microbial outer-membrane proteins are detectable-in the serum.

*M. catarrhalis* is known to cause acute, localized infections such as otitis media, sinusitis, and bronchopulmonary infection and life-threatening, systemic diseases including endocarditis and meningitis. The presence of bacterial endotoxin and host histamine and chemotactic factors are major indicators of *M. catarrhalis* pathogenicity.

*M. catarrhalis* can be isolated from the upper respiratory tract of 50% of healthy school children and 7% of healthy adults. In children with otitis media, colonization increases to 86%, and it is the third most common bacterial isolate. It causes 10–15% of otitis media and sinusitis. Infections of the maxillary sinuses, middle ears, or bronchi may occur through contiguous spread of the microbes. *M. catarrhalis* causes a large proportion of lower respiratory tract infections in elderly patients with chronic obstructive pulmonary diseases and is exceeded only by *Haemophilus influenzae* and *Streptococcus pneumoniae* as a causative agent of acute purulent exacerbations of chronic bronchitis.

Pneumonia due to *M. catarrhalis*, like that of *H. influenzae* or *S. pneumoniae*, begins with aspiration of the bacteria. Failure or absence of appropriate host defense allows the bacteria to replicate and produce an inflammatory response in the alveoli. Because of mandatory immunosuppression, organ transplant recipients can develop moderate to severe *M. catarrhalis* pneumonia very rapidly. Bloodstream invasion is less characteristic of *M. catarrhalis* than pneumococcal infection, but nearly 50% of *M. catarrhalis* pneumonia patients die within 3 months of onset.

*M. catarrhalis* is treated with antibiotic agents including penicillin-clavulanic acid combinations, cephalosporins, tetracycline, erythromycin, chloramphenicol, trimethoprim-sulfamethoxazole, and quinolones. Over 85% of *M. catarrhalis* clinical isolates have been reported to be resistant to penicillin. Moreover, the microbe protects itself by binding to the first subcomponent of the complement system (C1q) which inactivates the C1 complex or by inactivating the terminal, lytic complement complex via a protein on the outer cell wall surface. Resistance is mediated by two closely related β-lactamases, BRO-1, present in 90% of resistant isolates and BRO-2, present in 10%. These enzymes are active against penicillin, ampicillin, and amoxicillin, less active against cephalosporins, and bind avidly to clavulanic acid and sublactam. Tetracycline resistant strains are increasing in Europe and Asia and have been documented in the United States. Ampicillin, which had been universally effective in treating *M. catarrhalis* pneumonia, can no longer be used.

*M. catarrhalis* physiology and pathogenicity are reviewed in: Holt et al. (1994) *Bergey's Manual of Determinative Bacteriology*, Williams and Wilkins, Baltimore Md.; Cullmann (1997) Med Klin 92(3):162–166; Isselbacher et al. (1994) *Harrison's Principles of Internal Medicine*, McGraw-Hill, New York N.Y.; Murray (1995) *Manual of Clinical Microbiology*, ASM Press, Washington D.C.; and Shulman et al. (1997) *The Biologic and Clinical Basis of Infectious Diseases*, W B Saunders, Philadelphia Pa.

In view of the conditions or diseases associated with *M. catarrhalis*, it would be advantageous to provide specific methods for the diagnosis, prevention, and treatment of diseases attributed to *M. catarrhalis*. Relevant methods would be based on the expression of *M. catarrhalis*-derived nucleic acid sequences. Such traits as virulence, acquisition of resistance factors, and effects of treatment using particular therapeutic agents may be characterized by under- or over-expression of nucleic acid sequences as revealed using PCR, hybridization or microarray technologies. Treatment for diseases attributed to *M. catarrhalis* can then be based on expression of these identified sequences or their expressed proteins, and efficacy of any particular therapy and development of resistance monitored. The information provided herein provides the basis for understanding the pathogenicity of *M. catarrhalis* and treating and monitoring the treatment of diseases caused by *M. catarrhalis*.

SUMMARY OF THE INVENTION

The present invention relates to a genomic library comprising the combination of nucleic acid molecules from

*Moraxella catarrhalis*, presented as SEQ ID NOs: 1–41. The library substantially provides the nucleic acid molecules comprising the genome of *M. catarrhalis*, and the nucleic acid molecules provide a plurality of open reading frames (ORFs). The ORFs uniquely identify structural, functional, and regulatory genes of *M. catarrhalis*. The invention encompasses oligonucleotides, fragments, and derivatives of the *M. catarrhalis* nucleic acid molecules, and sequences complementary to the nucleic acid molecules listed in the Sequence Listing.

*M. catarrhalis* nucleic acid molecules, fragments, derivatives, oligonucleotides, and complementary sequences thereof, can be used as probes to detect, amplify, or quantify *M. catarrhalis* genes, ORFs, cDNAs, or RNAs in biological, solution or substrate-based, assays or as compositions in diagnostic kits. The invention contemplates the use of such diagnostic probes to identify the presence of *M. catarrhalis* sequence in a sample or to screen for virulence factors and mutations.

The invention also provides for the comparison of the *M. catarrhalis* genomic library or the encoded proteins with genomes, individual DNA sequences, or proteins from other *Moraxella* species or strains, other bacteria, and other organisms to identify virulence factors, regulatory elements, drug targets, and to characterize genomic organization. In another aspect, the present invention provides for the use of computer databases to make such comparisons.

The invention further provides host cells and expression vectors comprising nucleic acid molecules of the invention and methods for the production of the proteins they encode. Such methods include culturing the host cells under conditions for expression of *M. catarrhalis* protein and recovering the protein from cell culture. The invention still further provides purified *M. catarrhalis* protein of which at least a portion is encoded by a nucleic acid molecule selected from the nucleic acid molecules of the Sequence Listing.

The subject invention provides a method of screening a library or a plurality of molecules or compounds for specific binding to a *M. catarrhalis* nucleic acid molecule or fragment thereof or protein or portion thereof, to identify at least one ligand which specifically binds the *M. catarrhalis* nucleic acid molecule or protein. Such a method comprises the steps of combining the *M. catarrhalis* nucleic acid molecule or protein with a library or a plurality of molecules or compounds under conditions to allow specific binding and detecting *M. catarrhalis* nucleic acid molecule or protein bound to at least one molecule or compound, thereby identifying a ligand which specifically binds the nucleic acid molecule or protein. Suitable libraries of ligands comprise aptamers, DNA molecules, RNA molecules, peptide nucleic acids, peptides, mimetics, proteins, agonists, antagonists, antibodies, inhibitors, immunoglobulins, pharmaceutical agents, and drug compounds.

The subject invention also provides a method of purifying a ligand from a sample. Such a method comprises the steps of combining the *M. catarrhalis* nucleic acid molecule or protein with a library or a plurality of molecules or compounds under conditions to allow specific binding, detecting *M. catarrhalis* nucleic acid molecule or protein bound to at least one molecule or compound, recovering the bound *M. catarrhalis* nucleic acid molecule or protein and separating the bound *M. catarrhalis* nucleic acid molecule or protein from the ligand, thereby obtaining purified ligand.

The invention further comprises an antibody specific for a purified *M. catarrhalis* protein or a portion thereof which is encoded by an *M. catarrhalis* nucleic acid molecule selected from the Sequence Listing. Antibodies produced against *M. catarrhalis* protein may be used diagnostically for the detection of *M. catarrhalis* proteins in biological, solution- or substrate-based, samples and therapeutically to neutralize the activity of an *M. catarrhalis* protein expressed during infections caused by *M. catarrhalis*.

DESCRIPTION OF THE SEQUENCE LISTING AND TABLES

The Sequence Listing is a compilation of the consensus sequences of contiguous sequences (contigs) or groups of overlapping sequences, assembled from individual sequences obtained by sequencing genomic clone inserts of a randomly generated *M. catarrhalis* DNA library. Each assembled contig or singlet is identified by a sequence identification number (SEQ ID NO) and by the contig number which it represents.

Table 1 lists the assembled *M. catarrhalis* contiguous sequences prepared as described in the Examples. The first column contains the number of the contig, which is also SEQ ID NO, listed in ascending order. The second column contains the length of the nucleic acid molecule. The third and fourth columns contain the start and stop nucleotides, respectively, for any open reading frames (ORFs) in the contig. The fifth column contains the Locus ID. The sixth column lists the GenBank identification number of the closest homolog, if any. The seventh column gives the P-value for the match to the homolog. The last column contains the description of the homolog. Orphans or LURs have no GenBank homologs.

Table 2 shows the order of the contigs or singlets comprising the *M. catarrhalis* genome.

DESCRIPTION OF THE PREFERRED EMBODIMENTS

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

All patents and publications cited for the purpose of describing and disclosing the cell lines, protocols, reagents and vectors which might be used in connection with the invention are expressly incorporated by reference. Citation is for the purpose of providing the best description of the invention and is not to be construed as an admission that the invention is not entitled to antedate such disclosure.

Definitions

"Biologically active" refers to a protein having structural, immunological, regulatory, or chemical functions of a naturally occurring, recombinant, or synthetic molecule.

"Complementary" refer to the natural hydrogen bonding by base pairing between purines and pyrimidines. For example, the sequence A-C-G-T forms hydrogen bonds with its complements T-G-C-A or U-G-C-A. The degree of complementarity between nucleic acid strands affects the efficiency and strength of the hybridization and amplification reactions.

"Derivative" refers to the chemical modification of a nucleic acid or amino acid molecule. Chemical modifications can include replacement of hydrogen by an alkyl, acyl, or amino group or glycosylation, pegylation, or any similar process which retains or enhances biological activity, stability, or lifespan of the molecule.

"Fragment" refers to an Incyte clone or any part of a nucleic acid molecule which retains a usable, functional characteristic. Useful fragments include oligonucleotides which may be used in hybridization or amplification technologies or to regulate replication, transcription or translation.

"Hybridization complex" refers to a complex between two nucleic acid molecules by virtue of the formation of hydrogen bonds between purines and pyrimidines.

"Ligand" refers to any molecule or compound which will bind to a complementary site on a nucleic acid molecule or protein.

"Modulates" refers to a change in activity (biological, chemical, or immunological) or lifespan resulting from specific binding between a molecule or compound and either a nucleic acid molecule or a protein.

"Molecules" is used substantially interchangeably with the terms agents and compounds. Such molecules modulate the activity of nucleic acid molecules or proteins of the invention and may be composed of at least one of the following: inorganic and organic substances including cofactors, nucleic acids, proteins, carbohydrates, fats, and lipids.

"Nucleic acid molecule" is substantially interchangeable with the term polynucleotide and may refer to a probe, a fragment of DNA or RNA of genomic or synthetic origin. Such molecules may be double-stranded or single-stranded and may be engineered into vectors to perform a particular activity such as transcription.

"Oligonucleotide" is substantially equivalent to the terms "amplimer", "primer", "oligomer", and "element", and is preferably single stranded.

"Protein" refers to an amino acid sequence, oligopeptide, peptide, polypeptide or portions thereof whether naturally occurring or synthetic.

"Portion" refers to any part of a protein used for any purpose, but especially for the screening of a library of molecules or compounds which specifically bind to that portion or for the production of antibodies.

"Sample" is used in its broadest sense. A sample containing nucleic acid molecules may comprise a bodily fluid; an extract from a cell, chromosome, organelle, or membrane isolated from a cell; genomic DNA, RNA, or cDNA in solution or bound to a substrate; a cell; a tissue; a tissue print; a hair, and the like.

"Substantially purified" refers to nucleic acid molecules or proteins that are isolated or separated from their natural environment and are about 60% free to about 90% free from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

THE INVENTION

The majority of the *Moraxella catarrhalis* genome was sequenced using a strategy of shotgun sequencing. Genomic DNA was mechanically sheared, treated with enzyme to create blunt ends, gel-purified, and cloned into modified PBLUESCRIPT vectors (Stratagene, La Jolla Calif.). The vectors were transformed into *E. coli* cells and grown overnight. Colonies were picked, and plasmid DNA was isolated. Templates were prepared and sequenced, sequences were assembled into contiguous sequences (contigs), and open reading frames were identified.

The invention relates to a *Moraxella catarrhalis* genomic DNA library comprising a combination of nucleic acid molecules, SEQ ID NOs: 141, and their complements. These nucleic acid molecules comprise contiguous sequences which contain annotated and unannotated reading frames (ORFs and LURs). The nucleic acid molecules or fragments and probes thereof are used in hybridization, screening, and purification assays to identify ligands and in vectors and host cells to produce the proteins which they encode. The proteins or portions thereof are also used in screening and purification assays to identify useful ligands or to produce antibodies. The molecules or compounds used in hybridization, screening, and purification assays include aptamers, DNA molecules, RNA molecules, peptide nucleic acids, peptides, mimetics, transcription factor, enhancers, repressors, regulatory proteins, agonists, antagonists, antibodies, inhibitors, immunoglobulins, pharmaceutical agents, drug compounds, and the like. The nucleic acid molecules and proteins of *M. catarrhalis* are compared with those of other organisms using computer algorithms and databases to select those nucleic acid molecules and proteins of potential diagnostic and therapeutic use.

Characterization and Use of the Invention

Sequencing

Methods for sequencing nucleic acid molecules are well known in the art and may be used to practice any of the embodiments of the invention. These methods employ enzymes such as the Klenow fragment of DNA polymerase I, SEQUENASE, Taq DNA polymerase, thermostable T7 DNA polymerase (Amersham Pharmacia Biotech (APB), Piscataway N.J.), or combinations of polymerases and proofreading exonucleases such as those found in the ELONGASE amplification system (Life Technologies, Rockville Md.). Preferably, sequence preparation is automated with machines such as the HYDRA microdispenser (Robbins Scientific, Sunnyvale Calif.), MICROLAB 2200 system (Hamilton, Reno Nev.), and the DNA ENGINE thermal cycler (MJ Research, Watertown Mass.). Machines used for sequencing include the ABI 3700, 377 or 373 DNA sequencing systems (PE Biosystems, Foster City Calif.), the MEGABACE 1000 DNA sequencing system (APB), and the like. The sequences may be analyzed using a variety of algorithms which are well known in the art and described in Ausubel (1997; *Short Protocols in Molecular Biology*, John Wiley & Sons, New York N.Y., unit 7.7) and in Meyers (1995; *Molecular Biology and Biotechnology*, Wiley VCH, New York N.Y., pp. 856–853).

Shotgun sequencing methods are well known in the art and use thermostable DNA polymerases and heat-labile DNA polymerases. A detailed procedure is provided in the Examples. Prefinished sequences (incomplete assembled sequences) are cross-compared for identity using various algorithms or programs such as CONSED (Gordon (1998) Genome Res. 8:195–202), GELVIEW Fragment Assembly system (Genetics Computer Group, Madison Wiss., and PHRAP (Phil Green, University of Washington, Seattle Wash.). Contaminating sequences, including vector or chimeric sequences, can be masked, removed or restored, in the process of turning the prefinished sequences into finished sequences.

Extension of a Nucleic Acid Sequence

The sequences of the invention may be extended using various PCR-based methods known in the art. For example, the XL-PCR kit (PE Biosystems), nested primers, and commercially available cDNA or genomic DNA libraries (Life Technologies and Clontech (Palo Alto Calif.), respectively) may be used to extend the nucleic acid sequence. For all PCR-based methods, primers may be designed using commercially available software, such as OLIGO 4.06 software (National Biosciences, Plymouth Minn.) to be about 22 to 30 nucleotides in length, to have a GC content from about 40–45%, and to anneal to a target molecule at temperatures from about 55 C to about 68 C. When extending a sequence to recover untranslated, regulatory elements, it is preferable to use genomic, rather than cDNA libraries.

Use of *M. Catarrhalis* Nucleic Acid Molecules
Hybridization

The *M. catarrhalis* nucleic acid molecules and fragments thereof can be used in various hybridization technologies for various purposes. Hybridization probes may be designed or derived from a highly unique region such as the 5' untranslated sequence preceding the initiation codon or from a conserved coding region encoding a specific protein signature or motif and used in protocols to identify naturally occurring molecules encoding a particular *M. catarrhalis* protein, allelic variants, or related molecules. The probe should preferably have at least 50% sequence identity to any naturally occurring nucleic acid sequences. The probe may be a single stranded DNA or RNA molecule, produced biologically or synthetically, and labeled using oligolabeling, nick translation, end-labeling, or PCR amplification in the presence of at least one labeled nucleotide. A vector containing the nucleic acid molecule or a fragment thereof may be used to produce an mRNA probe in vitro by addition of an RNA polymerase and labeled nucleotides. These procedures may be conducted using commercially available kits such as those provided by APB.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60 C, which permits the formation of a hybridization complex between nucleic acid sequences that contain some mismatches. Subsequent washes are performed at increased stringency with buffers such as 0.2×SSC with 0.1% SDS at either 45 C (medium stringency) or 68 C (high stringency). At high stringency, hybridization complexes will remain stable only where the nucleic acid molecules are completely complementary. In some membrane-based hybridizations, 35–50% formamide can be added to the hybridization solution to reduce the temperature at which hybridization is performed. Background signals can be reduced by the use of other detergents such as Sarkosyl or TRITON X-100 (Sigma-Aldrich, St. Louis Mo.) and a blocking agent such as denatured salmon sperm DNA. Selection of components and conditions for hybridization are well known to those skilled in the art and are reviewed in Ausubel (supra) and in Sambrook et al. (1989; *Molecular Cloning, A Laboratory Manual*, Cold Spring Harbor Press, Plainview N.Y.).

Microarrays may be prepared and analyzed using methods known in the art. Oligonucleotides or fragments of a nucleic acid molecule may be used as either probes or targets. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents used to treat the condition, disease, or disorder. (See, eg, Brennan et al. (1995) U.S. Pat. No. 5,474,796; Schena et al. (1996) Proc Natl Acad Sci 93:10614–10619; Baldeschweiler et al. (1995) PCT application WO95/251116; Shalon et al. (1995) PCT application WO95/35505; Heller et al. (1997) Proc Natl Acad Sci 94:2150–2155; and Heller et al. (1997) U.S. Pat. No. 5,605,662.)

Hybridization probes are also useful in mapping the naturally occurring genomic sequence. The probes may be hybridized to: 1) a particular chromosome, 2) a specific region of a chromosome, 3) an artificial chromosome constructions such as human artificial chromosomes (HACs), yeast artificial chromosomes (YACs), bacterial artificial chromosomes (BACs), bacterial P1 constructions, single chromosomes from eukaryotic species, or 5) DNA libraries made from any of these sources.

Expression

A nucleic acid molecule encoding a *M. catarrhalis* protein may be cloned into a vector and used to express the protein or portions thereof in host cells. The nucleic acid sequence can be engineered by such methods as DNA shuffling (U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated sequence) from various sources which have been selected for their efficiency in a particular host. The vector, nucleic acid molecule, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel, supra, unit 16).

Routine cloning, subcloning, and propagation of nucleic acid molecules can be achieved using the multifunctional PBLUESCRIPT vector (Stratagene) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant *M. catarrhalis* proteins, the vector can be stably transformed into competent cells of *E. coli* along with a selectable or visible marker gene on the same or on a separate vector. After transformation, cells are allowed to grow in enriched media containing a selective agent. Selectable markers, antimetabolite, antibiotic, or herbicide resistance genes confer resistance to the respective selective agent and allow growth and recovery of cells which successfully express the introduced sequences. Resistant clones or colonies, identified either by survival on selective media or by the expression of visible markers, such as anthocyanins, green fluorescent protein (GFP), βglucuronidase, luciferase and the like, may be propagated using culture techniques well known in the art. Visible markers are also used to quantify the amount of protein expressed by the introduced genes. Verification that the host cell contains the desired *M. catarrhalis* nucleic acid molecule is based on DNA-DNA or DNA-RNA hybridizations or PCR amplification.

The host cell may be chosen for its ability to modify a recombinant protein in a desired fashion. Such modifications include acetylation, carboxylation, glycosylation, phosphorylation, lipidation, acylation, and the like. Post-translational processing sequences ("prepro" forms) may also be engineered into the recombinant nucleotide sequence in order to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), calmodulin binding peptide (CBP), 6×His, FLAG, MYC, and the like. GST, CBP, and 3 6×His are purified using commercially available affinity matrices such as immobilized glutathione, calmodulin, and metal-chelate resins, respectively. FLAG and MYC are purified using commercially available monoclonal and polyclonal antibodies. A proteolytic cleavage site may be located between the desired protein sequence and the heterologous moiety for ease of separating the desired protein following purification. Methods for recombinant protein expression and purification are discussed in Ausubel (supra, unit 16) and are commercially available (Invitrogen, San Diego Calif.).

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N, N-dimethylformamide. The peptide is cleaved between the peptide carboxy terminus and the linker group to yield a peptide acid or amide. (Novabiochem 1997/98 Catalog and Peptide Synthesis Handbook, San Diego Calif., pp. S1–S20). Automated synthesis may also be carried out on machines such as the ABI 431 A peptide synthesizer (PE Biosystems). A protein or portion thereof may be substantially purified by preparative high performance liquid chromatography and its composition confirmed by amino acid analysis or by sequencing (Creighton (1984) *Proteins, Structures and Molecular Properties*, W H Freeman, New York N.Y.).

Preparation and Screening of Antibodies

Various hosts including goats, rabbits, rats, mice, humans, and others may be immunized by injection with *M. catarrhalis* protein or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of about five to fifteen amino acids which are identical to a portion of the natural protein. Oligonucleotides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, eg, Kohler et al. (1975) Nature 256:495–497; Kozboret et al. (1985) J Immunol Methods 81:31–42; Coteet et al. (1983) Proc Natl Acad Sci 80:2026–2030; and Cole et al. (1984) Mol Cell Biol 62:109–120.)

Alternatively, techniques described for the production of single chain antibodies may be adapted, using methods known in the art, to produce epitope specific single chain antibodies. Antibody fragments ie which contain specific binding sites for epitopes of the *M. catarrhalis* protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 246:1275–1281).

The *M. catarrhalis* protein may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of labels and conjugation techniques are known by those skilled in the art and may be used in various nucleic acid molecule, protein, and antibody assays. Synthesis of labeled molecules may be achieved using Promega (Madison Wiss.) or APB kits for incorporation of a labeled nucleotide such as $^{32}$P-dCTP, Cy3-dCTP or Cy5-dCTP (APB) or amino acid such as $^{35}$S-methionine (APB). Nucleotides and amino acids may be directly labeled with a variety of substances including fluorescent, chemiluminescent, or chromogenic agents and the like, by chemical conjugation to amines, thiols and other groups present in the molecules using reagents such as BIODIPY or FITC (Molecular Probes, Eugene OR).

Diagnostics

The nucleic acid molecules, fragments, oligonucleotides, complementary RNA and DNA molecules, and peptide nucleic acids (PNAs) may be used to detect and quantify differential gene expression, absence/presence vs. excess, of mRNAs or to monitor mRNA levels following drug treatment. Conditions, diseases or disorders associated with *M. catarrhalis* gene expression may include conditions and diseases such as allergies, asthma, bronchitis, chronic obstructive pulmonary disease, emphysema, endocarditis, hypereosinophilia, meningitis, otitis media, pneumonia, sinusitis, and various respiratory distress syndromes. The diagnostic assay may use hybridization or amplification technology to compare gene expression in a biological sample from a patient to expression in disease and control standards in order to detect differential gene expression. Qualitative or quantitative methods for this comparison are well known in the art.

For example, the nucleic acid molecule, fragment, or probe may be labeled by standard methods and added to a sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of elevated amounts of *M. catarrhalis* is responsible for the associated condition or disease.

In order to provide a basis for the diagnosis of a condition, disease or disorder associated with gene expression, a normal or standard expression profile is established. This may be accomplished by combining a biological sample taken from normal subjects, animal or more preferably human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition or diseases listed above. Deviation from standard values toward those associated with a particular diagnosed condition is used to diagnose the patient.

Such assays may also be used to evaluate the efficacy of a particular therapeutic treatment regimen in animal studies or in a clinical trial. Once efficacy is established, these assays may be used on a regular basis to determine if the therapy is effective in an individual patient. The results obtained from successive patient assays may be used over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays, and fluorescence activated cell sorting. A two-site, monoclonal-based immunoassay utilizing monoclonal antibodies reactive to two non-interfering epitopes is preferred, but a competitive binding assay may be employed. (See, eg, Coligan et al. (1997) *Current Protocols in Immunology*, Wiley-Interscience, New York N.Y.; Pound, supra.)

Therapeutics

Chemical and structural similarity, in the context of sequences, signatures and motifs, antigenic epitopes and the like, generally exists between regions of homologous proteins. Comparisons of *M. catarrhalis* nucleic acid molecules and proteins with those of other *M. catarrhalis* strains, other bacteria and other organisms allow preselection of therapeutic agents that affect the pathogenic organism without harming the host. Such therapeutic agents are useful in treating conditions and diseases such as allergies, asthma, bronchitis, chronic obstructive pulmonary disease, emphysema, endocarditis, hypereosinophilia, meningitis, otitis media, pneumonia, sinusitis, and various respiratory distress syndromes caused by *M. catarrhalis*. In conditions associated with increased expression or activity of *M. catarrhalis* nucleic acid molecule or protein, it is desirable to decrease expression or protein activity.

In one embodiment, a ligand such as an antagonist, antibody, or inhibitor identified by screening a plurality of molecules with the *M. catarrhalis* protein is administered to the subject to decrease the activity of the *M. catarrhalis* or homologous protein as it is overexpressed during pathogenesis.

In another embodiment, a composition comprising the substantially purified ligand and a pharmaceutical carrier may be administered to a subject to decrease the activity of the *M. catarrhalis* or homologous protein as it is overexpressed during pathogenesis. In one aspect, an antibody which specifically binds the *M. catarrhalis* protein may be used as a targeting or delivery mechanism for bringing a pharmaceutical agent to cells or tissues which are affected by the overexpression of the *M. catarrhalis* protein.

Any of the ligands may be administered in combination with other therapeutic agents. Selection of the agents for use in combination therapy may be made by one of ordinary skill in the art according to conventional pharmaceutical principles. A combination of therapeutic agents may act synergistically to effect prevention or treatment of a particular condition at a lower dosage of each agent.

Modification of Gene Expression Using Nucleic Acids

Gene expression may be modified by designing complementary or antisense molecules (DNA, RNA, or PNA) to the 5',3', or intronic regions of the *M. catarrhalis* nucleic acid molecule. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and MRNA. In one alternative, a library of cDNA molecules may be screened to identify those which specifically bind a regulatory, untranslated *M. catarrhalis* sequence. Delivery of this inhibitory nucleotide sequence using a vector designed to be transferred from transformed *M. catarrhalis* cells to infectious *M. catarrhalis* via genetic recombination is contemplated.

Ribozymes, enzymatic RNA molecules, may also be used to catalyze the specific cleavage of an *M. catarrhalis* RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other derivative nucleotide molecules. Either the inclusion of nontraditional bases such as inosine, queosine, and wybutosine, and/or the modification of adenine, cytidine, guanine, thymine, and uridine with acetyl-, methyl-, thio- groups renders the molecule less available to endogenous bacterial endonucleases.

Screening Assays

The *M. catarrhalis* nucleic acid molecule may be used to screen a plurality or a library of molecules or compounds for specific binding affinity. The molecules or compounds may be selected from aptamers, DNA molecules, RNA molecules, PNAs, peptides, transcription factors, enhancers, repressors, regulatory proteins and other ligands which modulate the activity, replication, transcription, or translation of the nucleic acid molecules in the biological system. The assay involves combining the *M. catarrhalis* nucleic acid molecule or a fragment thereof with molecules or compounds under conditions to allow specific binding, and detecting specific binding to identify at least one ligand which specifically binds the *M. catarrhalis* nucleic acid molecule.

Similarly the *M. catarrhalis* protein or a portion thereof may be used to screen a plurality of libraries of molecules or compounds in any of a variety of screening assays. The molecules or compounds may be selected from aptamers, DNA molecules, RNA molecules, peptide nucleic acids, peptides, mimetics, proteins, agonists, antagonists, antibodies, inhibitors, immunoglobulins, pharmaceutical agents, drug compounds, and the like. The protein or portion thereof employed in such screening may be free in solution, affixed to an abiotic or biotic substrate (eg, borne on a cell surface), or located intracellularly. Specific binding between the protein and molecule may be measured. One method for high throughput screening using very small assay volumes and very small amounts of test compound is described in U.S. Pat. No. 5,876,946, incorporated herein by reference, which teaches how to screen large numbers of molecules for specific binding to a protein.

Purification of Ligand

The *M. catarrhalis* nucleic acid molecule or a fragment thereof may be used to purify a ligand from a sample. A method for using a *M. catarrhalis* nucleic acid molecule or a fragment thereof to purify a ligand would involve combining the nucleic acid molecule or a fragment thereof with a sample under conditions to allow specific binding, detecting specific binding, recovering the bound *M. catarrhalis* nucleic acid molecule, and using an appropriate agent to separate the *M. catarrhalis* nucleic acid molecule from the purified ligand.

Similarly, the protein or a portion thereof may be used to purify a ligand from a sample. A method for using a *M. catarrhalis* protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of a pharmaceutical agent which ameliorates the symptoms or condition. Therapeutic efficacy and toxicity of such agents may be determined by standard pharmaceutical procedures in cell cultures or experimental animals, eg, $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

Rational Drug Design

The goal of rational drug design is to produce structural analogs of biologically active *M. catarrhalis* proteins of interest or of ligands with which they interact. Any of these examples can be used to fashion drugs which are more active or stable forms of the protein, or which enhance or interfere with the function of a protein in vivo (Hodgson (1991) Bio/Technology 9:19–21).

In one approach, the three-dimensional structure of an *M. catarrhalis* protein, or of an *M. catarrhalis* protein-inhibitor complex, is determined by X-ray crystallography, by computer modeling or, most typically, by a combination of the two approaches. Both the shape and charges of the protein must be ascertained to elucidate the structure and to determine active site(s). Less often, useful information regarding the structure of a protein may be gained by modeling based on the structure of homologous proteins. In both cases, relevant structural information is used to design analogous *M. catarrhalis* protein-like molecules or to identify efficient inhibitors.

Useful examples of rational drug design may include molecules which have improved activity or stability, as shown by Braxton et al. (1992, *Biochem* 31:7796–7801), or which act as inhibitors, agonists, or antagonists of *M. catarrhalis* peptides, as shown by Athaudaet al. (1993, *J Biochem* 113:742–746).

It is also possible to isolate a target-specific antibody, selected by functional assay, as described above, and then to solve its crystal structure. This approach, in principle, yields a pharmacore upon which wa subsequent drug design can be based. It is possible to bypass protein crystallography altogether by generating anti-idiotypic antibodies (anti-ids) to a functional, pharmacologically-active antibody. As a mirror image of a mirror image, the binding site of the anti-id is an analog of the original receptor. The anti-id can be used to identify and isolate peptides from banks of chemically or biologically-produced peptides. The isolated peptides act as the pharmacore.

EXAMPLES

I Shotgun Sequencing Strategy

The strategy for sequencing the *M. catarrhalis* genome was a modification of the shotgun approach to whole genome sequencing described by Lander and Waterman (1988 Genomics 2:231). They applied the equation for the Poisson distribution $p_x = m^x e^{-m}/x!$, where x is the number of occurrences of an event, m is the mean number of occurrences, and $P_x$ is the probability that any given base is not sequenced after a certain amount of random sequence has been generated. If L is the genome length, n is the number of clones insert ends sequenced, and w is the sequencing read length, then m=nw/L, and the probability that no clone originates at any of the w bases preceding a given base, ie, the probability that a base is not sequenced, is $p_0 = e^{-m}$. For sequencing where $p_0 > 0$, the total gap length is $Le^{-m}$, and the average gap size is L/n.

The shotgun approach has recently been used to sequence the genomes of *H. influenzae* (Fleischmann et al. (1995) Science 269:496; WO 96/33276), *Mycoplasma genitalium* (Fraser et al. (1995) Science 270:397 and *Methanococcus iannashii* (Bult et al. (1996) Science 273:1058). All of these microbes have relatively small genomes of 1.8, .6, and 1.8 megabases, respectively. The size of the *M. catarrhalis* genome is estimated to be 1.9 megabases.

II Construction of the Genomic Library

An *M. catarrhalis* genomic DNA library was constructed using DNA purified from the gram negative, aerobic diplococcus, *M. catarrhalis*, ATCC accession number 43617. The isolate was obtained from transtracheal aspirate of a coal miner with chronic bronchitis. The G+C content is 42%.

Using a syringe fitted with a 0.0025 in. Ruby orifice (Stanford University, Stanford Calif.), 50 μg of *M. catarrhalis* DNA was sheared into 1.5–2.9 kb fragments. The shearing process was monitored by electrophoresis of a subsample of sheared DNA on a 0.8% SEAKEM GTG agarose gel (FMC Bioproducts, Rockland Me.) in 1×TAE buffer at about 950 V-h. Comparison with a DNA ladder with known size fragments was used to verify the size and quality of the sheared DNA.

Sheared DNA was visualized with low wavelength UV and bands of 1.5 to 2.8 kbs were removed from a preparative 0.8% SEAKEM GTG agarose gel (FMC Bioproducts). The 1.5–2.9 kb fragments were electrophoresced through a preparative 0.8% SEAPLAQUE GTG low melt agarose gel (FMC Bioproducts) in 1×TAE buffer at about 850 V-h. The DNA band was removed from the low melt agarose, placed in an microcentrifuge tube, and the agarose melted at 65 C for 10–15 minutes. After 5 minutes of heating, the melted agarose was diluted with a half volume of double distilled water, and the sample was equilibrated to 42 C. β-AGARASE (New England Biolabs (NEB), Beverly Mass.) and 10×β-AGARASE (NEB) were added, and the preparation was incubated for 1–3 hours with addition of a half initial volume of β-AGARASE (NEB)after 1 hour and mixing by inversion every half hour. The DNA was extracted once with phenol:chloroform:isoamyl alcohol (25:24:1) followed by extraction with chloroform:isoamyl alcohol (24:1) and precipitated by addition of 1–3 μl glycogen, 1/10 volume 3M NaOAc, and 2.5 volumes cold 100% ethanol. The sample was stored overnight at −20 C.

The purified DNA strands were treated with BAL31 (NEB) at 1 U/20 μg DNA in a final volume of 50 μl at 30 C for 10 minutes to prepare blunt ends. Then the DNA was re-extracted as above (phenol:chloroform:isoamyl alcohol followed by chloroform:isoamyl alcohol). The DNA was reprecipitated as above and stored at −20 C until ligation into the vector.

The PBLUESCRIPT plasmid (Stratagene) was cut with SmaI endonuclease, and the ends of the strands dephosphorylated to prepare the BS.S2 vector. The purified *M. catarrhalis* DNA (2 μg) was ligated into the BS.S2 vector (1 μg) with T4 DNA ligase (Life Technologies) for 4 hours at 14 C. Following the ligation reaction, the ligated DNA was extracted and precipitated as above. The ligated vector:insert DNA was the size selected (vector+insert=4.4–5.7 kb) and purified by gel electrophoresis and extracted as described above.

Following gel purification, the ends of the vector:insert DNA were repaired using T4 DNA polymerase (NEB) for 5 minutes at 37 C, re-extracted and precipitated as above, and self-ligated into circles with T4 DNA ligase (Life Technologies). After 10 minutes, the ligation reaction was stopped by heating at 70 C for 10 minutes.

The circular plasmid was transformed into DHIOB competent cells (Life Technologies) by electroporation at 1.8 volts. Transformed cells were selected by growth on X-Gal+ isopropyl beta-D-thiogalactopyranoside (IPTG)+2× carbenicillin (carb) LB agar plates.

III Isolation of Clones and Sequencing

Plasmid DNA was released from the cells and purified using the REAL PREP 96 plasmid kit (QIAGEN, Chatsworth Calif.). This kit enabled simultaneous purification of 96 samples in a 96-well block using multi-channel reagent dispensers. The recommended protocol was employed except for the following changes: 1) the bacteria were cultured in 1 ml of sterile TERRIFIC BROTH (BD Biosciences, Sparks Md.) with carb at 25 mg/l and glycerol at 0.4%; 2) after inoculation and incubation for 19 hours, the cells were lysed with 0.3 ml of lysis buffer; and 3) following isopropanol precipitation, the plasmid DNA pellet was resuspended in 0.1 ml of distilled water. After this final step, samples were transferred to a 96-well block for storage at 4 C.

The DNA inserts were prepared for sequencing using a 96 well HYDRA microdispenser (Robbins Scientific) in combination with DNA ENGINE thermal cyclers (MJ Research). After thermal cycling, the A, C, G, and T reactions with each DNA template were combined. Then, 50 μl 100% ethanol was added, and the solution was spun at 4 C for 30 min at 4500 rpm in a centrifuge (Jouan, Winchester Va.). After the pellet was dried for 15 min under vacuum, the DNA sample was dissolved in 3 μl of formaldehyde/50 mM EDTA and loaded on wells in volumes of 1 μl per well for sequencing. Sequencing used the method of Sanger and Coulson (1975, J. Mol. Biol. 94:441f) and an ABI PRISM 377 sequencing systems (PE Biosystems). After electrophoresis for four hours on 4% acrylamide gels on 36 cm plates at 2.3 kV, approximately 500–650 bps were determined per sequence.

IV Sequence Processing and Contiguous Sequence Assembly

Sequences were generated from either shotgun sequencing or closure sequencing. Closure sequences were obtained by directed genomic walks or PCR of specific genomic regions. In the latter case, the PCR products were sequenced.

Sequences were edited in a two-step process. In the first step, vector sequences from both the 5' and 3' ends were clipped using the algorithm provided in USSN 09/276,534 filed Mar. 25, 1999. In the second step, possible contaminating sequence was removed by reading each raw sequence and performing a cross-match search against a contamination database containing known vector sequences and DNA marker sequences. Sequences with cross-match scores of 18 or greater were removed.

Contigs were assembled using PHRAP (Green, supra) which aligns multiple, overlapping DNA sequences to form a contiguous consensus sequence. Alignments were influenced by quality scores assigned to each base in a sequence. A single sequence cannot belong to more than one contig.

The 41 contigs presented in Table 1 and the Sequence Listing were assembled from 47385 individual sequences. The contigs represent approximately 13.3×coverage or 100.7% of the M. catarrhalis genome.

V Gene Finding

ORF identification was carried out through combination of BLAST (Karlin, supra) and FASTA searches. These serial searches compared the consensus sequences of the assembled contigs, presented in Table 1, against sequences in public-domain databases. The searches identified similarity matches, or "hits", that indicated an ORF within the sequence.

The consensus sequences of the contigs were analyzed against the GenBank peptide (GenPept) database. The ORF identification process assigned ORFs to loci on a contig. If a match was found at a P-value less than or equal to 1e-6, the corresponding locus on the contig was designated as an ORF. This portion of the contig was masked by Ns, and the consensus sequence underwent a second BLASTX or FASTX search against the GenPept database. Again, the match with the lowest P-value (less than or equal to 1e-6) was used to identify a second ORF. The corresponding sequences were masked, and the process continued until all BLASTX and FASTX matches with P-values less than or equal to 1e-6 had been identified for a given contig. Then, the contigs were run through GeneMark, an algorithm for identifying putative ORFs. The GeneMark algorithm is described and developed in the following references: Borodovsky and Mcninch (1993) Computers & Chemistry 17:123; Blattner et al. (1993) Nucl Acid Res 21:5408; and Borodovsky et al.(1994) Trends Biochem Sci 19:309. After all possible homology and algorithm-based ORFs were identified, a process called ORF selection was applied. In this process GeneMark ORFs that overlapped homology-based ORFs were rejected, and homology-based ORFs were retained. GeneMark ORFs that did not overlap homology-based ORFs and those that overlapped other GeneMark ORFs were retained. Finally, all ORFs were annotated by performing BLAST2 comparisons against GenPept and taking annotation from the best hit with P-value less than or equal to 1e-6.

Contigs with high probability for ORFs, but no identified ORFs, were identified as "orphan" contigs (Table 1). Unannotated regions of contigs exceeding 500 bases in length were identified as "Long-Unannotated Regions" (LURs) and contain novel ORFs. The designations, orphan and LUR, were based on comparative analyses of the lengths of ORFs and unannotated regions.

A total of 1258 ORFs were identified by homology searches of the GenPept database with an additional 253 ORFs identified using the GeneMark algorithm.

VI Gene Clustering

In the final step of analysis, a gene clustering protocol is used to determine related ORFs within and across genomes. Gene clustering is carried out through BLAST2 pairwise comparisons of each ORF in the PATHOSEQ database (Incyte Genomics, Palo Alto Calif.) against every other ORF in the database. If two ORFs matched each other at a P-value less than or equal to 1e-15, they were placed in the same cluster. If a third ORF matched either of the first two ORFs at a P-value of less than or equal to 1e-15, the third ORF joined the cluster. Thus, clusters were formed so that any ORF in a cluster must match at least one other ORF in the cluster at less than or equal to the threshold P-value of 1e-15. The representative ORF for a cluster is the one with the best matched annotation.

VII Ordering of Contiguous Sequences

The ordering of contigs has been accomplished through three types of analyses: 1) 5'/3' sequence pair information, 2) annotation information, and 3) BLAST2 analysis of the ends of contigs. Contig ordering based on 5'/3' sequence pairs was done by identifying all 5'/3' sequence pairs (5' and 3' sequences with the same Sequence ID) that were not in the same contig, but span a gap between two contigs with the estimated distance between them of about 1.5–3.0 kb (the insert size of the library). Annotation information was used to determine contig order in two ways, either by identifying genes spanning contig gaps or by comparison with genes at the ends of contigs in related organisms with similar gene order.

Genes spanning gaps were identified by observing the N-terminal portion of an ORF at the end of one contig and the C-terminal portion of an ORF at the end of another contig. Two partial ORFs are considered to be portions of the same ORF when they meet this criteria and annotate to the same top five GenPept database entries. Comparison of two related organisms with similar gene order is used to predict contig ordering when one organism contains continuous gene order information over a region that spans a gap in the second organism. BLAST analysis of the ends of contigs was used to identify those contigs which overlapped, but failed to join because the sequence overlap did not meet the length or quality score required by PHRAP a (Green, supra). Table 2 shows the ordering of the M. catarrhalis contigs as supported by one or more of these analyses.

VIII Extension of Partial ORFs to Full Length

Using the DNA sequences disclosed herein, an ORF is extended using a modified XL-PCR (PE Biosystems) procedure. Oligonucleotide primers, one to initiate 5' extension and the other to initiate 3' extension were designed using the nucleotide sequence of the known fragment and OLIGO 4.06 software (National Biosciences). The initial primers were about 22 to 30 nucleotides in length, had a GC content of about 42%, and annealed to the target sequence at temperatures of about 55 C to about 68 C. Any fragment which would result in hairpin structures and primer-primer dimerizations was avoided. The genomic DNA library was used to extend the molecule. If more than one extension was needed, additional or nested sets of primers were designed.

High fidelity amplification was obtained by performing PCR in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair selected from the plasmid: Step 1: 94 C, 3 min; Step 2: 94 C, 15 sec; Step 3: 60 C, 1 min; Step 4: 68 C, 2 min; Step 5: Steps 2, 3, and 4 repeated 20 times; Step 6: 68 C, 5 min; Step 7: storage at 4 C In the alternative, parameters for the primer pair, T7 and SK+(Stratagene), were as follows: Step 1: 94 C, 3 min; Step 2: 94 C, 15 sec; Step 3: 57 C, 1 min; Step 4: 68C, 2 min; Step 5: Steps 2, 3, and 4 repeated 20 times; Step 6: 68 C, 5 min; Step 7: storage at 4 C.

The concentration of DNA in each well was determined by dispensing 100 µl PICOGREEN quantitation reagent (0.25% v/v; Molecular Probes) dissolved in 1×TE and 0.5 µl of undiluted PCR product into each well of an opaque fluorimeter plate (Coming Costar, Acton Mass.) and allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose mini-gel to determine which reactions were successful in producing longer sequence.

The extended sequences were desalted, concentrated, transferred to 384-well plates, digested with CviJI cholera virus endonuclease (Molecular Biology Research, Madison Wiss.), and sonicated or sheared prior to religation into pUC18 vector (APB). For shotgun sequencing, the digested fragments were separated on about 0.6–0.8% agarose gels, fragments were excised as visualized under UV light, and agarose removed/digested with AGARACE enzyme (Promega). Extended fragments were religated using T4 DNA ligase (NEB) into pUC18 vector (APB), treated with Pfu DNA polymerase (Stratagene) to fill-in restriction site overhangs, and transformed into competent *E. coli* cells. Transformed cells were selected on antibiotic-containing media, and individual colonies were picked and cultured overnight at 37 C in 384-well plates in LB/2×carb liquid media.

The cells were lysed, and DNA was amplified using Taq DNA polymerase (APB) and Pfu DNA polymerase (Stratagene) with the following parameters: Step 1: 94 C, 3 min; Step 2: 94 C, 15 sec; Step 3: 60 C, 1 min; Step 4: 72 C, 2 min; Step 5: steps 2, 3, and 4 repeated 29 times; Step 6: 72 C, 5 min; Step 7: storage at 4 C. DNA was quantified by PICOGREEN reagent (Molecular Probes) as described above. Samples with low DNA recoveries were reamplified using the conditions described above. Samples were diluted with 20% dimethysulphoxide (1:2, v/v), and sequenced using DYENAMIC energy transfer sequencing primers and the DYENAMIC DIRECT kit (APB) or the ABI PRISM BIGDYE terminator kit (PE Biosystems).

IX Labeling of Probes and Hybridization Analyses
Substrate Preparation

Nucleic acids are isolated from a biological source and applied to a substrate for standard hybridization protocols by one of the following methods. A mixture of nucleic acids, a restriction digest of genomic DNA, is fractionated by electrophoresis through an 0.7% agarose gel in 1×TAE running buffer and transferred to a nylon membrane by capillary transfer using 20×saline sodium citrate (SSC). Alternatively, the nucleic acids are individually ligated to a vector and inserted into bacterial host cells to form a library. Nucleic acids are arranged on a substrate by one of the following methods. In the first method, bacterial cells containing individual clones are robotically picked and arranged on a nylon membrane. The membrane is placed on bacterial growth medium, LB agar containing carb, and incubated at 37 C for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, nucleic acids are amplified from bacterial vectors by thirty cycles of PCR using primers complementary to vector sequences flanking the insert. Amplified nucleic acids are purified using SEPHACRYL-400 beads (APB). Purified nucleic acids are robotically arrayed onto a glass microscope slide (Corning Science Products, Corning N.Y.). The slide is previously coated with 0.05% aminopropyl silane (Sigma-Aldrich, St. Louis Mo.) and cured at 110 C. The arrayed glass slide (microarray) is exposed to UV irradiation in a STRATALINKER UV-crosslinker (Stratagene).

Probe Preparation

DNA probes are made from mRNA templates. Five micrograms of MRNA is mixed with 1 µg random primer (Life Technologies), incubated at 70 C for 10 minutes, and lyophilized. The lyophilized sample is resuspended in 50 µl of 1×first strand buffer (cDNA Synthesis systems; Life Technologies) containing a dNTP mix, [α-$^{32}$P]dCTP, dithiothreitol, and MMLV reverse transcriptase (Stratagene), and incubated at 42 C for 1–2 hours. After incubation, the probe is diluted with 42 µl dH$_2$O, heated to 95 C for 3 minutes, and on ice. mRNA in the probe is removed by alkaline degradation. The probe is neutralized, and degraded MRNA and unincorporated nucleotides are removed using a PROBEQUANT G-50 column (APB). Probes are labeled with fluorescent markers, Cy3-dCTP or Cy5-dCTP (APB), in place of the radionucleotide, [$^{32}$P]dCTP.

Hybridization

Hybridization is carried out at 65 C in a hybridization buffer containing 0.5 M sodium phosphate (pH 7.2), 7% SDS, and I mM EDTA. After the substrate is incubated in hybridization buffer at 65 C for at least 2 hours, the buffer is replaced with 10 ml of fresh buffer containing the probes. After incubation at 65 C for 18 hours, the hybridization buffer is removed, and the substrate is washed sequentially under increasingly stringent conditions, up to 40 mM sodium phosphate, 1% SDS, 1 mM EDTA at 65 C. To detect signal produced by a radiolabeled probe hybridized on a membrane, the substrate is exposed to a PHOSPHORIMAGER cassette (APB), and the image is analyzed using IMAGEQUANT data analysis software (APB). To detect signals produced by a fluorescent probe hybridized on a microarray, the substrate is examined by confocal laser microscopy, and images are collected and analyzed using GEMTOOLS gene expression analysis software (Incyte Genomics).

X Complementary Nucleic Acid Molecules

Molecules complementary to the nucleic acid molecule, or a fragment thereof, are used to detect, decrease, or inhibit gene expression. Although use of oligonucleotides comprising from about 15 to about 30 base pairs is described, the same procedure is used with larger or smaller fragments or derivatives such as peptide nucleic acids (PNAs). Oligonucleotides are designed using OLIGO 4.06 software (National Biosciences) and a nucleic acid molecule of the Sequence Listing or fragment thereof. To inhibit transcription by preventing promoter binding, a complementary oligonucleotide is designed to bind to sequence 5' of the ORF, most preferably about 10 nucleotides before the initiation codon of the ORF. To inhibit translation, a complementary oligonucleotide is designed to prevent ribosomal binding to the mRNA encoding the *M. catarrhalis* protein.

XI Expression of an *M. catarrhalis* Protein

An *M. catarrhalis* nucleic acid molecule is subcloned into a vector containing an antibiotic resistance gene and the inducible T5 or T7 bacteriophage promoter in conjunction with the lac operator regulatory element. Recombinant vectors are transformed into BL21(DE3) competent cells (Stratagene). Antibiotic 1:S resistant bacteria express the bacterial protein upon induction with IPTG.

The protein is synthesized as a fusion protein with FLAG which permits affinity-based purification of the recombinant fusion protein from crude cell lysates. Kits for immunoaffinity purification using monoclonal and polyclonal anti-FLAG antibodies (Eastman Kodak, Rochester N.Y.) are commercially available. Following purification the heterogeneous moiety is proteolytically cleaved from the bacterial protein at specifically engineered sites. Purified protein is used directly in the production of antibodies or in activity assays.

XII Production of *M. catarrhalis* Protein Specific Antibodies

An *M. catarrhalis* produced as described above or an oligopeptide designed and synthesized using an ABI 431A peptide synthesizer (PE Biosystems) is used to produce an antibody. Animals are immunized with the protein or an oliopeptide-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods and machinery well known in the art are used to determine antibody titer and the amount of complex formation.

XIII Screening or Purifying Molecules Using Specific Binding

The nucleic acid molecule, or fragments thereof, or the protein, or portions thereof, are labeled with $^{32}$P-dCTP, Cy3-dCTP, Cy5-dCTP (APB), or BIODIPY or FITC (Molecular Probes), respectively. Libraries of candidate molecules previously arranged on a substrate are incubated in the presence of labeled nucleic acid molecule or protein. After incubation under conditions for either a nucleic acid or amino acid sequence, the substrate is washed, and any position on the substrate retaining label, which indicates specific binding or complex formation, is assayed, and the binding molecule is identified. Data obtained using different concentrations of the nucleic acid or protein are used to calculate affinity between the labeled nucleic acid or protein and the bound molecule.

XIV Identification of *M. catarrhalis* Genes Induced During Infection

In vivo expression technology (IVET) is used with the sequences, or ORFs, to identify *M. catarrhalis* genes specifically induced during infection or under pathogenic conditions (Mahan et al. (1993) Science 259:686). A library of random genomic fragments of *M. catarrhalis* is made and ligated to a gene for a selectable marker required for survival in the host animal. Only those *M. catarrhalis* cells harboring a fusion sequence containing an active promoter will survive passage through the host. Fusion bearing promoters with constitutive activity are identified and discarded by examining reporter activity on laboratory medium passaged *M. catarrhalis* bacteria. By harvesting *M. catarrhalis* cells from infection sites in the host and subtraction of the identified constitutively activated genes, a list of genes turned on during infection or under pathogenic conditions are compiled.

Host induced *M. catarrhalis* genes are identified using the *M. catarrhalis* sequences and ORFs disclosed herein and the method of differential fluorescence induction described by Valdivia and Falkow (1996; Mol Microbiol 22:367).

XV Identification of *M. catarrhalis* Genes Required for Survival in Host

Using the *M. catarrhalis* genomic sequences and ORFs, genes required for survival in a host is determined using the signature-tagged transposon method described by Hensel et al. (1995; Science 269:400). A library of *M. catarrhalis* mutants is marked with a unique oligonucleotide sequence for each disrupted gene. After passage of the library though an infected animal or other selective environment, putative survival genes are identified by absence of the mutant from the passaged library.

Various modifications of the described method and system of the invention will be apparent to those skilled in the art without departing from the scope and spirit of the invention. Although the invention has been describes specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

TABLE 1

| Contig | Size | Start | End | Locus ID | Identifier | P-value | Description |
|---|---|---|---|---|---|---|---|
| 1 | 429 | 4 | 264 | MCA101123 | g2634865 | 5.00E-18 | methylenetetrahydrofolate dehydrogenase |
| 5 | 4258 | 4030 | 4257 | MCA100094 | g145409 | 4.00E-17 | bacterioferritin |
| 5 | 4258 | 1264 | 2612 | MCA100203 | g3402236 | e-127 | L-serine dehydratase |
| 5 | 4258 | 3523 | 3978 | MCA100205 | g1673579 | 2.00E-51 | bacterioferritin |
| 5 | 4258 | 2 | 343 | MCA101132 | g1001512 | 3.00E-24 | methylenetetrahydrofolate dehydrogenase |
| 6 | 5009 | 41 | 1448 | MCA100317 | g1519052 | e-134 | succinyl CoA:3-oxoacid CoA transferase precursor |
| 6 | 5009 | 1777 | 4587 | MCA100318 | g1574147 | 0 | transferrin-binding protein, putative |
| 6 | 5009 | 4729 | 5007 | MCA101039 | g1786625 | 6.00E-13 | putative oxidoreductase |
| 7 | 6703 | 2960 | 3466 | MCA100395 | g3861150 | 6.00E-23 | probable 50S ribosomal protein L25 (rplY) |

TABLE 1-continued

| Contig | Size | Start | End | Locus ID | Identifier | P-value | Description |
|---|---|---|---|---|---|---|---|
| 7 | 6703 | 965 | 2437 | MCA100550 | g2465556 | e-155 | OpuE |
| 7 | 6703 | 3687 | 4250 | MCA100554 | g1573366 | 6-00E-44 | peptidyl-tRNA hydrolase (pth) |
| 7 | 6703 | 4491 | 5846 | MCA100555 | g1220106 | e-120 | hemN |
| 7 | 6703 | 351 | 563 | MCA101455 | g2731760 | 1.00E-13 | 30S subunit ribosomal protein S21 |
| 8 | 7424 | 2423 | 3103 | MCA100638 | g286176 | 4.00E-33 | negative regulator of pyocin genes |
| 8 | 7424 | 5081 | 6058 | MCA101449 | g48773 | 3.00E-97 | methyltransferase |
| 8 | 7424 | 3218 | 4327 | MCA101610 | | | |
| 8 | 7424 | 4320 | 5060 | MCA101612 | | | |
| 8 | 7424 | 6504 | 6665 | MCA101982 | | | |
| 8 | 7424 | 6662 | 6928 | MCA101983 | | | |
| 8 | 7424 | 6925 | 7320 | MCA101984 | g1742219 | 1.00E-08 | Exodeoxyribonuclease VIII (EC 3.1.11.—) (Exo VIII). |
| 9 | 10709 | 465 | 1976 | MCA100745 | g347071 | e-141 | 4-hydroxybutyrate coenzyme A transferase |
| 9 | 10709 | 2306 | 3046 | MCA100746 | g3063885 | 5.00E-30 | putative acyl-coA dehydrogenase |
| 9 | 10709 | 4192 | 5478 | MCA100748 | g1923241 | 4.00E-69 | site-specific recombinase |
| 9 | 10709 | 5983 | 7809 | MCA100749 | g216913 | 0 | principal sigma factor, rpoDA |
| 9 | 10709 | 8288 | 8701 | MCA100750 | | | |
| 9 | 10709 | 8698 | 9393 | MCA100751 | g1574756 | 3.00E-12 | conserved hypothetical transmembrane protein |
| 9 | 10709 | 3 | 200 | MCA101334 | g154276 | 3.00E-22 | peptide chain release factor 2 |
| 9 | 10709 | 9866 | 10330 | MCA101713 | g3025510 | 2.00E-33 | putative transglycosylase |
| 10 | 19988 | 12800 | 12973 | MCA100043 | g2281030 | 1.00E-22 | ZfiA protein |
| 10 | 19988 | 13066 | 13413 | MCA100044 | | | |
| 10 | 19988 | 966 | 2060 | MCA100336 | g4062697 | e-121 | Hypothetical protein in purB 5'region (orf-15). |
| 10 | 19988 | 2141 | 3409 | MCA100338 | g2633742 | 4.00E-18 | similar to hypothetical proteins from *B. subtilis* |
| 10 | 19988 | 15744 | 16295 | MCA100456 | g1805560 | 3.00E-36 | phosphoribosylglycinamide formyltransferase (EC 2.1.2.2) |
| 10 | 19988 | 16331 | 17356 | MCA100457 | g1788845 | e-130 | phosphoribosylaminoimidazole synthetase = AIR synthetase |
| 10 | 19988 | 17685 | 18677 | MCA100458 | g3861171 | 2.00E-27 | putative permease homolog (perM) |
| 10 | 19988 | 18921 | 19685 | MCA100459 | g3212215 | 2.00E-11 | conserved hypothetical protein |
| 10 | 19988 | 5532 | 8192 | MCA100516 | g1800083 | 0 | Alanyl-tRNA Synthetase (EC 6.1.1.7) |
| 10 | 19988 | 8821 | 10335 | MCA100518 | g2632668 | 3.00E-69 | similar to di-tripeptide ABC transporter |
| 10 | 19988 | 3517 | 4892 | MCA100711 | g1573637 | e-171 | adenylosuccinate lyase (purB) |
| 10 | 19988 | 11303 | 12571 | MCA100888 | g2983613 | e-106 | aspartokinase |
| 10 | 19988 | 13673 | 13906 | MCA101216 | g1573976 | 4.00E-31 | ribosomal protein L28 (rpL28) |
| 10 | 19988 | 13949 | 14101 | MCA101228 | g1790067 | 7.00E-18 | 50S ribosomal subunit protein L33 |
| 10 | 19988 | 14201 | 14950 | MCA101234 | g3342798 | 1.00E-29 | glutamine cyclotransferase precursor |
| 10 | 19988 | 8330 | 8503 | MCA101481 | | | |
| 10 | 19988 | 334 | 801 | MCA101636 | g1789103 | 9.00E-38 | orf, hypothetical protein |
| 11 | 14335 | 4618 | 5967 | MCA100986 | g1572963 | e-155 | conserved hypothetical protein |
| 11 | 14335 | 7881 | 8108 | MCA100989 | | | |
| 11 | 14335 | 8089 | 8514 | MCA100990 | | | |
| 11 | 14335 | 8504 | 9154 | MCA100991 | g455332 | 2.00E-07 | pilus expression protein |
| 11 | 14335 | 9281 | 10588 | MCA100992 | g459551 | 1.00E-73 | fimbrial assembly protein |
| 11 | 14335 | 10856 | 11347 | MCA100993 | g1573166 | 3.00E-44 | shikimic acid kinase I (aroK) |

TABLE 1-continued

| Contig | Size | Start | End | Locus ID | Identifier | P-value | Description |
|---|---|---|---|---|---|---|---|
| 11 | 14335 | 11422 | 12447 | MCA100994 | g2661441 | 6.00E-88 | 3-dehydroquinate synthetase |
| 11 | 14335 | 12538 | 13482 | MCA100995 | | | |
| 11 | 14335 | 13503 | 14108 | MCA100996 | g2950411 | 5.00E-26 | hypothetical protein Rv3588c |
| 11 | 14335 | 1110 | 2087 | MCA101460 | g4235484 | e-142 | malate dehydrogenase |
| 11 | 14335 | 2383 | 3599 | MCA101547 | g1790853 | 2.00E-25 | soluble lytic murein transglycosylase |
| 11 | 14335 | 7292 | 7798 | MCA101551 | g455330 | 4.00E-15 | membrane protein |
| 11 | 14335 | 14167 | 14335 | MCA101992 | | | |
| 12 | 21410 | 15 | 647 | MCA100476 | g2462048 | 9.00E-50 | monofunctional peptidoglycan transglycosylase |
| 12 | 21410 | 993 | 3011 | MCA100477 | g2462047 | 0 | polyphosphate kinase |
| 12 | 21410 | 3051 | 3521 | MCA100478 | g1573243 | 1.00E-34 | conserved hypothetical protein |
| 12 | 21410 | 3641 | 4690 | MCA100479 | g1573154 | e-142 | chorismate synthase (aroC) |
| 12 | 21410 | 5549 | 6016 | MCA100481 | g1786848 | 6.00E-38 | protein of lipoate biosynthesis |
| 12 | 21410 | 6421 | 7621 | MCA100938 | g1787162 | 9.00E-88 | nicotinate phosphoribosyltransferase |
| 12 | 21410 | 8297 | 9625 | MCA100940 | g1573601 | e-123 | conserved hypothetical protein |
| 12 | 21410 | 9759 | 10676 | MCA100941 | g149244 | 3.00E-59 | Lys R member |
| 12 | 21410 | 10956 | 12413 | MCA100942 | g4456996 | 5.00E-90 | permease for AmpC beta-lactamase expression AmpG |
| 12 | 21410 | 12579 | 13343 | MCA100943 | g1651602 | 3.00E-41 | Protoporphyrinogen oxidase (EC 1.3.3.4) hemK |
| 12 | 21410 | 13406 | 14134 | MCA100944 | g1787048 | 1.00E-40 | molybdopterin biosynthesis |
| 12 | 21410 | 14383 | 15528 | MCA100945 | g3261724 | 2.00E-42 | hypothetical protein Rv0647c |
| 12 | 21410 | 17885 | 18445 | MCA100947 | g41336 | 9.00E-49 | enterohemolysin 1 |
| 12 | 21410 | 4870 | 5397 | MCA101603 | g1573079 | 2.00E-71 | inorganic pyrophosphatase (ppa) |
| 13 | 31940 | 29883 | 30041 | MCA100005 | g3282800 | 2.00E-09 | 50S ribosomal protein L32 |
| 13 | 31940 | 17948 | 18358 | MCA100019 | g42833 | 2.00E-46 | ribosomal protein L16 (rplP) (aa 1-136) |
| 13 | 31940 | 20208 | 20510 | MCA100105 | g1789703 | 3.00E-29 | 30S ribosomal subunit protein S14 |
| 13 | 31940 | 22493 | 22663 | MCA100139 | g498362 | 1.00E-16 | ribosomal protein L30 |
| 13 | 31940 | 22675 | 23106 | MCA100140 | g1573807 | 8.00E-37 | ribosomal protein L15 (rpL15) |
| 13 | 31940 | 23182 | 24408 | MCA100141 | g606234 | e-111 | secY |
| 13 | 31940 | 18936 | 19301 | MCA100153 | g606244 | 1.00E-53 | 50S ribosomal subunit protein L14 |
| 13 | 31940 | 19325 | 19627 | MCA100154 | g1573799 | 3.00E-24 | ribosomal protein L24 (rpL24) |
| 13 | 31940 | 19660 | 20193 | MCA100155 | g1573800 | 2.00E-71 | ribosomal protein L5 (rpL5) |
| 13 | 31940 | 20528 | 20923 | MCA100157 | g1573802 | 1.00E-41 | ribosomal protein S8 (rpS8) |
| 13 | 31940 | 21077 | 21607 | MCA100158 | g710620 | 7.00E-58 | ribosomal protein L6 |
| 13 | 31940 | 21628 | 21969 | MCA100159 | g1573804 | 1.00E-32 | ribosomal protein L18 (rpL18) |
| 13 | 31940 | 21975 | 22469 | MCA100160 | g42986 | 8.00E-54 | S5 (rp5E) (aa 1-167) |
| 13 | 31940 | 14176 | 14808 | MCA100248 | g1573787 | 4.00E-78 | ribosomal protein L3 (rpL3) |
| 13 | 31940 | 14853 | 15425 | MCA100249 | g1037107 | 3.00E-70 | L4 |
| 13 | 31940 | 15437 | 15724 | MCA100250 | g510688 | 7.00E-17 | ribosomal protein L23 |
| 13 | 31940 | 15765 | 16586 | MCA100251 | g48648 | e-121 | ribosomal protein L2 (AA 1 - 274) |
| 13 | 31940 | 16605 | 16877 | MCA100252 | g1841326 | 1.00E-37 | ribosomal protein S19 |
| 13 | 31940 | 16890 | 17216 | MCA100253 | g42831 | 1.00E-35 | ribosomal protein L22 (rplV) (aa 1-110) |
| 13 | 31940 | 17222 | 17926 | MCA100254 | g42832 | 2.00E-78 | ribosomal protein S3 (rpsC) (aa 1-233) |
| 13 | 31940 | 11780 | 13402 | MCA100255 | g48826 | e-113 | orfF |
| 13 | 31940 | 10997 | 11554 | MCA100256 | g606188 | 1.00E-24 | oRF_f217; orfE of ECMRED, uses 2nd start |
| 13 | 31940 | 10381 | 10659 | MCA100257 | g2589194 | 1.00E-08 | Glu-tRNAGln amidotransferase subunit C |

TABLE 1-continued

| Contig | Size | Start | End | Locus ID | Identifier | P-value | Description |
|---|---|---|---|---|---|---|---|
| 13 | 31940 | 8809 | 10284 | MCA100258 | g1224069 | 0 | amidase |
| 13 | 31940 | 7813 | 8754 | MCA100259 | g1403365 | 0 | BRO-2 |
| 13 | 31940 | 3925 | 4569 | MCA100414 | g3493603 | 5.00E-26 | outer membrane protein homolog |
| 13 | 31940 | 24691 | 25044 | MCA100423 | g581217 | 6.00E-46 | ribosomal protein S13 (aa 1-118) |
| 13 | 31940 | 25068 | 25457 | MCA100424 | g4098575 | 7.00E-48 | ribosomal protein S11 |
| 13 | 31940 | 25473 | 26111 | MCA100425 | g42798 | 4.00E-72 | ribosomal protein S4 (aa 1-206) |
| 13 | 31940 | 26142 | 27107 | MCA100426 | g2896137 | e-112 | DNA-directed RNA polymerase alpha chain |
| 13 | 31940 | 27162 | 27518 | MCA100427 | g2896138 | 3.00E-52 | ribosomal large subunit protein L17 |
| 13 | 31940 | 29100 | 29645 | MCA100430 | | | |
| 13 | 31940 | 18361 | 18540 | MCA100557 | g1841330 | 9.00E-09 | ribosomal protein L29 |
| 13 | 31940 | 7570 | 7746 | MCA100583 | g2589196 | 2.00E-15 | Glu-tRNAGln amidotransferase subunit B |
| 13 | 31940 | 6307 | 7563 | MCA100584 | g1224071 | 0 | unknown |
| 13 | 31940 | 2606 | 3502 | MCA100588 | g304968 | 3.00E-45 | ORF_f310 |
| 13 | 31940 | 30365 | 31270 | MCA100612 | g3282803 | 2.00E-64 | malonyl CoA-acyl carrier protein transacylase |
| 13 | 31940 | 1 | 282 | MCA101350 | g1651578 | 2.00E-26 | Cell division inhibitor MinD. |
| 13 | 31940 | 488 | 748 | MCA101742 | g1651579 | 1.00E-14 | Cell division inhibitor MinC. |
| 13 | 31940 | 18573 | 18818 | MCA101811 | g606245 | 9.00E-23 | 30S ribosomal subunit protein S17 |
| 13 | 31940 | 31291 | 31908 | MCA101812 | g1173841 | 4.00E-62 | 3-ketoacyl-ACP reductase |
| 13 | 31940 | 27617 | 28207 | MCA101856 | g1742075 | 2.00E-29 | ORF_ID:o253#4; similar to [P45847] |
| 13 | 31940 | 28272 | 28676 | MCA101857 | g1788666 | 7.00E-34 | putative transporting ATPase |
| 13 | 31940 | 13809 | 14117 | MCA101858 | g1573786 | 4.00E-45 | ribosomal protein S10 (rpS10) |
| 13 | 31940 | 5219 | 5743 | MCA101999 | g2231996 | 2.00E-06 | cytochrome c5 |
| 14 | 19619 | 11690 | 13288 | MCA100149 | g1001407 | 2.00E-80 | iron utilization protein |
| 14 | 19619 | 18587 | 19294 | MCA100717 | g2314220 | 4.00E-26 | phosphatidylserine synthase (pssA) |
| 14 | 19619 | 17517 | 18404 | MCA100718 | g1573417 | 5.00E-39 | orfJ protein |
| 14 | 19619 | 16112 | 16555 | MCA100720 | g1573816 | 9.00E-36 | H. influenzae predicted coding region HI0787 |
| 14 | 19619 | 14601 | 15785 | MCA100721 | g4210610 | e-110 | DapE |
| 14 | 19619 | 13561 | 14508 | MCA100722 | g1651916 | 8.00E-78 | iron transport protein |
| 14 | 19619 | 759 | 1838 | MCA100895 | g1574693 | 5.00E-72 | UDP-N-acetylglucosamine |
| 14 | 19619 | 2157 | 2699 | MCA100896 | g2632721 | 3.00E-18 | similar to acetyltransferase |
| 14 | 19619 | 2894 | 4285 | MCA100897 | g42056 | e-148 | (UDP-N-acetylmuramate: L-alanine ligase) |
| 14 | 19619 | 4384 | 5265 | MCA100898 | g1574696 | 4.00E-78 | D-alanine--D-alanine ligase (ddlB) |
| 14 | 19619 | 5654 | 5914 | MCA100899 | g2622037 | 9.00E-11 | unknown |
| 14 | 19619 | 5994 | 6857 | MCA100900 | g2098748 | 3.00E-49 | oxidative stress transcriptional regulator; OxyR |
| 14 | 19619 | 7087 | 7644 | MCA100901 | g1064782 | 2.00E-63 | alkyl hydroperoxide reductase |
| 14 | 19619 | 8407 | 9966 | MCA100903 | g1786823 | e-135 | alkyl hydroperoxide reductase, F52a subunit |
| 14 | 19619 | 10365 | 10556 | MCA100904 | g1799927 | 5.00E-17 | similar to [P37096] |
| 14 | 19619 | 10801 | 11643 | MCA100905 | g4514346 | 2.00E-67 | MsmX |
| 14 | 19619 | 6 | 629 | MCA101403 | g882476 | 3.00E-57 | glutathione synthetase |
| 15 | 28626 | 10223 | 10792 | MCA100003 | | | |
| 15 | 28626 | 27408 | 28103 | MCA100097 | g403436 | 3.00E-27 | repressor protein |
| 15 | 2B626 | 24288 | 24542 | MCA100178 | g1001663 | 4.00E-16 | rare lipoprotein A |
| 15 | 28626 | 16822 | 17763 | MCA100385 | g453969 | e-103 | coproporphyrinogen oxidase |
| 15 | 28626 | 17790 | 18383 | MCA100386 | g1573172 | 2.00E-52 | GTP cyclohydrolase II (ribA) |
| 15 | 28626 | 12359 | 13507 | MCA100396 | g1684734 | 2.00E-44 | ORF396 protein |

TABLE 1-continued

| Contig | Size | Start | End | Locus ID | Identifier | P-value | Description |
|---|---|---|---|---|---|---|---|
| 15 | 28626 | 10910 | 12217 | MCA100397 | g146020 | 2.00E-78 | folypolyglutamate synthetase-dihydrofolate synthetase |
| 15 | 28626 | 1297 | 2204 | MCA100824 | g1786319 | 7.00E-91 | putative ATP-binding component of a transport system |
| 15 | 28626 | 2319 | 3065 | MCA100825 | g1786320 | 9.00E-75 | orf, hypothetical protein |
| 15 | 28626 | 3176 | 3997 | MCA100826 | g882689 | 2.00E-48 | ORF_o282 |
| 15 | 28626 | 6151 | 6777 | MCA100828 | g141797 | 6.00E-51 | phosphoribosyl anthranilate isomerase |
| 15 | 28626 | 6927 | 8117 | MCA100829 | g141798 | e-172 | tryptophan synthase beta-subunit |
| 15 | 28626 | 8163 | 8981 | MCA100830 | g144288 | 6.00E-51 | tryptophan synthase A protein (EC 4.2.1.20) |
| 15 | 28626 | 766 | 1017 | MCA100987 | g2865528 | 2.00E-10 | mono-heme c-type cytochrome ScyA |
| 15 | 28626 | 9250 | 10096 | MCA101005 | g1788655 | 2.00E-78 | acetylCoA carboxylase, carboxytransferase beta subunit |
| 15 | 28626 | 13890 | 14987 | MCA101042 | | | |
| 15 | 28626 | 15277 | 15660 | MCA101046 | | | |
| 15 | 28626 | 15667 | 15975 | MCA101766 | | | |
| 15 | 28626 | 4067 | 5800 | MCA101839 | g1573733 | 0 | prolyl-tRNA synthetase (proS) |
| 15 | 28626 | 18809 | 20821 | MCA101840 | g1574278 | e-166 | 1-deoxyxylulose-5-phosphate synthase (*E. coli*) |
| 15 | 28626 | 20981 | 21787 | MCA101843 | g1573958 | 4.00E-56 | extragenic suppressor (suhB) |
| 15 | 28626 | 22787 | 23935 | MCA101845 | g1657482 | 2.00E-13 | hypothetical protein |
| 15 | 28626 | 28257 | 28442 | MCA101846 | g403437 | 2.00E-11 | putative |
| 16 | 22407 | 21035 | 22123 | MCA100084 | g1573365 | e-141 | conserved hypothetical GTP-binding protein |
| 16 | 22407 | 3904 | 4449 | MCA100337 | g3091146 | 7.00E-25 | iron-starvation protein PigA |
| 16 | 22407 | 19532 | 20179 | MCA100398 | g3402250 | 4.00E-25 | putative transcriptional regulator |
| 16 | 22407 | 18427 | 19210 | MCA100399 | g1079662 | 1.00E-54 | catabolite repression control protein |
| 16 | 22407 | 16346 | 18019 | MCA100400 | g2649804 | 4.00E-70 | L-lactate permease (lctP) |
| 16 | 22407 | 152 | 415 | MCA101103 | | | |
| 16 | 22407 | 471 | 1757 | MCA101104 | g507736 | e-167 | PurA |
| 16 | 22407 | 2286 | 2729 | MCA101106 | g2909463 | 2.00E-08 | hypothetical protein Rv0274 |
| 16 | 22407 | 2747 | 2950 | MCA101107 | | | |
| 16 | 22407 | 2940 | 3770 | MCA101108 | g3261756 | 9.00E-14 | hypothetical protein Rv0939 |
| 16 | 22407 | 4923 | 5546 | MCA101110 | g1574542 | 5.00E-78 | endonuclease III (nth) |
| 16 | 22407 | 5747 | 6997 | MCA101111 | g1787188 | 2.00E-62 | putative ATP-dependent protease |
| 16 | 22407 | 8306 | 8893 | MCA101113 | g581247 | 2.00E-32 | gidB protein |
| 16 | 22407 | 8949 | 9728 | MCA101114 | g45713 | 2.00E-49 | unnamed protein product |
| 16 | 22407 | 9744 | 10025 | MCA101115 | | | |
| 16 | 22407 | 10335 | 11093 | MCA101116 | g45714 | 4.00E-59 | unnamed protein product |
| 16 | 22407 | 11190 | 12152 | MCA101117 | g1573007 | 3.00E-49 | conserved hypothetical protein |
| 16 | 22407 | 12332 | 13051 | MCA101118 | g1651444 | 1.00E-53 | 3-deoxy-manno-octulosonate cytidylyl transferase |
| 16 | 22407 | 13087 | 13668 | MCA101119 | | | |
| 16 | 22407 | 13707 | 14210 | MCA101120 | g972778 | 3.00E-23 | homology to delta subunit of DNA polymerase III |
| 16 | 22407 | 14905 | 16044 | MCA101122 | g1381737 | e-170 | lactate dehydrogenase |
| 17 | 23210 | 18014 | 20569 | MCA100120 | g2772586 | 0 | high molecular weight outer membrane protein |
| 17 | 23210 | 505 | 1527 | MCA101311 | g3170587 | e-105 | glyceraldehyde-3-phosphate dehydrogenase homolog |
| 17 | 23210 | 2353 | 3555 | MCA101313 | g1573894 | e-102 | GTP-binding protein (yhbZ) |

TABLE 1-continued

| Contig | Size | Start | End | Locus ID | Identifier | P-value | Description |
|---|---|---|---|---|---|---|---|
| 17 | 23210 | 3919 | 4956 | MCA101314 | g409791 | e-104 | uroporphyrinogen decarboxylase |
| 17 | 23210 | 6000 | 7055 | MCA101316 | g4154933 | 3.00E-71 | Protease DO |
| 17 | 23210 | 7823 | 8527 | MCA101318 | g1573324 | 1.00E-40 | ABC transporter, permease protein |
| 17 | 23210 | 8692 | 9441 | MCA101319 | g1431416 | 2.00E-12 | ORF YDL244w |
| 17 | 23210 | 9572 | 10231 | MCA101320 | g2293296 | 1.00E-34 | putative transporter |
| 17 | 23210 | 11483 | 12235 | MCA101323 | | | |
| 17 | 23210 | 13108 | 14196 | MCA101325 | g47094 | e-107 | 3-phosphoserine aminotransferase (AA 1-362) |
| 17 | 23210 | 14309 | 15082 | MCA101326 | g1552782 | 5.00E-42 | hypothetical protein |
| 17 | 23210 | 15932 | 17658 | MCA101328 | g452382 | e-150 | 2-isopropylmalate synthase |
| 17 | 23210 | 7143 | 7448 | MCA101647 | g1652439 | 6.00E-08 | hypothetical protein |
| 17 | 23210 | 15246 | 15692 | MCA101649 | g2217944 | 2.00E-26 | Lrp-family transcriptional regulators |
| 17 | 23210 | 10452 | 10742 | MCA101666 | g1001663 | 1.00E-23 | rare lipoprotein A |
| 17 | 23210 | 20720 | 21990 | MCA101696 | g537207 | 7.00E-40 | ORF_f277 |
| 17 | 23210 | 22380 | 22529 | MCA101725 | g996086 | 1.00E-09 | ORFY; non-essential for pilus assembly |
| 17 | 23210 | 22985 | 23149 | MCA101847 | | | |
| 17 | 23210 | 12265 | 13008 | MCA101963 | | | |
| 18 | 34001 | 23020 | 23238 | MCA100089 | | | |
| 18 | 34001 | 24445 | 24774 | MCA100093 | | | |
| 18 | 34001 | 27135 | 28022 | MCA100416 | g1890655 | 4.00E-90 | UDP-3-O-acyl-GlcNAc deacetylase |
| 18 | 34001 | 29225 | 29902 | MCA100418 | | | |
| 18 | 34001 | 31130 | 31741 | MCA100421 | g746400 | 7.00E-53 | regulatory protein |
| 18 | 34001 | 15193 | 15909 | McA100448 | g496598 | 2.00E-69 | ORF1 |
| 18 | 34001 | 184 | 930 | MCA100873 | g1209054 | 3.00E-87 | EtfS |
| 18 | 34001 | 972 | 1898 | MCA100874 | g1209055 | 6.00E-90 | EtfL |
| 18 | 34001 | 4318 | 5247 | MCA100877 | g309885 | e-100 | 'aspartate transcarbamoylase' |
| 18 | 34001 | 5421 | 6119 | MCA100878 | g1786864 | 2.00E-43 | orf, hypothetical protein |
| 18 | 34001 | 6359 | 7432 | MCA100879 | g309886 | 3.00E-73 | dihydroorotase-like |
| 18 | 34001 | 7488 | 8273 | MCA100880 | g2113931 | 9.00E-18 | citE |
| 18 | 34001 | 23341 | 23862 | MCA101248 | | | |
| 18 | 34001 | 26268 | 26834 | MCA101720 | g433670 | 1.00E-70 | elongation factor P |
| 18 | 34001 | 2166 | 2930 | MCA101753 | g1653441 | 1.00E-20 | rRNA methylase |
| 18 | 34001 | 3046 | 4006 | MCA101756 | g901869 | 2.00E-78 | fructose-1,6-/sedoheptulose-1,7-bisphosphate phosphatase |
| 18 | 34001 | 9314 | 10354 | MCA101758 | g1788660 | 2.00E-42 | erythronate-4-phosphate dehyrogenase |
| 18 | 34001 | 10507 | 11499 | MCA101759 | g2983326 | 3.00E-28 | hypothetical protein |
| 18 | 34001 | 11730 | 12191 | MCA101764 | g1786586 | 2.00E-29 | orf, hypothetical protein |
| 18 | 34001 | 25125 | 26090 | MCA101767 | g1790589 | 7.00E-77 | orf, hypothetical protein |
| 18 | 34001 | 12249 | 13307 | MCA101768 | g1621601 | 7.00E-67 | PurK |
| 18 | 34001 | 13435 | 13911 | MCA101769 | g1574461 | 1.00E-53 | phosphoribosylamino-imidazole carboxylase |
| 18 | 34001 | 8282 | 9238 | MCA101775 | g41552 | 7.00E-58 | genX |
| 18 | 34001 | 21669 | 22925 | MCA101780 | | | |
| 18 | 34001 | 23957 | 24285 | MCA101781 | g2649731 | 6.00E-23 | conserved hypothetical protein |
| 18 | 34001 | 31862 | 33821 | MCA101782 | g746401 | 0 | ATP-binding protein |
| 18 | 34001 | 30667 | 30945 | MCA101796 | g1750388 | 2.00E-19 | orf2 |
| 18 | 34001 | 15937 | 16377 | MCA101803 | g2314656 | 2.00E-16 | conserved hypothetical integral membrane protein |
| 18 | 34001 | 16523 | 18349 | MCA101806 | g2896133 | 3.00E-24 | outer membrane esterase |
| 18 | 34001 | 18662 | 19597 | MCA101808 | g2294845 | e-103 | biotin synthase |
| 18 | 34001 | 20305 | 20988 | MCA101813 | g3417415 | 1.00E-44 | phosphoserine phosphatase |
| 19 | 33778 | 32970 | 33659 | MCA100015 | g2459964 | 2.00E-36 | HisX |
| 19 | 33778 | 20378 | 21868 | MCA100026 | g608530 | e-106 | L-aspartate oxidase |
| 19 | 33778 | 15834 | 16912 | MCA100127 | g968930 | e-132 | peptide chain release factor 1 |
| 19 | 33778 | 17205 | 18047 | MCA100128 | g1498753 | 9.00E-76 | nicotinate-nucleotide pyrophosphorylase |

TABLE 1-continued

| Contig | Size | Start | End | Locus ID | Identifier | P-value | Description |
|---|---|---|---|---|---|---|---|
| 19 | 33778 | 19349 | 20326 | MCA100320 | g1651337 | e-116 | Quinolinate synthetase A. |
| 19 | 33778 | 10305 | 11824 | MCA100473 | g2313949 | 1.00E-98 | osmoprotection protein (proWX) |
| 19 | 33778 | 12732 | 14177 | MCA100475 | g1789015 | e-165 | succinate-semialdehyde dehydrogenase, NADP-dependent |
| 19 | 33778 | 2058 | 2579 | MCA100756 | | | |
| 19 | 33778 | 4059 | 4889 | MCA100758 | | | |
| 19 | 33778 | 31220 | 32257 | MCA100768 | g2695825 | 4.00E-58 | corA |
| 19 | 33778 | 29370 | 31016 | MCA100769 | g1573928 | e-119 | glutathione-regulated potassium efflux system protein |
| 19 | 33778 | 27814 | 29127 | MCA100770 | g1573294 | 3.00E-98 | conserved hypothetical protein |
| 19 | 33778 | 25151 | 27505 | MCA100771 | g2959335 | 0 | Lon-protease |
| 19 | 33778 | 24481 | 25038 | MCA100772 | g1754527 | 4.00E-16 | intracellular septation A |
| 19 | 33778 | 23332 | 23889 | MCA100774 | g3916254 | 2.00E-25 | ExbB |
| 19 | 33778 | 23892 | 24287 | MCA100946 | g3916255 | 1.00E-23 | ExbD |
| 19 | 33778 | 9106 | 9774 | MCA101121 | g927800 | 2.00E-20 | Ydr533cp; CAI: 0.24 |
| 19 | 33778 | 219 | 1652 | MCA101802 | | | |
| 19 | 33778 | 3487 | 3846 | MCA101805 | | | |
| 19 | 33778 | 4651 | 4911 | MCA101974 | | | |
| 19 | 33778 | 6334 | 6705 | MCA101975 | | | |
| 19 | 33778 | 2811 | 3494 | MCA101977 | | | |
| 19 | 33778 | 22342 | 23226 | MCA102006 | | | |
| 2 | 1169 | 157 | 555 | MCA100759 | g2633670 | 2.00E-17 | yzzE; similar to general stress protein |
| 2 | 1169 | 795 | 1166 | MCA101009 | g3929904 | 5.00E-18 | fumarate hydratase B, beta subunit |
| 20 | 31063 | 848 | 1366 | MCA100998 | g396321 | 2.00E-57 | nusG |
| 20 | 31063 | 1476 | 1898 | MCA100999 | g2367334 | 7.00E-51 | 50S ribosomal subunit protein L11 |
| 20 | 31063 | 1907 | 2581 | MCA101000 | g47257 | 2.00E-62 | L1 protein (AA 1-234) |
| 20 | 31063 | 2920 | 3411 | MCA101001 | g1573638 | 9.00E-63 | ribosomal protein L10 (rpL10) |
| 20 | 31063 | 3481 | 3852 | MCA101002 | g1573639 | 7.00E-25 | ribosomal protein L7/L12 (rpL7/L12) |
| 20 | 31063 | 4275 | 8360 | MCA101003 | g45729 | 0 | beta-subunit of RNA polymerase |
| 20 | 31063 | 8446 | 12564 | MCA101004 | g2367335 | 0 | RNA polymerase, beta prime subunit |
| 20 | 31063 | 12905 | 14122 | MCA101239 | g1573443 | e-146 | D-3-phosphoglycerate dehydrogenase (serA) |
| 20 | 31063 | 14321 | 15688 | MCA101240 | g1573119 | e-171 | glutathione reductase (gor) |
| 20 | 31063 | 16095 | 16997 | MCA101241 | g4062671 | 6.00E-73 | Hypothetical protein HI0959 |
| 20 | 31063 | 17242 | 19314 | MCA101242 | g1574519 | 6.00E-81 | tail specific protease (prc) |
| 20 | 31063 | 20177 | 20935 | MCA101244 | g1573922 | 4.00E-28 | conserved hypothetical protein |
| 20 | 31063 | 21988 | 22695 | MCA101246 | g2314002 | 5.00E-13 | H. pylori predicted coding region HP0862 |
| 20 | 31063 | 23138 | 23536 | MCA101247 | g1888564 | 7.00E-36 | ORFX |
| 20 | 31063 | 24093 | 24545 | MCA101249 | g4545247 | 6.00E-53 | invasion protein homolog |
| 20 | 31063 | 24726 | 26248 | MCA101250 | g2633966 | 5.00E-49 | chromosome segregation SMC protein homolog |
| 20 | 31063 | 28591 | 29325 | MCA101251 | g296030 | 4.00E-97 | ribosomal protein S2 |
| 20 | 31063 | 29460 | 30314 | MCA101252 | g1552747 | 4.00E-61 | elongation factor EF-Ts |
| 20 | 31063 | 30482 | 31063 | MCA101253 | g1079661 | 2.00E-47 | orotate phosphoribosyl transferase |
| 20 | 31063 | 26531 | 28321 | MCA101493 | g1237015 | 4.00E-44 | ORF4 |
| 20 | 31063 | 350 | 823 | MCA101880 | | | |
| 20 | 31063 | 21040 | 21933 | MCA101950 | g2983199 | 5.00E-07 | biotin [acetyl-CoA-carboxylase] ligase |
| 21 | 39003 | 30165 | 31499 | MCA100007 | g1772845 | e-130 | NAD(P)H-dependent glutamate dehydrogenase |
| 21 | 39003 | 28829 | 29935 | MCA100118 | g1786552 | e-134 | glutathione-dependent formaldehyde dehydrogenase |
| 21 | 39003 | 25255 | 26679 | MCA100217 | g1787999 | 4.00E-77 | orf, hypothetical protein |

TABLE 1-continued

| Contig | Size | Start | End | Locus ID | Identifier | P-value | Description |
|---|---|---|---|---|---|---|---|
| 21 | 39003 | 27082 | 27942 | MCA100218 | | | |
| 21 | 39003 | 27992 | 28813 | MCA100219 | g405878 | 1.00E-86 | probable esterase |
| 21 | 39003 | 20225 | 20965 | MCA100226 | g3220185 | 3.00E-31 | pteridine reductase |
| 21 | 39003 | 19027 | 20070 | MCA100227 | g882578 | 7.00E-55 | CG Site No. 933 |
| 21 | 39003 | 21277 | 22656 | MCA100347 | g1736694 | e-126 | Proline transport protein |
| 21 | 39003 | 24025 | 24876 | MCA100349 | g2570906 | 1.00E-64 | stearoyl-CoA desaturase |
| 21 | 39003 | 35864 | 38086 | MCA100561 | g1763284 | e-163 | penicillin-binding protein 1A |
| 21 | 39003 | 33490 | 35418 | MCA100562 | g862902 | 0 | high temperature protein G |
| 21 | 39003 | 8041 | 9210 | MCA101029 | g1806239 | 1.00E-35 | lipD |
| 21 | 39003 | 16664 | 18907 | MCA101134 | g1788806 | 0 | putative multimodular enzyme |
| 21 | 39003 | 15338 | 16315 | MCA101135 | g1009431 | e-106 | porphobilinogen synthase |
| 21 | 39003 | 13425 | 14354 | MCA101137 | g42903 | e-119 | ruvB gene product (AA 1 - 336) |
| 21 | 39003 | 12028 | 13293 | MCA101138 | g2909447 | e-147 | fadA2 |
| 21 | 39003 | 10330 | 11691 | MCA101140 | g3063883 | 8.00E-92 | putative 3-oxoacyl-[acyl-carrier protein] reductase |
| 21 | 39003 | 9377 | 10174 | MCA101141 | g2909445 | 3.00E-35 | hypothetical protein Rv0241c |
| 21 | 39003 | 7384 | 7893 | MCA101143 | g3046326 | 4.00E-55 | hypoxanthine phosphoribosyltransferase |
| 21 | 39003 | 4877 | 6769 | MCA101145 | g288532 | 0 | dihydroxy acid |
| 21 | 39003 | 2806 | 4254 | MCA101147 | g2078066 | 5.00E-97 | betP |
| 21 | 39003 | 1461 | 2414 | MCA101149 | g1001519 | 3.00E-23 | hypothetical protein |
| 21 | 39003 | 559 | 1209 | MCA101201 | | | |
| 21 | 39003 | 116 | 433 | MCA101854 | g2226116 | 2.00E-16 | hypothetical protein |
| 21 | 39003 | 38281 | 38810 | MCA101855 | g972976 | 3.00E-20 | 1-acyl-sn-glycerol-3-phosphate acyltransferase |
| 21 | 39003 | 6901 | 7305 | MCA101863 | | | |
| 21 | 39003 | 14701 | 15213 | MCA101864 | | | |
| 22 | 45613 | 33275 | 34222 | MCA100119 | g1786405 | 3.00E-57 | transcriptional regulator for nitrite reductase |
| 22 | 45613 | 31023 | 32033 | MCA100130 | g1653241 | 1.00E-40 | hemolysin |
| 22 | 45613 | 13590 | 14525 | MCA100133 | g476229 | e-150 | isopropylmalate dehydrogenase |
| 22 | 45613 | 40430 | 41209 | MCA100144 | g1799842 | 7.00E-62 | sulfate/thiosulfate transport protein cysW |
| 22 | 45613 | 41338 | 42090 | MCA100171 | g1799853 | 9.00E-60 | sulfate transport system permease protein cyst. |
| 22 | 45613 | 42522 | 42968 | MCA100210 | | | |
| 22 | 45613 | 42993 | 44153 | MCA100212 | g1573911 | 4.00E-84 | ATP-dependent RNA helicase (rh1B) |
| 22 | 45613 | 44209 | 45369 | MCA100213 | g1573441 | 2.00E-87 | oxygen-independent coproporphyrinogen III oxidase |
| 22 | 45613 | 10853 | 13060 | MCA100223 | g1000692 | 0 | LeuA |
| 22 | 45613 | 536 | 1627 | MCA100312 | g1790487 | 4.00E-49 | alanine racemase 1 |
| 22 | 45613 | 1693 | 3003 | MCA100313 | g145763 | e-106 | DnaB replication protein (dnaB) |
| 22 | 45613 | 3266 | 4333 | MCA100314 | g1786237 | 3.00E-66 | pyridoxine biosynthesis |
| 22 | 45613 | 8040 | 9071 | MCA100353 | g3758880 | e-153 | fructose-1,6-bisphosphate aldolase |
| 22 | 45613 | 9074 | 9676 | MCA100354 | g1573280 | 4.00E-29 | Holliday junction DNA helicase (ruvA) |
| 22 | 45613 | 10292 | 10609 | MCA100356 | g1850796 | 6.00E-19 | CynR protein |
| 22 | 45613 | 30261 | 30536 | MCA100450 | g1573206 | 3.00E-17 | conserved hypothetical protein |
| 22 | 45613 | 28267 | 30132 | MCA100451 | g3983168 | e-141 | SecD |
| 22 | 45613 | 27163 | 28047 | MCA100452 | g1573204 | 4.00E-55 | protein-export membrane protein (secF) |
| 22 | 45613 | 26200 | 26925 | MCA100453 | g1518782 | 4.00E-38 | penicillin-binding protein 5 |
| 22 | 45613 | 39609 | 40322 | MCA100541 | g1799841 | 2.00E-67 | sulfate-thiosulfate transport protein cysA |
| 22 | 45613 | 38143 | 39546 | MCA100542 | g1881700 | e-143 | RadA |

TABLE 1-continued

| Contig | Size | Start | End | Locus ID | Identifier | P-value | Description |
|---|---|---|---|---|---|---|---|
| 22 | 45613 | 36060 | 37833 | MCA100543 | g1680533 | 0 | phospho enol pyruvate carboxykinase |
| 22 | 45613 | 34862 | 35839 | MCA100544 | g2226145 | 4.00E-30 | hypothetical protein |
| 22 | 45613 | 15396 | 16193 | MCA100678 | g1572987 | 2.00E-90 | exodeoxyribonuclease III (xthA) |
| 22 | 45613 | 16548 | 18068 | MCA100679 | g1359473 | 0 | lysyl-tRNA-synthase |
| 22 | 45613 | 18097 | 19173 | MCA100680 | g1574159 | e-104 | DNA polymerase III, subunits gamma and tau (dnax) |
| 22 | 45613 | 20776 | 21252 | MCA100682 | g924993 | 8.00E-19 | transcriptional regulator LtrA |
| 22 | 45613 | 21816 | 22710 | MCA100684 | g1786984 | 3.00E-32 | putative transcriptional regulator LYSR-type |
| 22 | 45613 | 22855 | 23910 | MCA100685 | g2108220 | 1.00E-88 | hemolysin |
| 22 | 45613 | 24272 | 25591 | MCA100686 | g2209268 | 3.00E-69 | Na+/H+ antiporter |
| 22 | 45613 | 5347 | 6123 | MCA100727 | g1573537 | 1.00E-51 | diadenosine-tetraphosphatase (apaH) |
| 22 | 45613 | 4478 | 5278 | MCA100787 | g1786236 | 7.00E-62 | 5-adenosylmethionine-6-N',N'-adenosyl dimethyltransferase |
| 22 | 45613 | 6267 | 7456 | MCA101090 | g41422 | e-121 | phosphoglycerate kinase (AA 1-387) |
| 22 | 45613 | 32181 | 32786 | MCA101784 | | | |
| 23 | 33140 | 647 | 814 | MCA100041 | | | |
| 23 | 33140 | 2719 | 3444 | MCA100603 | g2330641 | 1.00E-22 | htrB |
| 23 | 33140 | 3463 | 5241 | MCA100604 | g1788173 | 0 | aspartate tRNA synthetase |
| 23 | 33140 | 5822 | 7239 | MCA100606 | g4062776 | 5.00E-83 | ORF_ID:o245#1 |
| 23 | 33140 | 7701 | 8581 | MCA100608 | g1574534 | 1.00E-72 | protease, putative (sohB) |
| 23 | 33140 | 8907 | 9644 | MCA100609 | g1524217 | 3.00E-47 | hypothetical protein Rv0945 |
| 23 | 33140 | 9956 | 10741 | MCA100610 | g41424 | 3.00E-45 | ORF4 (AA 1-197) |
| 23 | 33140 | 31971 | 33044 | MCA100705 | g1788953 | 8.00E-98 | 3-deoxy-D-arabinoheptulosonate-7-phosphate synthase |
| 23 | 33140 | 10882 | 11415 | MCA101509 | g1573653 | 8.00E-53 | DNA-3-methyladenine glycosidase I (tagI) |
| 23 | 33140 | 11492 | 12220 | MCA101510 | g3046322 | 2.00E-69 | O-acetylserine synthase; CysE2 |
| 23 | 33140 | 12686 | 13213 | MCA101511 | g3046324 | 1.00E-24 | unknown |
| 23 | 33140 | 13720 | 16956 | MCA101513 | g940886 | 0 | DNA polymerase III holoenzyme alpha subunit |
| 23 | 33140 | 17151 | 18281 | MCA101514 | g1573367 | 3.00E-93 | conserved hypothetical protein |
| 23 | 33140 | 18669 | 19625 | MCA101515 | g1799725 | 2.00E-69 | similar to [SwissProt Accession Number P39199] |
| 23 | 33140 | 19870 | 20970 | MCA101516 | g1162959 | e-123 | homologous to HI0365 in Haemophilus influenzae; ORF1 |
| 23 | 33140 | 21062 | 21676 | MCA101517 | | | |
| 23 | 33140 | 21735 | 22844 | MCA101518 | g1531668 | e-122 | AarC |
| 23 | 33140 | 22996 | 23775 | MCA101519 | g4155368 | 3.00E-53 | putative |
| 23 | 33140 | 23844 | 25085 | MCA101520 | g1573338 | e-117 | histidyl-tRNA synthetase (hisS) |
| 23 | 33140 | 25203 | 26036 | MCA101521 | g1573339 | 1.00E-12 | conserved hypothetical protein |
| 23 | 33140 | 26145 | 27266 | MCA101522 | g1805571 | 8.00E-33 | serine/threonine protein kinase (EC 2.7.1.—) |
| 23 | 33140 | 27407 | 28831 | MCA101523 | g1788858 | e-153 | putative GTP-binding factor |
| 23 | 33140 | 28941 | 29570 | MCA101524 | g2633978 | 1.00E-30 | ribonuclease H |
| 23 | 33140 | 29683 | 30894 | MCA101525 | g1694783 | 2.00E-67 | 1pxB |
| 23 | 33140 | 31117 | 31638 | MCA101526 | g1787602 | 4.00E-11 | orf, hypothetical protein |
| 23 | 33140 | 136 | 480 | MCA101883 | | | |
| 23 | 33140 | 882 | 1604 | MCA101889 | | | |
| 24 | 33248 | 31423 | 31823 | MCA101434 | g1046241 | 8.00E-16 | orf14 |
| 24 | 33248 | 25628 | 29158 | MCA101438 | g1651549 | 0 | Transcription-repair coupling protein mfd |
| 24 | 33248 | 24151 | 25353 | MCA101439 | g1685080 | 5.00E-30 | TolB |
| 24 | 33248 | 22836 | 23243 | MCA101441 | g1103861 | 1.00E-17 | TolR |

TABLE 1-continued

| Contig | Size | Start | End | Locus ID | Identifier | P-value | Description |
|---|---|---|---|---|---|---|---|
| 24 | 33248 | 22115 | 22702 | MCA101442 | g1103860 | 1.00E-37 | TolQ |
| 24 | 33248 | 17684 | 21622 | MCA101443 | g1574628 | 0 | ATP-dependent helicase (hrpa) |
| 24 | 33248 | 15920 | 16918 | MCA101445 | g2314661 | 2.00E-13 | lipase-like protein |
| 24 | 33248 | 14698 | 15579 | MCA101446 | g1840154 | 9.00E-36 | 36 kDa protein |
| 24 | 33248 | 13519 | 14589 | MCA101447 | g4155989 | 1.00E-12 | putative |
| 24 | 33248 | 12383 | 13468 | MCA101448 | g2314658 | 7.00E-25 | conserved hypothetical integral membrane protein |
| 24 | 33248 | 11331 | 11747 | MCA101450 | g1787709 | 2.00E-32 | orf, hypothetical protein |
| 24 | 33248 | 10560 | 11324 | MCA101451 | g3192702 | 6.00E-28 | gp19 |
| 24 | 33248 | 32602 | 33087 | MCA101505 | g1790034 | 3.00E-36 | orf, hypothetical protein |
| 24 | 33248 | 9940 | 10167 | MCA101507 | g1628368 | 1.00E-08 | gepA |
| 24 | 33248 | 5471 | 6674 | MCA101512 | g437700 | 5.00E-39 | traN |
| 24 | 33248 | 99 | 350 | MCA102008 | | | |
| 24 | 33248 | 1019 | 1525 | MCA102009 | | | |
| 24 | 33248 | 1526 | 2998 | MCA102010 | | | |
| 24 | 33248 | 2998 | 4413 | MCA102011 | | | |
| 24 | 33248 | 7022 | 8038 | MCA102014 | g2764860 | 9.00E-16 | gene 13 |
| 24 | 33248 | 8049 | 8252 | MCA102016 | | | |
| 24 | 33248 | 8313 | 8672 | MCA102017 | | | |
| 24 | 33248 | 23253 | 24080 | MCA102018 | | | |
| 24 | 33248 | 8674 | 9030 | MCA102026 | | | |
| 24 | 33248 | 9030 | 9377 | MCA102028 | | | |
| 24 | 33248 | 31013 | 31210 | MCA102029 | | | |
| 24 | 33248 | 32232 | 32447 | MCA102030 | | | |
| 25 | 31147 | 830 | 1147 | MCA100008 | g3776111 | 6.00E-32 | thioredoxin |
| 25 | 31147 | 3 | 593 | MCA100009 | g454841 | 3.00E-79 | |
| 25 | 31147 | 29786 | 30031 | MCA100048 | g1518927 | 1.00E-32 | ferredoxin |
| 25 | 31147 | 29298 | 29753 | MCA100049 | g1518926 | 2.00E-45 | protein for lipopolysaccharide core synthesis |
| 25 | 31147 | 12271 | 13725 | MCA100080 | g4200042 | 2-00E-81 | exopolyphosphatase |
| 25 | 31147 | 4751 | 5011 | MCA100380 | g663269 | 2.00E-13 | BolA |
| 25 | 31147 | 2616 | 4289 | MCA100381 | g2626753 | 2-00E-58 | sulfate transporter |
| 25 | 31147 | 1432 | 2072 | MCA100384 | g1786244 | 1.00E-36 | orf, hypothetical protein |
| 25 | 31147 | 6397 | 7359 | MCA100487 | g1052826 | 8.00E-97 | phosphate binding protein |
| 25 | 31147 | 7554 | 8459 | MCA100488 | g1574215 | 1.00E-70 | phosphate ABC transporter, permease protein (pstC) |
| 25 | 31147 | 8539 | 9348 | MCA100489 | g42397 | 9.00E-76 | phoT (pstA) gene product (aa 1-296) |
| 25 | 31147 | 9516 | 10262 | MCA100490 | g1790162 | 7.00E-94 | ABC transporter, high-affinity phosphate-specific |
| 25 | 31147 | 10496 | 11182 | MCA100491 | g1786599 | 6.00E-64 | positive response regulator for pho regulon |
| 25 | 31147 | 11382 | 12201 | MCA100492 | g3282775 | 6.00E-53 | histidine protein kinase PhoR |
| 25 | 31147 | 5110 | 5892 | MCA100803 | g1653285 | 6.00E-19 | hypothetical protein |
| 25 | 31147 | 14590 | 15696 | MCA101453 | | | |
| 25 | 31147 | 16710 | 17657 | MCA101456 | g2766195 | 3.00E-15 | putative permease BhiE |
| 25 | 31147 | 17742 | 18020 | MCA101457 | g2415545 | 2.00E-19 | permease protein |
| 25 | 31147 | 18338 | 19156 | MCA101458 | g1574806 | 7.00E-65 | spermidine/putrescine ABC transporter |
| 25 | 31147 | 19449 | 20102 | MCA101459 | g4539576 | 4.00E-10 | putative morphological differentiation-associated protein |
| 25 | 31147 | 20696 | 21667 | MCA101461 | g1881313 | 8.00E-80 | similar to alkanal monooxygenase alpha chain |
| 25 | 31147 | 21810 | 22436 | MCA101462 | g1788844 | 6.00E-70 | uracil phosphoribosyltransferase |
| 25 | 31147 | 23978 | 25966 | MCA101464 | g1574651 | 0 | DNA ligase (lig) |
| 25 | 31147 | 25990 | 26874 | MCA101465 | | | |
| 25 | 31147 | 27604 | 28056 | MCA101467 | g1788973 | 5.00E-48 | small protein B |
| 25 | 31147 | 28358 | 29119 | MCA101468 | g478986 | 1.00E-47 | NADPH-flavin oxidoreductase |
| 25 | 31147 | 15766 | 16581 | MCA101993 | g1360216 | 1.00E-06 | ORF YLL031c |
| 26 | 34279 | 24575 | 24982 | MCA100071 | g1787709 | 2.00E-33 | orf, hypothetical protein |
| 26 | 34279 | 23822 | 24559 | MCA100072 | g3192702 | 4.00E-32 | gp19 |

TABLE 1-continued

| Contig | Size | Start | End | Locus ID | Identifier | P-value | Description |
|---|---|---|---|---|---|---|---|
| 26 | 34279 | 25922 | 28576 | MCA100506 | g3192704 | 0 | gp21 |
| 26 | 34279 | 30501 | 30830 | MCA100508 | | | |
| 26 | 34279 | 30 | 378 | MCA100640 | g1574256 | 2.00E-24 | H. influenzae predicted coding region HI1422 |
| 26 | 34279 | 775 | 1820 | MCA100642 | g15152 | 4.00E-31 | alpha gene (pot.P4-specific DNA primase) (AA 1-777) |
| 26 | 34279 | 3747 | 4175 | MCA100645 | | | |
| 26 | 34279 | 4724 | 5230 | MCA100647 | | | |
| 26 | 34279 | 5715 | 7454 | MCA100648 | g3703076 | 5.00E-08 | putative terminase large subunit |
| 26 | 34279 | 25324 | 25890 | MCA100871 | g3192703 | 6.00E-26 | gp20 |
| 26 | 34279 | 7772 | 8620 | MCA101290 | g1574365 | 5.00E-78 | H. influenzae predicted coding region HI1523 |
| 26 | 34279 | 8726 | 8929 | MCA101291 | | | |
| 26 | 34279 | 8996 | 9613 | MCA101292 | | | |
| 26 | 34279 | 11030 | 11218 | MCA101295 | | | |
| 26 | 34279 | 11362 | 12360 | MCA101296 | g4126611 | 2.00E-21 | ORF25 |
| 26 | 34279 | 12828 | 13169 | MCA101297 | | | |
| 26 | 34279 | 13153 | 13626 | MCA101299 | | | |
| 26 | 34279 | 13623 | 13979 | MCA101300 | | | |
| 26 | 34279 | 14007 | 14438 | MCA101301 | | | |
| 26 | 34279 | 14521 | 14868 | MCA101302 | | | |
| 26 | 34279 | 14943 | 15191 | MCA101303 | | | |
| 26 | 34279 | 15247 | 15624 | MCA101304 | | | |
| 26 | 34279 | 15733 | 19257 | MCA101305 | g2392838 | 2.00E-07 | unknown |
| 26 | 34279 | 19350 | 19622 | MCA101306 | g2232363 | 2.00E-09 | lambda phage M tail component homolog |
| 26 | 34279 | 22634 | 23014 | MCA101309 | | | |
| 26 | 34279 | 23069 | 23783 | MCA101409 | g3192701 | 1.00E-44 | gp18 |
| 26 | 34279 | 4281 | 4589 | MCA101760 | | | |
| 26 | 34279 | 5384 | 5770 | MCA101762 | | | |
| 26 | 34279 | 30917 | 31486 | MCA101785 | | | |
| 26 | 34279 | 12525 | 12812 | MCA101793 | | | |
| 26 | 34279 | 10141 | 10902 | MCA101809 | g3172264 | 4.00E-12 | major head subunit; gp17 |
| 26 | 34279 | 21575 | 22135 | MCA101932 | | | |
| 26 | 34279 | 22098 | 22577 | MCA101933 | | | |
| 26 | 34279 | 7432 | 7626 | MCA101935 | | | |
| 26 | 34279 | 5227 | 5397 | MCA102035 | | | |
| 27 | 48328 | 3898 | 4593 | MCA100056 | | | |
| 27 | 48328 | 23080 | 24003 | MCA100073 | g3482882 | 2.00E-81 | unknown |
| 27 | 48328 | 1179 | 1733 | MCA100106 | | | |
| 27 | 48328 | 1882 | 2790 | MCA100107 | | | |
| 27 | 48328 | 43439 | 45661 | MCA100173 | g1786239 | 3.00E-52 | organic solvent tolerance |
| 27 | 48328 | 18470 | 18898 | MCA100206 | g2314029 | 3.00E-33 | conserved hypothetical protein |
| 27 | 48328 | 18957 | 19259 | MCA100207 | g3228385 | 1.00E-10 | DsrC |
| 27 | 48328 | 19608 | 19982 | MCA100208 | g606279 | 7.00E-14 | ORF_f128 |
| 27 | 48328 | 20280 | 22904 | MCA100209 | g1789433 | e-171 | adenylylating enzyme for glutamine synthetase |
| 27 | 48328 | 39728 | 40198 | MCA100292 | g41611 | 3.00E-53 | GreA protein |
| 27 | 48328 | 40220 | 40582 | MCA100293 | | | |
| 27 | 48328 | 40907 | 41812 | MCA100294 | g440377 | 8.00E-14 | 297 amino acids peptide, unknown function |
| 27 | 48328 | 41954 | 43224 | MCA100295 | g1786238 | 1.00E-28 | survival protein |
| 27 | 48328 | 13080 | 13841 | MCA100296 | g3192702 | 4.00E-33 | gp19 |
| 27 | 48328 | 13845 | 14246 | MCA100297 | g1046241 | 5.00E-30 | orf14 |
| 27 | 48328 | 15183 | 16646 | MCA100300 | g3192704 | e-126 | gp21 |
| 27 | 48328 | 9361 | 10777 | MCA100325 | g3192699 | 8.00E-13 | gp16 |
| 27 | 48328 | 17057 | 18226 | MCA100681 | g3294478 | 6.00E-74 | putative integrase |
| 27 | 48328 | 5343 | 5990 | MCA100784 | g15640 | 5.00E-36 | antirepressor protein gene (aa 1-300) |
| 27 | 48328 | 7640 | 9283 | MCA100788 | g2764873 | 9.00E-27 | gene 18.1 |
| 27 | 48328 | 10904 | 11236 | MCA100790 | | | |
| 27 | 48328 | 11341 | 11730 | MCA100791 | | | |
| 27 | 48328 | 11814 | 12479 | MCA100792 | g3192701 | 4.00E-32 | gp18 |
| 27 | 48328 | 24782 | 25846 | MCA101267 | g2105065 | 8.00E-71 | hypothetical protein Rv3629c |
| 27 | 48328 | 25926 | 26549 | MCA101268 | g3406829 | 5.00E-40 | glutathione-S-transferase homolog |

TABLE 1-continued

| Contig | Size | Start | End | Locus ID | Identifier | P-value | Description |
|---|---|---|---|---|---|---|---|
| 27 | 48328 | 26714 | 28057 | MCA101269 | g1789768 | 2.00E-93 | uroporphyrinogen III methylase; sirohaeme biosynthesis |
| 27 | 48328 | 28527 | 30197 | MCA101270 | g2565334 | e-175 | sulfite reductase |
| 27 | 48328 | 30403 | 31599 | MCA101271 | g1799660 | e-141 | aspartate aminotransferase (EC 2.6.1.1) |
| 27 | 48328 | 32136 | 32504 | MCA101273 | g1788077 | 1.00E-27 | orf, hypothetical protein |
| 27 | 48328 | 32871 | 34085 | MCA101274 | g451651 | e-139 | carbamoyl phosphate synthetase light subunit |
| 27 | 48328 | 34231 | 35126 | MCA101275 | g1781074 | 2.00E-41 | mrr |
| 27 | 48328 | 35218 | 35517 | MCA101276 | | | |
| 27 | 48328 | 35648 | 36154 | MCA101277 | g1573288 | 3.00E-39 | conserved hypothetical protein |
| 27 | 48328 | 36212 | 39451 | MCA101278 | g1750387 | 0 | carbamoylphosphate synthetase large subunit |
| 27 | 48328 | 1690 | 1878 | MCA101315 | | | |
| 27 | 48328 | 46479 | 47453 | MCA101401 | g4545243 | 3.00E-43 | unknown |
| 27 | 48328 | 14561 | 15130 | MCA101644 | g3192703 | 1.00E-17 | gp20 |
| 27 | 48328 | 47519 | 48194 | MCA101706 | g4545244 | 4.00E-34 | unknown |
| 27 | 48328 | 6600 | 6881 | MCA101849 | | | |
| 27 | 48328 | 3071 | 3532 | MCA101900 | | | |
| 27 | 48328 | 3625 | 3816 | MCA101901 | | | |
| 27 | 48328 | 2 | 349 | MCA101902 | | | |
| 28 | 49617 | 33195 | 34376 | MCA100162 | g1573560 | e-173 | elongation factor Tu (tufA) |
| 28 | 49617 | 34523 | 35461 | MCA100163 | g1787114 | e-103 | thioredoxin reductase |
| 28 | 49617 | 29820 | 30191 | MCA100230 | g148985 | 3.00E-59 | StrA |
| 28 | 49617 | 30315 | 30785 | MCA100231 | g1573568 | 6.00E-60 | ribosomal protein S7 (rpS7) |
| 28 | 49617 | 30948 | 33044 | MCA100232 | g41517 | 0 | elongation factor G |
| 28 | 49617 | 762 | 1895 | MCA100242 | g164759 | 9.00E-17 | alanine:glyoxylate aminotransferase |
| 28 | 49617 | 2047 | 3519 | MCA100244 | g1573675 | e-137 | aminoacyl-histidine dipeptidase (pepD) |
| 28 | 49617 | 3619 | 4347 | MCA100245 | g746513 | 2.00E-23 | D1022.4 |
| 28 | 49617 | 35607 | 36643 | MCA100342 | g3172117 | 5.00E-84 | acyl-CoA dehydrogenase |
| 28 | 49617 | 36644 | 37420 | MCA100343 | g2909448 | 3.00E-31 | fadE5 |
| 28 | 49617 | 37843 | 38634 | MCA100344 | g1785900 | 6.00E-30 | shikimate dehydrogenase |
| 28 | 49617 | 38747 | 39349 | MCA100345 | | | |
| 28 | 49617 | 39350 | 40180 | MCA100346 | g1651539 | 4.00E-07 | 4-amino-4-deoxychorismate lyase. |
| 28 | 49617 | 14395 | 17115 | MCA100440 | g3414697 | 0 | lactoferrin binding protein B; LbpB |
| 28 | 49617 | 22514 | 23227 | MCA100449 | g3414695 | e-135 | unknown |
| 28 | 49617 | 40373 | 41422 | MCA100670 | g1573431 | 3.00E-63 | conserved hypothetical protein |
| 28 | 49617 | 41438 | 42034 | MCA100671 | g3328593 | 2.00E-29 | Thymidylate Kinase |
| 28 | 49617 | 42254 | 43129 | MCA100672 | g1573221 | 4.00E-76 | dihydrodipicolinate synthetase (dapA) |
| 28 | 49617 | 43531 | 44238 | MCA100673 | g1788820 | 1.00E-80 | phosphoribosylamino-imidazolesuccinocarbox-amide synthetase |
| 28 | 49617 | 44287 | 44583 | MCA100674 | g1261932 | 2.00E-22 | hypothetical protein Rv2230c |
| 28 | 49617 | 44964 | 46457 | MCA100675 | g38754 | e-161 | anthranilate synthase |
| 28 | 49617 | 47871 | 48461 | MCA100677 | g1420585 | 9.00E-23 | ORF YOR259c |
| 28 | 49617 | 4561 | 4887 | MCA100806 | g4062758 | 6.00E-28 | Hypothetical protein HI1355 |
| 28 | 49617 | 5171 | 5995 | MCA100807 | g1778577 | 5.00E-38 | similar to H. influenzae |
| 28 | 49617 | 7002 | 7334 | MCA100810 | g536952 | 1.00E-32 | phnA gene product |
| 28 | 49617 | 7401 | 8669 | MCA100811 | g557262 | e-141 | glutamate 1-semialdehyde 2,1-aminomutase |
| 28 | 49617 | 8987 | 11776 | MCA100812 | g1786287 | 0 | preprotein translocase; secretion protein |
| 28 | 49617 | 11952 | 12248 | MCA100813 | | | |
| 28 | 49617 | 12453 | 13913 | MCA100961 | g4033729 | 2.00E-92 | apolipoprotein N-acyltransferase |
| 28 | 49617 | 17302 | 20301 | MCA101127 | g3414688 | 0 | lactoferrin binding protein A; LbpA |

TABLE 1-continued

| Contig | Size | Start | End | Locus ID | Identifier | P-value | Description |
|---|---|---|---|---|---|---|---|
| 28 | 49617 | 22158 | 22340 | MCA101129 | | | |
| 28 | 49617 | 23390 | 24286 | MCA101130 | g3861035 | 4.00E-53 | unknown |
| 28 | 49617 | 24341 | 25198 | MCA101131 | g154231 | 2.00E-57 | p-aminobenzoate synthase component I |
| 28 | 49617 | 25891 | 27114 | MCA101133 | g2384564 | e-115 | beta-ketoacyl-ACP synthase I |
| 28 | 49617 | 43166 | 43477 | MCA101765 | | | |
| 28 | 49617 | 27638 | 28825 | MCA101786 | g3924824 | 3.00E-18 | cDNA ESTs D37429, D34381, yk370a12.5, and yk370a12.3 |
| 28 | 49617 | 20306 | 21928 | MCA101788 | g3414689 | 0 | unknown |
| 28 | 49617 | 6260 | 6820 | MCA101859 | g887848 | 3.00E-16 | ORF_o326 |
| 28 | 49617 | 237 | 524 | MCA101905 | | | |
| 29 | 66986 | 35441 | 38304 | MCA100016 | g154417 | 0 | DNA repair enzyme |
| 29 | 66986 | 59667 | 60365 | MCA100045 | g1770057 | 3.00E-25 | glutamate racemase |
| 29 | 66986 | 26527 | 27261 | MCA100088 | g551827 | 1.00E-50 | phosphatidylserine decarboxylase |
| 29 | 66986 | 62551 | 62976 | MCA100100 | g2621609 | 3.00E-35 | peptide methionine sulfoxide reductase |
| 29 | 66986 | 32810 | 33283 | MCA100164 | g1871177 | 1.00E-32 | unknown protein |
| 29 | 66986 | 32188 | 32637 | MCA100165 | g1790320 | 4.00E-29 | orf, hypothetical protein |
| 29 | 66986 | 31513 | 32049 | MCA100166 | g1574395 | 2.00E-41 | dethiobiotin synthase (bioD-2) |
| 29 | 66986 | 30641 | 31438 | MCA100167 | g1574396 | 2.00E-26 | biotin synthesis protein, putative |
| 29 | 66986 | 3760 | 4908 | MCA100170 | g150277 | e-144 | major anaerobically induced outer membrane protein |
| 29 | 66986 | 7578 | 8528 | MCA100196 | g1788007 | e-108 | phenylalanine tRNA synthetase, alpha-subunit |
| 29 | 66986 | 8587 | 10980 | MCA100197 | g1788006 | 0 | phenylalanine tRNA synthetase, beta-subunit |
| 29 | 66986 | 376 | 2616 | MCA100310 | g2584871 | 0 | nitric oxide reductase |
| 29 | 66986 | 63073 | 63813 | MCA100362 | g1573289 | 6.00E-48 | conserved hypothetical protein |
| 29 | 66986 | 63968 | 64921 | MCA100363 | g1736517 | 2.00E-86 | ORF_ID:o337#12; similar to [P44167] |
| 29 | 66986 | 65011 | 65925 | MCA100364 | g1788268 | 2.00E-60 | orf, hypothetical protein |
| 29 | 66986 | 27579 | 27932 | MCA100376 | g1773150 | 3.00E-10 | hypothetical 14.8 kd protein |
| 29 | 66986 | 28126 | 29346 | MCA100377 | g1574398 | e-134 | adenosylmethionine-8-amino-7-oxononanoate aminotransfer |
| 29 | 66986 | 29451 | 30593 | MCA100378 | g1574397 | 3.00E-94 | 8-amino-7-oxononanoate synthase (bioF) |
| 29 | 66986 | 38453 | 38947 | MCA100569 | g1573216 | 3.00E-41 | single-stranded DNA binding protein (ssb) |
| 29 | 66986 | 41258 | 41935 | MCA100572 | g1067166 | 3.00E-67 | inner membrane protein |
| 29 | 66986 | 6768 | 7145 | MCA100655 | g2983502 | 3.00E-12 | hypothetical protein |
| 29 | 66986 | 56916 | 58574 | MCA100693 | g1842057 | 0 | electron transfer flavoprotein-ubiquinone oxidoreductase |
| 29 | 66986 | 55454 | 56770 | MCA100694 | g1787461 | 5.00E-88 | enzyme in alternate path of synthesis of 5-aminolevulin |
| 29 | 66986 | 53509 | 54726 | MCA100696 | g557259 | 1.00E-18 | orf3 |
| 29 | 66986 | 5678 | 6376 | MCA100697 | g1806180 | 4.00E-13 | hypothetical protein Rv0712 |
| 29 | 66986 | 52515 | 52949 | MCA100698 | g557258 | 3.00E-09 | hemM |
| 29 | 66986 | 51719 | 52480 | MCA100699 | g968927 | 9.00E-37 | orfY gene product |
| 29 | 66986 | 50111 | 51057 | MCA100701 | g147379 | e-122 | phosphoribosylpyrophosphate synthetase (EC 2.7.6.1) |
| 29 | 66986 | 49534 | 50058 | MCA100957 | g4062631 | 1.00E-11 | Cytochrome b561 |
| 29 | 66986 | 23587 | 25704 | MCA100973 | g939724 | 2.00E-99 | putative sensor kinase; regulatory protein |
| 29 | 66986 | 21832 | 22698 | MCA100974 | g581757 | e-110 | cysteine synthase |
| 29 | 66986 | 21122 | 21790 | MCA100975 | g4155184 | 9.00E-19 | putative |
| 29 | 66986 | 19031 | 20455 | MCA100977 | g1789148 | 5.00E-69 | putative enzyme |
| 29 | 66986 | 17277 | 18389 | MCA100979 | g1573195 | 1.00E-82 | ATP-dependent RNA helicase (deaD) |

TABLE 1-continued

| Contig | Size | Start | End | Locus ID | Identifier | P-value | Description |
|---|---|---|---|---|---|---|---|
| 29 | 66986 | 14191 | 16212 | MCA100981 | g1789147 | e-144 | (p)ppGpp synthetase I (GTP pyrophosphokinase) |
| 29 | 66986 | 13280 | 14149 | MCA100982 | g466773 | 2.00E-57 | formamidopyrimidine-DNA glycosylase |
| 29 | 66986 | 11637 | 11894 | MCA100984 | g1657496 | 1.00E-21 | hypothetical protein |
| 29 | 66986 | 61385 | 62110 | MCA101336 | g3132253 | 1.00E-33 | ORF5 |
| 29 | 66986 | 11131 | 11412 | MCA101783 | g1435199 | 3.00E-26 | IhfA |
| 29 | 66986 | 49142 | 49360 | MCA101787 | | | |
| 29 | 66986 | 60620 | 60838 | MCA101791 | | | |
| 29 | 66986 | 41962 | 42651 | MCA101800 | g1174236 | 8.00E-30 | CycJ |
| 29 | 66986 | 47425 | 48129 | MCA101884 | g467327 | 9.00E-49 | unknown |
| 29 | 66986 | 33583 | 33888 | MCA101885 | g1196481 | 4.00E-10 | unknown protein |
| 29 | 66986 | 34239 | 34529 | MCA101888 | g1778554 | 3.00E-20 | HI0034 homolog |
| 29 | 66986 | 34824 | 35239 | MCA101893 | g1303791 | 7.00E-15 | YqeJ |
| 29 | 66986 | 2840 | 3361 | MCA101894 | g2633273 | 1.00E-30 | similar to hypothetical proteins |
| 29 | 66986 | 39252 | 40400 | MCA101895 | g1789416 | 7.00E-91 | putative synthetase/amidase |
| 29 | 66986 | 42814 | 43641 | MCA101896 | g150508 | e-103 | lipoprotein |
| 29 | 66986 | 43836 | 44480 | MCA101897 | g1552774 | 1.00E-37 | hypothetical |
| 29 | 66986 | 44515 | 45558 | MCA101898 | g1573615 | e-121 | ABC transporter, ATP-binding protein |
| 29 | 66986 | 45781 | 46777 | MCA101899 | g2072712 | 9.00E-14 | mtrB |
| 29 | 66986 | 58939 | 59568 | MCA102050 | | | |
| 29 | 66986 | 20802 | 21026 | MCA102051 | | | |
| 29 | 66986 | 12225 | 13193 | MCA102055 | | | |
| 30 | 58909 | 57032 | 58390 | MCA100109 | g4062412 | e-165 | Hypothet. 51.7 kd protein in dnaJ-rpsU interegenic region. |
| 30 | 58909 | 44550 | 45806 | MCA100235 | g1799634 | 2.00E-97 | NADH dehydrogenase I chain N (EC 1.6.5.3) |
| 30 | 58909 | 47991 | 49715 | MCA100331 | g1574424 | 0 | arginyl-tRNA synthetase (argS) |
| 30 | 58909 | 46973 | 47773 | MCA100332 | g290446 | 4.00E-31 | ferredoxin NADP+ reductase |
| 30 | 58909 | 1064 | 2329 | MCA100463 | g436156 | e-127 | GTPase required for high frequency lysogenization |
| 30 | 58909 | 2502 | 3320 | MCA100464 | g606115 | 5.00E-55 | dihydropteroate synthase |
| 30 | 58909 | 3369 | 4094 | MCA100465 | g1789315 | 4.00E-34 | orf, hypothetical protein |
| 30 | 58909 | 56014 | 56754 | MCA100615 | g1183839 | 8.00E-73 | unknown |
| 30 | 58909 | 54292 | 55815 | MCA100616 | g148179 | e-131 | threonine deaminase |
| 30 | 58909 | 53064 | 54086 | MCA100617 | g44888 | e-153 | NgoPII restriction and modification |
| 30 | 58909 | 52624 | 53001 | MCA100618 | g606334 | 1.00E-30 | ORF_o133 |
| 30 | 58909 | 52190 | 52600 | MCA100619 | g1147812 | 1.00E-23 | red cell-type low molecular weight acid phosphatase |
| 30 | 58909 | 51008 | 52030 | MCA100620 | g145431 | 4.00E-49 | unidentified reading frame II |
| 30 | 58909 | 4392 | 5996 | MCA100757 | g44839 | e-139 | pilB gene product (AA 1-521) |
| 30 | 58909 | 45970 | 46683 | MCA100785 | g1573561 | 5.00E-96 | membrane protein |
| 30 | 58909 | 6 | 854 | MCA100838 | g1573723 | 7.00E-63 | heat shock protein (htpX) |
| 30 | 58909 | 39210 | 39746 | MCA101072 | g1788617 | 2.00E-81 | NADH dehydrogenase I chain I |
| 30 | 58909 | 39794 | 40300 | MCA101079 | g1788616 | 2.00E-32 | NADH dehydrogenase I chain J |
| 30 | 58909 | 6340 | 7718 | MCA101157 | g2804454 | e-131 | *C. elegans* adenosylhomocysteinase (SW:P27604) |
| 30 | 58909 | 8333 | 11554 | MCA101159 | g3523135 | 0 | transferrin binding protein A; TbpA |
| 30 | 58909 | 12590 | 14125 | MCA101161 | g3523128 | 0 | unknown |
| 30 | 58909 | 14403 | 16520 | MCA101164 | g3523129 | 0 | transferrin binding protein B; TbpB |
| 30 | 58909 | 17432 | 18442 | MCA101166 | g1590923 | 8.00E-21 | conserved hypothetical protein |
| 30 | 58909 | 18722 | 19336 | MCA101167 | g3861219 | 9.00E-47 | unknown |
| 30 | 58909 | 19375 | 20268 | MCA101168 | g1651962 | 3.00E-80 | hypothetical protein |
| 30 | 58909 | 22343 | 23683 | MCA101170 | g1574303 | e-128 | mrsA protein (mrsA) |
| 30 | 58909 | 23858 | 24490 | MCA101194 | g1653389 | 9.00E-50 | pyridoxamine 5-phosphate oxidase |

TABLE 1-continued

| Contig | Size | Start | End | Locus ID | Identifier | P-value | Description |
|---|---|---|---|---|---|---|---|
| 30 | 58909 | 24814 | 25410 | MCA101195 | g4063381 | 3.00E-27 | periplasmic chaperone protein |
| 30 | 58909 | 25438 | 25635 | MCA101196 | g1573260 | 3.00E-08 | mercuric ion scavenger protein (merP) |
| 30 | 58909 | 25824 | 26192 | MCA101197 | g3273735 | 2.00E-32 | NADH dehydrogenase chain A |
| 30 | 58909 | 26785 | 27447 | MCA101199 | g1788624 | 6.00E-87 | NADH dehydrogenase I chain B |
| 30 | 58909 | 27619 | 29301 | MCA101200 | g1788622 | 0 | NADH dehydrogenase I chain C, D |
| 30 | 58909 | 30568 | 31590 | MCA101202 | g682765 | 3.00E-74 | mccB |
| 30 | 58909 | 31965 | 32180 | MCA101203 | g349635 | 2.00E-19 | NADH dehydrogenase subunit |
| 30 | 58909 | 33192 | 33647 | MCA101205 | g349636 | 3.00E-46 | NADH dehydrogenase subunit |
| 30 | 58909 | 33770 | 35029 | MCA101206 | g1799645 | e-152 | NADH dehydrogenase I chain F (EC 1.6.5.3) |
| 30 | 58909 | 35070 | 38009 | MCA101207 | g409013 | 0 | NADH dehydrogenase subunit |
| 30 | 58909 | 38202 | 39188 | MCA101208 | g1788618 | e-123 | NADH dehydrogenase I chain H |
| 30 | 58909 | 40440 | 40736 | MCA101211 | g1799639 | 4.00E-22 | NADH dehydrogenase I chain K (EC 1.6.5.3) |
| 30 | 58909 | 40746 | 42596 | MCA101212 | g1788614 | 0 | NADH dehydrogenase I chain L |
| 30 | 58909 | 42622 | 44157 | MCA101213 | g1799637 | e-148 | NADH dehydrogenase chain 4 (EC 1.6.5.3) |
| 30 | 58909 | 32262 | 33029 | MCA101966 | | | |
| 31 | 65792 | 57101 | 58057 | MCA100214 | g1236631 | 2.00E-69 | SfhB |
| 31 | 65792 | 58173 | 58838 | MCA100215 | g2104329 | 5.00E-19 | yfiH |
| 31 | 65792 | 58955 | 59695 | MCA100216 | g1573058 | 1.00E-62 | conserved hypothetical protein |
| 31 | 65792 | 31449 | 32228 | MCA100281 | g4008034 | 3.00E-82 | enoyl-(acyl-carrier protein) reductase |
| 31 | 65792 | 32373 | 33071 | MCA100282 | g1573553 | 3.00E-91 | ribulose-phosphate 3-epimerase (dod) |
| 31 | 65792 | 33430 | 33732 | MCA100283 | | | |
| 31 | 65792 | 33788 | 34507 | MCA100284 | | | |
| 31 | 65792 | 34613 | 35137 | MCA100286 | g2959334 | 8.00E-17 | hypothetical protein |
| 31 | 65792 | 44547 | 46088 | MCA100350 | g1790041 | e-153 | 2,3-bisphosphoglycerate-indpndnt phosphoglycerate mutase |
| 31 | 65792 | 46329 | 47333 | MCA100351 | g2983365 | 2.00E-42 | carboxyl-terminal protease |
| 31 | 65792 | 59939 | 62041 | MCA100406 | g1573258 | e-178 | potassium/copper-transporting ATPase, putative |
| 31 | 65792 | 62189 | 62968 | MCA100407 | | | |
| 31 | 65792 | 63137 | 63424 | MCA100408 | g1787108 | 7.00E-14 | orf, hypothetical protein |
| 31 | 65792 | 63494 | 65749 | MCA100409 | g45972 | 0 | URF 2 |
| 31 | 65792 | 342 | 1250 | MCA100493 | g1787799 | 6.00E-40 | orf, hypothetical protein |
| 31 | 65792 | 5366 | 7711 | MCA100687 | g42481 | 0 | pyruvate, water dikinase |
| 31 | 65792 | 8122 | 8934 | MCA100688 | g1001627 | 5.00E-16 | hypothetical protein |
| 31 | 65792 | 9194 | 11455 | MCA100689 | g4062515 | e-117 | Hypothetical protein HI0115 |
| 31 | 65792 | 12030 | 12881 | MCA100691 | g1787606 | 5.00E-96 | orf, hypothetical protein |
| 31 | 65792 | 35380 | 36765 | MCA100702 | g4155857 | e-162 | fumerase |
| 31 | 65792 | 37101 | 40302 | MCA100703 | g3928723 | 4.00E-77 | putative ABC transporter |
| 31 | 65792 | 41558 | 41968 | MCA100706 | g4154631 | 1.00E-26 | bacterioferritin comigratory protein |
| 31 | 65792 | 42310 | 43617 | MCA100707 | g1573080 | 0 | conserved hypothetical protein |
| 31 | 65792 | 13827 | 14018 | MCA100733 | g1778825 | 7-00E-21 | major cold shock protein CspA |
| 31 | 65792 | 33077 | 33430 | MCA100775 | | | |
| 31 | 65792 | 47450 | 48073 | MCA100793 | g3142729 | 2.00E-62 | response regulator |
| 31 | 65792 | 48273 | 48530 | MCA100794 | g2632000 | 3.00E-22 | RpsT protein |
| 31 | 65792 | 48820 | 49518 | MCA100795 | g1203935 | 7.00E-08 | coded for by C. elegans cDNA yk86b10.5 |

TABLE 1-continued

| Contig | Size | Start | End | Locus ID | Identifier | P-value | Description |
|---|---|---|---|---|---|---|---|
| 31 | 65792 | 49766 | 52474 | MCA100796 | g525202 | 0 | DNA topoisomerase (ATP-hydrolysing) |
| 31 | 65792 | 52499 | 53179 | MCA100797 | g557844 | 5.00E-19 | orf, len: 234, CAI: 0.26 |
| 31 | 65792 | 53919 | 55553 | MCA100799 | g882589 | 4.00E-61 | CG Site No. 847; alternate gen name dnaP, parB |
| 31 | 65792 | 55986 | 56600 | MCA100800 | g1573134 | 6.00E-31 | lipoprotein, putative |
| 31 | 65792 | 30651 | 31190 | MCA100907 | g2981082 | 1.00E-51 | GTP-cyclohydrolase |
| 31 | 65792 | 28838 | 30289 | MCA100908 | g4062623 | 5.00E-91 | Novobiocin resistance-related protein Nov |
| 31 | 65792 | 27100 | 28536 | MCA100909 | g2894397 | 6.00E-25 | TphA protein |
| 31 | 65792 | 26354 | 26986 | MCA100911 | g2708657 | 3.00E-57 | ribose-5-phosphate isomerase |
| 31 | 65792 | 25195 | 26139 | MCA100912 | g1787100 | 3.00E-43 | putative surface protein |
| 31 | 65792 | 23910 | 25004 | MCA100913 | g1789273 | 4.00E-39 | orf, hypothetical protein |
| 31 | 65792 | 22262 | 23656 | MCA100914 | g142309 | e-179 | glutamine synthetase |
| 31 | 65792 | 53226 | 53429 | MCA101798 | | | |
| 31 | 65792 | 21511 | 21816 | MCA101835 | | | |
| 31 | 65792 | 17390 | 18373 | MCA101836 | g1653422 | 2.00E-06 | hypothetical protein |
| 31 | 65792 | 20955 | 21458 | MCA101838 | | | |
| 31 | 65792 | 1604 | 2059 | MCA101861 | g2688497 | 7.00E-13 | carboxypeptidase, putative |
| 31 | 65792 | 2444 | 3820 | MCA101862 | g1907384 | e-160 | soluble pyridine nucleotide transhydrogenase |
| 31 | 65792 | 4190 | 4996 | MCA101866 | g1787995 | 2.00E-61 | orf, hypothetical protein |
| 31 | 65792 | 14240 | 16021 | MCA101867 | g1651441 | e-107 | MsbA protein. |
| 31 | 65792 | 18490 | 19170 | MCA101868 | g561691 | 5.00E-40 | LpsA |
| 31 | 65792 | 19197 | 19931 | MCA101873 | g1573652 | 1.00E-55 | lipopolysaccharide biosynthesis protein |
| 31 | 65792 | 19998 | 20750 | MCA101874 | g1573652 | 4.00E-56 | lipopolysaccharide biosynthesis protein |
| 31 | 65792 | 13103 | 13522 | MCA101875 | g3062 | 4.00E-41 | 3-dehydroquinate dehydratase |
| 32 | 62909 | 50745 | 52567 | MCA100340 | g2623969 | 2.00E-56 | putative peptidyl-prolyl cis-trans isomerase |
| 32 | 62909 | 49000 | 50580 | MCA100341 | g42595 | 0 | purH gene product |
| 32 | 62909 | 42928 | 48531 | MCA100348 | g1666683 | 1.00E-45 | hsf gene product |
| 32 | 62909 | 8351 | 8881 | MCA100498 | g1574570 | 2.00E-61 | conserved hypothetical protein |
| 32 | 62909 | 10103 | 11257 | MCA100501 | g1789311 | e-157 | methionine adenosyltransferase 1 |
| 32 | 62909 | 11895 | 12551 | MCA100503 | g4062689 | 1.00E-56 | heterocyst maturation protein (devA) homolog |
| 32 | 62909 | 12581 | 13813 | MCA100504 | g1787362 | 2.00E-62 | putative kinase |
| 32 | 62909 | 6566 | 7315 | MCA100649 | g1773205 | 2.00E-22 | similar to *H. influenzae* HI0735 |
| 32 | 62909 | 6025 | 6510 | MCA100650 | g1786736 | 1.00E-52 | peptidyl-prolyl cis-trans isomerase B (rotamase B) |
| 32 | 62909 | 4072 | 5826 | MCA100651 | g1574816 | e-175 | glutaminyl-tRNA synthetase (glnS) |
| 32 | 62909 | 2634 | 3977 | MCA100652 | g3850110 | 3.00E-60 | rrm3-pif1 helicase homolog |
| 32 | 62909 | 1016 | 2038 | MCA100654 | g39921 | 3.00E-75 | glyceraldehyde-3-phosphate dehydrogenase (AA 1 - 335) |
| 32 | 62909 | 54353 | 54796 | MCA100831 | g1573349 | 3.00E-38 | conserved hypothetical protein |
| 32 | 62909 | 54874 | 56076 | MCA100832 | g1788879 | e-169 | putative aminotransferase |
| 32 | 62909 | 56256 | 56636 | MCA100833 | g1788878 | 3.00E-55 | orf, hypothetical protein |
| 32 | 62909 | 56752 | 57066 | MCA100834 | g1573345 | 2.00E-30 | conserved hypothetical protein |
| 32 | 62909 | 57767 | 59620 | MCA100836 | g1573342 | e-135 | heat shock protein (hscA) |
| 32 | 62909 | 59732 | 60067 | MCA100837 | g3925514 | 6.00E-39 | ferredoxin |
| 32 | 62909 | 60693 | 62453 | MCA100839 | g3261657 | 3.00E-97 | ggtB |
| 32 | 62909 | 57114 | 57557 | MCA100980 | g1799935 | 4.00E-17 | similar to [P36540] |
| 32 | 62909 | 14126 | 14635 | MCA101066 | | | |

TABLE 1-continued

| Contig | Size | Start | End | Locus ID | Identifier | P-value | Description |
|---|---|---|---|---|---|---|---|
| 32 | 62909 | 17539 | 17940 | MCA101071 | g2114470 | 5.00E-46 | transposase homolog A |
| 32 | 62909 | 21605 | 22480 | MCA101075 | g1788819 | 2.00E-68 | orf, hypothetical protein |
| 32 | 62909 | 22570 | 23385 | MCA101076 | g1001366 | 7.00E-39 | hypothetical protein |
| 32 | 62909 | 26086 | 26817 | MCA101080 | g2367307 | 7.00E-95 | |
| 32 | 62909 | 27509 | 29122 | MCA101082 | g2367309 | 5.00E-89 | orf, hypothetical protein |
| 32 | 62909 | 29170 | 29628 | MCA101083 | g1653085 | 8.00E-26 | adenine phosphoribosyltransferase |
| 32 | 62909 | 53480 | 54157 | MCA101204 | | | |
| 32 | 62909 | 31514 | 32173 | MCA101329 | g1110441 | 2.00E-27 | hypothetical product |
| 32 | 62909 | 32281 | 34587 | MCA101330 | g290642 | 2.00E-80 | ATPase |
| 32 | 62909 | 35413 | 37533 | MCA101332 | g1574581 | e-127 | penicillin-binding protein 1B (ponB) |
| 32 | 62909 | 40898 | 41815 | MCA101337 | g2367208 | 1.00E-56 | methylase for 50S ribosomal subunit protein L11 |
| 32 | 62909 | 41865 | 42068 | MCA101338 | g2773316 | 2.00E-12 | small DNA binding protein L11 |
| 32 | 62909 | 62692 | 62907 | MCA101380 | g2407233 | 5.00E-23 | similar to *Haemophilus influenzae* U32796 |
| 32 | 62909 | 52735 | 53004 | MCA101444 | g535709 | 5.00E-26 | HU protein |
| 32 | 62909 | 19635 | 20612 | MCA101773 | | | |
| 32 | 62909 | 26826 | 27470 | MCA101776 | | | |
| 32 | 62909 | 29954 | 30133 | MCA101904 | g1788076 | 5.00E-10 | orf, hypothetical protein |
| 32 | 62909 | 30170 | 31093 | MCA101910 | g1800020 | 1.00E-54 | similar to [P37768] |
| 32 | 62909 | 39861 | 40532 | MCA101911 | g48895 | 9.00E-10 | acid phosphatase |
| 32 | 62909 | 15209 | 16036 | MCA101913 | g2649017 | 2.00E-16 | conserved hypothetical protein |
| 32 | 62909 | 16414 | 17027 | MCA101914 | g1652952 | 5.00E-30 | transposase |
| 32 | 62909 | 20712 | 21326 | MCA101917 | g244501 | 5.00E-42 | esterase II = carboxylesterase {EC 3.1.1.1} |
| 32 | 62909 | 24945 | 25550 | MCA101919 | g2407235 | 3.00E-81 | manganese superoxide dismutase |
| 32 | 62909 | 9114 | 9776 | MCA102048 | g1001410 | 1.00E-07 | hypothetical protein |
| 32 | 62909 | 11483 | 11827 | MCA102049 | | | |
| 33 | 63563 | 62405 | 62632 | MCA101035 | g2314031 | 5.00E-10 | conserved hypothetical protein |
| 33 | 63563 | 56948 | 58870 | MCA101040 | g2623258 | 4.00E-45 | putative secreted protein |
| 33 | 63563 | 21766 | 23691 | MCA101136 | g2765451 | 8.00E-61 | nitrate/nitrite sensory protein |
| 33 | 63563 | 3 | 827 | MCA101560 | g2098763 | 7.00E-67 | ThiI |
| 33 | 63563 | 31681 | 31896 | MCA101587 | g39312 | 3.00E-08 | barstar (AA 1 - 90) |
| 33 | 63563 | 1409 | 2644 | MCA101680 | g1684734 | 3.00E-41 | ORF396 protein |
| 33 | 63563 | 3749 | 4354 | MCA101682 | g1786318 | 2.00E-61 | putative carbonic anhdrase (EC 4.2.1.1) |
| 33 | 63563 | 4569 | 8282 | MCA101683 | g1911243 | 0 | alpha-subunit of nitrate reductase |
| 33 | 63563 | 8347 | 9879 | MCA101684 | g2765455 | 0 | respiratory nitrate reductase beta subunit |
| 33 | 63563 | 9907 | 10644 | MCA101685 | g2765456 | 1.00E-40 | putative chaperone |
| 33 | 63563 | 10719 | 11384 | MCA101686 | g2765457 | 2.00E-63 | respiratory nitrate reductase gamma subunit |
| 33 | 63563 | 11872 | 12597 | MCA101688 | g2765458 | 6.00E-39 | NifM protein |
| 33 | 63563 | 12741 | 13922 | MCA101689 | g1574287 | 9.00E-70 | molybdopterin biosynthesis protein (moeA) |
| 33 | 63563 | 13931 | 15273 | MCA101690 | g1574545 | 4.00E-46 | molybdenum ABC transporter, permease protein (modB) |
| 33 | 63563 | 15349 | 16047 | MCA101691 | g973214 | 2.00E-49 | ModA |
| 33 | 63563 | 16157 | 16573 | MCA101692 | g899221 | 1.00E-26 | potential molybdenum-pterin-binding-protein |
| 33 | 63563 | 16659 | 17036 | MCA101693 | g1001213 | 1.00E-26 | molybdopterin (MPT) converting factor, subunit 2 |
| 33 | 63563 | 17122 | 17355 | MCA101694 | g1673309 | 1.00E-09 | hypothetical protein |
| 33 | 63563 | 17375 | 17827 | MCA101695 | g4185548 | 2.00E-27 | molybdenum cofactor biosynthesis protein C |
| 33 | 63563 | 18520 | 19008 | MCA101697 | g42009 | 2.00E-50 | moaB |
| 33 | 63563 | 19257 | 19745 | MCA101698 | g1790345 | 5.00E-20 | orf, hypothetical protein |

TABLE 1-continued

| Contig | Size | Start | End | Locus ID | Identifier | P-value | Description |
|---|---|---|---|---|---|---|---|
| 33 | 63563 | 19849 | 20817 | MCA101699 | g1574526 | 1.00E-73 | molybdenum cofactor biosynthesis protein A (moaA) |
| 33 | 63563 | 21099 | 21722 | MCA101700 | g2765450 | 1.00E-57 | nitrate/nitrite regulatory protein |
| 33 | 63563 | 24027 | 25301 | MCA101702 | g2765452 | e-100 | nitrate extrusion protein |
| 33 | 63563 | 25322 | 26662 | MCA101703 | g2765453 | e-131 | nitrate extrusion protein |
| 33 | 63563 | 26767 | 27003 | MCA101704 | g43593 | 7.00E-25 | IS1016-V6 |
| 33 | 63563 | 27101 | 27838 | MCA101705 | g1256835 | 2.00E-37 | moeB gene product |
| 33 | 63563 | 30824 | 31012 | MCA101707 | g39312 | 6.00E-08 | barstar (AA 1 - 90) |
| 33 | 63563 | 31908 | 32282 | MCA101708 | g532528 | 5.00E-15 | ribonuclease precursor |
| 33 | 63563 | 44513 | 44764 | MCA101912 | | | |
| 33 | 63563 | 59342 | 60850 | MCA101915 | g1772622 | 3.00E-30 | HecB |
| 33 | 63563 | 63286 | 63563 | MCA101916 | | | |
| 34 | 89047 | 54807 | 56590 | MCA100174 | g2984323 | 4.00E-67 | hypothetical protein |
| 34 | 89047 | 72751 | 73173 | MCA100188 | g1788522 | 2.00E-25 | possible subunit of heme lyase |
| 34 | 89047 | 64432 | 65214 | MCA100272 | g1799711 | 8.00E-72 | pseudouridylate synthase I (EC 4.2.1.70) |
| 34 | 89047 | 64078 | 64287 | MCA100273 | g142459 | 7.00E-25 | initiation factor 1 |
| 34 | 89047 | 16260 | 18866 | MCA100326 | g1651269 | 0 | Leucine-tRNA ligase (EC 6.1.1.4). |
| 34 | 89047 | 67834 | 68322 | MCA100327 | g1573775 | 6.00E-27 | conserved hypothetical protein |
| 34 | 89047 | 68604 | 69926 | MCA100329 | | | |
| 34 | 89047 | 70103 | 72067 | MCA100330 | g1174237 | e-175 | CycK |
| 34 | 89047 | 8218 | 9123 | MCA100410 | g1420863 | e-140 | oligopeptidepermease |
| 34 | 89047 | 9349 | 11319 | MCA100411 | g1420859 | 0 | oligopeptidepermease |
| 34 | 89047 | 11462 | 11734 | MCA100412 | g1817528 | 7.00E-13 | component protein of adhesin complex |
| 34 | 89047 | 12117 | 12434 | MCA100413 | g1817528 | 1.00E-14 | component protein of adhesin complex |
| 34 | 89047 | 31288 | 32337 | MCA100432 | g3212213 | e-120 | H. influenzae predicted coding region HI1126.1 |
| 34 | 89047 | 30886 | 31281 | MCA100623 | g3212214 | 8.00E-48 | H. influenzae predicted coding region HI1127 |
| 34 | 89047 | 3573 | 4214 | MCA100666 | g1573906 | 6.00E-96 | H. influenzae predicted coding region HI0882 |
| 34 | 89047 | 4621 | 6105 | MCA100667 | g1420860 | 0 | oligopeptidepermease |
| 34 | 89047 | 6109 | 7032 | MCA100668 | g1420861 | e-145 | oligopeptidepermease |
| 34 | 89047 | 7081 | 8115 | MCA100669 | g1420862 | e-163 | oligopeptidepermease |
| 34 | 89047 | 26541 | 28064 | MCA100734 | g2984319 | 2.00E-95 | Na(+):solute symporter (Ssf family) |
| 34 | 89047 | 24901 | 25710 | MCA100736 | g1513082 | 5.00E-67 | ATPase |
| 34 | 89047 | 23328 | 24365 | MCA100738 | g1786606 | 8.00E-89 | S-adenosylmethionine:tRNA ribosyltransferase-isomerase |
| 34 | 89047 | 22063 | 23202 | MCA100739 | g1573209 | e-147 | tRNA-guanine transglycosylase (tgt) |
| 34 | 89047 | 20280 | 21854 | MCA1G0740 | g536958 | 2.00E-74 | yjdB gene product |
| 34 | 89047 | 19010 | 19351 | MCA100742 | g1573052 | 7.00E-15 | conserved hypothetical protein |
| 34 | 89047 | 72176 | 72649 | MCA100857 | g929791 | 1.00E-22 | periplasmic or inner membrane associated protein |
| 34 | 89047 | 60817 | 61410 | MCA101043 | g312708 | 5.00E-41 | miaE |
| 34 | 89047 | 59356 | 60669 | MCA101044 | g1790609 | 8.00E-39 | orf, hypothetical protein |
| 34 | 89047 | 57906 | 58931 | MCA101045 | g1573704 | 7.00E-40 | conserved hypothetical protein |
| 34 | 89047 | 56828 | 57394 | MCA101047 | g3328430 | 3.00E-71 | Deoxycytidine triphosphate deaminase family protein |
| 34 | 89047 | 52985 | 53889 | MCA101051 | g2636549 | 2.00E-22 | similar to hypothetical proteins |
| 34 | 89047 | 51712 | 52935 | MCA101052 | g216628 | 4.00E-52 | UbiH (VisB) |
| 34 | 89047 | 50505 | 51353 | MCA101053 | g1787880 | 7.00E-32 | putative transport protein |
| 34 | 89047 | 48105 | 50117 | MCA101054 | g148182 | e-177 | rep helicase |
| 34 | 89047 | 46737 | 47753 | MCA101056 | g537005 | 4.00E-58 | ORF_f337 |

TABLE 1-continued

| Contig | Size | Start | End | Locus ID | Identifier | P-value | Description |
|---|---|---|---|---|---|---|---|
| 34 | 89047 | 74796 | 75440 | MCA101231 | g4520134 | 7.00E-73 | adenylate kinase |
| 34 | 89047 | 78867 | 80283 | MCA101233 | g3861163 | 9.00E-74 | 2-acylglycerophospho-ethanolamine acyltransferase |
| 34 | 89047 | 82080 | 83144 | MCA101235 | g1573700 | 1.00E-28 | conserved hypothetical protein |
| 34 | 89047 | 85493 | 88297 | MCA101238 | g1573699 | 2.00E-69 | conserved hypothetical protein |
| 34 | 89047 | 45297 | 45752 | MCA101341 | g1790038 | 3.00E-37 | protein export; molecular chaperone |
| 34 | 89047 | 44704 | 45165 | MCA101342 | g41300 | 4.00E-46 | dUTPase (dut) |
| 34 | 89047 | 44243 | 44665 | MCA101343 | g2984288 | 1.00E-33 | acetylglutamate kinase |
| 34 | 89047 | 43444 | 44199 | MCA101344 | g2462049 | 1.00E-14 | hypothetical protein |
| 34 | 89047 | 42700 | 43350 | MCA101345 | g1763619 | 6.00E-19 | potassium channel alpha subunit |
| 34 | 89047 | 39885 | 40328 | MCA101347 | g42848 | 6.00E-32 | ribosome protein L9 (aa 1-149) |
| 34 | 89047 | 39641 | 39865 | MCA101348 | g1573530 | 5.00E-29 | ribosomal protein S18 (rpS18) |
| 34 | 89047 | 39224 | 39610 | MCA101349 | g42845 | 2.00E-35 | ribosomal protein S6 (aa 1-131) |
| 34 | 89047 | 36447 | 37520 | MCA101351 | g1789272 | 1.00E-96 | tetrahydrofolate-dependent aminomethyltransferase |
| 34 | 89047 | 35751 | 36128 | MCA101352 | g1789271 | 8.00E-40 | carrier of aminomethyl moiety via lipoyl cofactor |
| 34 | 89047 | 32628 | 35462 | MCA101353 | g304892 | 0 | gcvHP |
| 34 | 89047 | 28777 | 30564 | MCA101356 | g3212231 | e-141 | TonB-dependent receptor, putative |
| 34 | 89047 | 73261 | 74523 | MCA101532 | | | |
| 34 | 89047 | 45820 | 46071 | MCA101632 | g3860768 | 7.00E-16 | glutaredoxin 3 |
| 34 | 89047 | 62090 | 63166 | MCA101727 | g1922276 | 2.00E-15 | porin |
| 34 | 89047 | 25927 | 26316 | MCA101860 | g4545096 | 5.00E-09 | unknown |
| 34 | 89047 | 38043 | 38363 | MCA101920 | g4062756 | 3.00E-08 | Hypothetical protein HI1446 |
| 34 | 89047 | 66384 | 67498 | MCA101922 | g1420975 | e-130 | aspartate semialdehyde dehydrogenase |
| 34 | 89047 | 57510 | 57803 | MCA102061 | | | |
| 34 | 89047 | 403 | 2859 | MCA102062 | g2983163 | 5.00E-07 | outer membrane protein c |
| 34 | 89047 | 3164 | 3520 | MCA102063 | | | |
| 34 | 89047 | 38496 | 38981 | MCA102068 | | | |
| 34 | 89047 | 13061 | 14095 | MCA102070 | g4456807 | 4.00E-07 | hypothetical protein |
| 34 | 89047 | 40804 | 41724 | MCA102072 | | | |
| 34 | 89047 | 41911 | 42456 | MCA102073 | g1790149 | 3.00E-12 | orf, hypothetical protein |
| 35 | 96109 | 63603 | 63740 | MCA100010 | g3603060 | 9.00E-11 | ribosomal protein L36 |
| 35 | 96109 | 63882 | 64673 | MCA100011 | g609333 | 6.00E-61 | orf272 |
| 35 | 96109 | 781 | 1275 | MCA100095 | g1789019 | 5.00E-25 | orf, hypothetical protein |
| 35 | 96109 | 31479 | 31784 | MCA100151 | g149064 | 4.00E-07 | insb (putative); putative |
| 35 | 96109 | 16679 | 17584 | MCA100238 | g1574277 | 9.00E-55 | geranyltranstransferase (ispA) |
| 35 | 96109 | 15484 | 16293 | MCA100239 | g146864 | 5.00E-60 | A/G-specific adenine glycosylase |
| 35 | 96109 | 14399 | 14971 | MCA100241 | g1314160 | 3.00E-20 | mitochondrial nuclease |
| 35 | 96109 | 330 | 551 | MCA100571 | g1173842 | 2.00E-20 | acyl carrier protein |
| 35 | 96109 | 91699 | 93600 | MCA100613 | g1574199 | 0 | threonyl-tRNA synthetase (thrS) |
| 35 | 96109 | 18008 | 18937 | MCA100723 | g1574400 | 3.00E-61 | 2-hydroxyacid dehydrogenase |
| 35 | 96109 | 19173 | 22007 | MCA100724 | g1786245 | 0 | probable ATP-dependent RNA helicase |
| 35 | 96109 | 23729 | 25783 | MCA100726 | g2695959 | 0 | fadH |
| 35 | 96109 | 64879 | 65883 | MCA10C851 | g2198496 | 2.00E-51 | B1306.06c protein |
| 35 | 96109 | 68453 | 68746 | MCA100854 | g144052 | 5.00E-18 | outer membrane protein A |
| 35 | 96109 | 69092 | 69673 | MCA100855 | g1573697 | 3.00E-46 | conserved hypothetical protein |
| 35 | 96109 | 69937 | 71532 | MCA100856 | g790611 | 9.00E-63 | unknown |
| 35 | 96109 | 72055 | 72594 | MCA100858 | g2160520 | 2.00E-32 | ORF1; similar to *E coli* L28082 |
| 35 | 96109 | 72778 | 73755 | MCA100859 | | | |

TABLE 1-continued

| Contig | Size | Start | End | Locus ID | Identifier | P-value | Description |
|---|---|---|---|---|---|---|---|
| 35 | 96109 | 73860 | 74870 | MCA100860 | g3257505 | 2.00E-32 | homocysteine S-methyltransferase |
| 35 | 96109 | 89648 | 90142 | MCA100884 | g290449 | 6.00E-45 | initiation factor 3 |
| 35 | 96109 | 86580 | 88901 | MCA100886 | g1790622 | e-148 | putative enzyme |
| 35 | 96109 | 83852 | 85201 | MCA100889 | g2558473 | e-124 | Na-translocating NADH-quinone reductase alpha-subunit |
| 35 | 96109 | 82641 | 83837 | MCA100890 | g1573123 | e-138 | NADH:ubiquinone oxidoreductase, subunit B (nqrB) |
| 35 | 96109 | 81848 | 82621 | MCA100891 | g2558475 | 2.00E-42 | Na-translocating NADH-quinone reductase gamma-subunit |
| 35 | 96109 | 81207 | 81806 | MCA100892 | g1573125 | 2.00E-71 | NADH:ubiquinone oxidoreductase, Na translocating |
| 35 | 96109 | 80542 | 81147 | MCA100893 | g2558477 | 2.00E-78 | Na-translocating NADH-quinone reductase subunit 5 |
| 35 | 96109 | 79287 | 80495 | MCA100894 | g1573127 | e-164 | Na-translocating NADH-quinone reductase beta-subunit |
| 35 | 96109 | 22117 | 23637 | MCA100915 | g1001214 | e-134 | hypothetical protein |
| 35 | 96109 | 2411 | 4147 | MCA100916 | g1786265 | 0 | acetolactate synthase III, val sensitive, large subunit |
| 35 | 96109 | 4168 | 4656 | MCA100917 | g1786266 | 6.00E-44 | acetolactate synthase III, val sensitive, small subunit |
| 35 | 96109 | 4835 | 5848 | MCA100918 | g2529237 | e-125 | acetohydroxy acid isomeroreductase |
| 35 | 96109 | 5960 | 6370 | MCA100919 | | | |
| 35 | 96109 | 6718 | 6918 | MCA100920 | g4454361 | 4.00E-22 | cold shock protein, CSPA |
| 35 | 96109 | 7163 | 7651 | MCA100921 | g1573284 | 2.00E-42 | crossover junction endodeoxyribonuclease (ruvC) |
| 35 | 96109 | 7852 | 8388 | MCA100922 | | | |
| 35 | 96109 | 8484 | 9779 | MCA100923 | g3298336 | 1.00E-65 | NorM |
| 35 | 96109 | 10000 | 11088 | MCA100924 | g1574692 | 5.00E-58 | cell division protein (ftsw) |
| 35 | 96109 | 11357 | 12736 | MCA100925 | g1574691 | 1.00E-75 | UDP-N-acetylmuranoylalanine-D-glutamate ligase |
| 35 | 96109 | 12938 | 13273 | MCA100926 | g2735324 | 7.00E-44 | PII-protein |
| 35 | 96109 | 66095 | 66631 | MCA100978 | g3323304 | 7.00E-13 | glpG protein, putative |
| 35 | 96109 | 26724 | 27458 | MCA101006 | g473823 | 3.00E-85 | 'methionine aminopeptidase' |
| 35 | 96109 | 27687 | 30377 | MCA101007 | g39257 | e-153 | uridylyl transferase |
| 35 | 96109 | 30510 | 31373 | MCA101008 | | | |
| 35 | 96109 | 32708 | 33978 | MCA101010 | g1788783 | 3.00E-40 | putative prophage integrase |
| 35 | 96109 | 35233 | 36276 | MCA101012 | | | |
| 35 | 96109 | 36398 | 37465 | MCA101013 | | | |
| 35 | 96109 | 37547 | 37858 | MCA101014 | | | |
| 35 | 96109 | 37855 | 38175 | MCA101015 | | | |
| 35 | 96109 | 56595 | 57344 | MCA101109 | g1573676 | 4.00E-56 | integrase/recombinase (xerC) |
| 35 | 96109 | 39637 | 39939 | MCA101486 | | | |
| 35 | 96109 | 40057 | 40410 | MCA101487 | | | |
| 35 | 96109 | 45467 | 46231 | MCA101490 | g1573242 | 2.00E-36 | ribonuclease BN (rbn) |
| 35 | 96109 | 46598 | 46957 | MCA101491 | g3493605 | 3.00E-30 | Trp repressor binding protein |
| 35 | 96109 | 47185 | 47616 | MCA101492 | | | |
| 35 | 96109 | 48860 | 49144 | MCA101494 | g149688 | 3.00E-32 | htpA |
| 35 | 96109 | 49273 | 50910 | MCA101495 | g499206 | 0 | GroEL |
| 35 | 96109 | 51130 | 51963 | MCA101496 | g1789192 | 1.00E-74 | prolipoprotein diacylglyceryl transferase |
| 35 | 96109 | 51990 | 52829 | MCA101497 | g2258280 | 2.00E-97 | thymidylate synthase |
| 35 | 96109 | 52856 | 53290 | MCA101498 | g665643 | 1.00E-28 | dihydrofolate reductase |
| 35 | 96109 | 53413 | 54426 | MCA101499 | g1573128 | 3.00E-47 | lipoprotein, putative |
| 35 | 96109 | 54579 | 55025 | MCA101500 | | | |
| 35 | 96109 | 55115 | 56281 | MCA101501 | g216628 | 1.00E-35 | UbiH (VisB) |
| 35 | 96109 | 57647 | 58471 | MCA101503 | g1790242 | 4.00E-80 | diaminopimelate |
| 35 | 96109 | 58748 | 59965 | MCA101504 | g1929094 | e-110 | LysA protein |

TABLE 1-continued

| Contig | Size | Start | End | Locus ID | Identifier | P-value | Description |
|---|---|---|---|---|---|---|---|
| 35 | 96109 | 60612 | 61766 | MCA101506 | g1405880 | 5.00E-83 | acetate kinase |
| 35 | 96109 | 62334 | 63320 | MCA101508 | g1574131 | e-127 | phosphate acetyltransferase (pta) |
| 35 | 96109 | 26139 | 26477 | MCA101763 | g2564977 | 4.00E-09 | hypothetical protein |
| 35 | 96109 | 41837 | 43138 | MCA101842 | g1033120 | 3.00E-15 | ORF_o469 |
| 35 | 96109 | 85730 | 86452 | MCA101876 | g836646 | 9.00E-64 | phosphoribosylformi-mino-5-aminoimidazole carboxamide |
| 35 | 96109 | 89243 | 89524 | MCA101877 | g42742 | 2.00E-11 | rimI protein (AA 1-161) |
| 35 | 96109 | 75011 | 75493 | MCA101878 | g4062570 | 5.00E-37 | 4-hydroxyphenylacetate 3-monooxygenase (EC 1.14.13.3) |
| 35 | 96109 | 75733 | 77289 | MCA101881 | g1787597 | 7.00E-94 | putative pump protein (transport) |
| 35 | 96109 | 77651 | 79135 | MCA101882 | g1573949 | 0 | catalase (hktE) |
| 35 | 96109 | 38185 | 38586 | MCA101930 | | | |
| 35 | 96109 | 40762 | 41004 | MCA102021 | g2313086 | 1.00E-08 | DNA primase (dhaG) |
| 35 | 96109 | 43196 | 43354 | MCA102022 | | | |
| 35 | 96109 | 95181 | 95342 | MCA102078 | | | |
| 36 | 92407 | 91233 | 91847 | MCA100081 | g2635437 | 1.00E-27 | similar to protease IV |
| 36 | 92407 | 50092 | 50511 | MCA100085 | g1574283 | 3.00E-53 | ribosomal protein L13 (rpL13) |
| 36 | 92407 | 49696 | 50073 | MCA100086 | g241867 | 3.00E-44 | ribosomal protein S9 homolog = rpsI |
| 36 | 92407 | 7088 | 7378 | MCA100136 | g2865528 | 1.00E-13 | mono-heme c-type cytochrome ScyA |
| 36 | 92407 | 7748 | 8335 | MCA100137 | g516878 | 3.00E-35 | cytochrome c4 preprotein |
| 36 | 92407 | 14107 | 15696 | MCA100530 | g581070 | e-144 | acyl coenzyne A synthetase |
| 36 | 92407 | 12531 | 13733 | MCA100531 | g1573978 | 2.00E-83 | DNA/pantothenate metabolism flavoprotein (dfp) |
| 36 | 92407 | 11001 | 12140 | MCA100532 | g551299 | e-106 | Na+/H+ antiporter |
| 36 | 92407 | 16025 | 17620 | MCA100708 | g581070 | e-166 | acyl coenzyme A synthetase |
| 36 | 92407 | 17919 | 18623 | MCA100709 | g1079663 | 6.00E-79 | RNase PH |
| 36 | 92407 | 18634 | 19089 | MCA100710 | | | |
| 36 | 92407 | 19908 | 20546 | MCA100712 | g436881 | 2.00E-34 | outer membrane phospholipase A |
| 36 | 92407 | 20579 | 21427 | MCA100713 | | | |
| 36 | 92407 | 21387 | 21977 | MCA100714 | | | |
| 36 | 92407 | 21974 | 22960 | MCA100715 | | | |
| 36 | 92407 | 22957 | 23763 | MCA100716 | | | |
| 36 | 92407 | 816 | 1589 | MCA100752 | g2984360 | 7.00E-71 | thiamine biosynthesis, |
| 36 | 92407 | 1761 | 3098 | MCA100753 | g2960158 | 7.00E-59 | hypothetical protein Rv3734c |
| 36 | 92407 | 3243 | 5234 | MCA100754 | g1574731 | 0 | methionyl-tRNA synthetase (metG) |
| 36 | 92407 | 5571 | 6977 | MCA100755 | g41206 | e-132 | cysteinyl-tRNA synthetase |
| 36 | 92407 | 61788 | 63133 | MCA100840 | g1788963 | e-156 | GTP-binding export factor |
| 36 | 92407 | 63356 | 64015 | MCA100842 | g1788109 | 4.00E-20 | orf, hypothetical protein |
| 36 | 92407 | 64186 | 64992 | MCA100843 | g1789437 | 4.00E-43 | bacitracin resistance |
| 36 | 92407 | 65314 | 65850 | MCA100844 | g3851182 | 5.00E-14 | unknown |
| 36 | 92407 | 65942 | 66205 | MCA100845 | | | |
| 36 | 92407 | 66244 | 67065 | MCA100846 | g396375 | 5.00E-64 | 4-hydroxybenzoate-octaprenyl transferase |
| 36 | 92407 | 67362 | 68897 | MCA100847 | g1449339 | e-137 | pitB |
| 36 | 92407 | 69294 | 69974 | MCA100848 | g606374 | 9.00E-53 | ORF_f231 |
| 36 | 92407 | 70365 | 70850 | MCA100849 | g1574067 | 2.00E-34 | conserved hypothetical protein |
| 36 | 92407 | 70982 | 71563 | MCA100850 | g497127 | 2.00E-55 | RNase T |
| 36 | 92407 | 38857 | 39717 | MCA100927 | g4376782 | 5.00E-12 | CT391 hypothetical protein |
| 36 | 92407 | 40914 | 41549 | MCA100929 | g3860928 | 5.00E-25 | ABC transporter ATP-binding protein |
| 36 | 92407 | 42061 | 44601 | MCA100931 | g1573874 | 0 | ATP-dependent Clp protease, ATPase subunit (clpB) |
| 36 | 92407 | 45517 | 45870 | MCA100933 | g1574279 | 2.00E-28 | stringent starvation protein B (sspB) |
| 36 | 92407 | 45891 | 46442 | MCA100934 | g42998 | 6.00E-33 | SSP (AA1-212) |

TABLE 1-continued

| Contig | Size | Start | End | Locus ID | Identifier | P-value | Description |
|---|---|---|---|---|---|---|---|
| 36 | 92407 | 46643 | 47320 | MCA100935 | g2642363 | 1.00E-39 | cytochrome c1 |
| 36 | 92407 | 47395 | 48567 | MCA100936 | g2642362 | e-133 | cytochrome b |
| 36 | 92407 | 48597 | 49166 | MCA100937 | g2642361 | 4.00E-48 | Fe-S protein |
| 36 | 92407 | 88972 | 90090 | MCA101033 | g305386 | 6.00E-21 | recombination protein |
| 36 | 92407 | 81971 | 82912 | MCA101037 | g1377868 | 2.00E-47 | cbb3-type cytochrome c oxidase CcoP subunit |
| 36 | 92407 | 71602 | 72657 | MCA101086 | g3868712 | e-114 | dihydroorotase |
| 36 | 92407 | 72855 | 74180 | MCA101087 | g1574583 | 0 | argininosuccinate synthetase (argG) |
| 36 | 92407 | 74397 | 74897 | MCA101088 | | | |
| 36 | 92407 | 75049 | 75960 | MCA101089 | g3643996 | 2.00E-30 | putative regulatory protein |
| 36 | 92407 | 76983 | 78173 | MCA101091 | g152210 | 4.00E-68 | nitrogen fixation protein fixG |
| 36 | 92407 | 79617 | 80960 | MCA101093 | g1552601 | e-179 | FixNd |
| 36 | 92407 | 81064 | 81636 | NCA101094 | g1002879 | 3.00E-56 | CcoO |
| 36 | 92407 | 83103 | 84722 | MCA101097 | g1574630 | 0 | CTP synthetase (pyrG) |
| 36 | 92407 | 84893 | 85729 | MCA101098 | g4235471 | e-114 | 2-dehydro-3-deoxyphosphooctonate aldolase |
| 36 | 92407 | 85823 | 87097 | MCA101099 | g1789141 | e-156 | enolase |
| 36 | 92407 | 87210 | 87455 | MCA101100 | g1789105 | 4.00E-08 | orf, hypothetical protein |
| 36 | 92407 | 87621 | 88316 | MCA101101 | g1573673 | 3.00E-36 | conserved hypothetical protein |
| 36 | 92407 | 39980 | 40804 | MCA101148 | g3860927 | 4.00E-24 | unknown |
| 36 | 92407 | 59021 | 60271 | MCA101153 | g42913 | 1.00E-58 | ORF 45 peptide (AA 1-400) |
| 36 | 92407 | 55081 | 58941 | MCA101154 | g42914 | 1.00E-59 | SbcC (AA 1-1048) |
| 36 | 92407 | 51152 | 52987 | MCA101156 | g581463 | 0 | homologous to E. coli gidA |
| 36 | 92407 | 35356 | 36111 | MCA101172 | g1651445 | 2.00E-42 | SmtA protein. |
| 36 | 92407 | 33986 | 35242 | MCA101173 | g1245347 | 2.00E-43 | AlgI |
| 36 | 92407 | 30688 | 31161 | MCA101176 | g2765835 | 2.00E-29 | hypothetical protein |
| 36 | 92407 | 29194 | 30474 | MCA101177 | g3132889 | 1.00E-62 | WaaA |
| 36 | 92407 | 26469 | 28985 | MCA101178 | g1574460 | e-160 | aminopeptidase N (pepN) |
| 36 | 92407 | 25542 | 26057 | MCA101179 | g663068 | 1.00E-26 | PAL |
| 36 | 92407 | 8594 | 9688 | MCA101272 | | | |
| 36 | 92407 | 9676 | 10008 | MCA101294 | | | |
| 36 | 92407 | 24074 | 24832 | MCA101848 | | | |
| 36 | 92407 | 36281 | 37267 | MCA101850 | | | |
| 36 | 92407 | 37432 | 38508 | MCA101851 | g3860926 | 1.00E-08 | unknown |
| 36 | 92407 | 60775 | 61569 | MCA101909 | g1788964 | 2.00E-15 | orf, hypothetical protein |
| 36 | 92407 | 81687 | 81869 | MCA101928 | | | |
| 36 | 92407 | 53341 | 54315 | MCA101944 | | | |
| 36 | 92407 | 54504 | 54968 | MCA101945 | | | |
| 37 | 99629 | 69767 | 70210 | MCA100038 | g1718488 | 6.00E-34 | FabZ |
| 37 | 99629 | 70275 | 71039 | MCA100039 | g1786378 | 3.00E-77 | UDP-N-acetylglucosamine acetyltransferase |
| 37 | 99629 | 71432 | 72897 | MCA100082 | g1573742 | e-119 | sodium-dependent transporter, putative |
| 37 | 99629 | 76489 | 78342 | MCA100169 | g2599340 | 2.00E-40 | protein-disulfide reductase |
| 37 | 99629 | 51376 | 52041 | MCA100276 | g2865530 | 3.00E-30 | cytochrome c maturation protein B |
| 37 | 99629 | 73294 | 74871 | MCA100290 | g142301 | e-168 | cytochrome d subunit Ia |
| 37 | 99629 | 74913 | 76046 | MCA100291 | g1786954 | 2.00E-99 | cytochrome d terminal oxidase polypeptide subunit II |
| 37 | 99629 | 66172 | 68571 | MCA100323 | g1552754 | e-123 | hypothetical protein |
| 37 | 99629 | 68643 | 69560 | MCA100324 | g1573936 | 2.00E-56 | UDP-3-O-(3-hydroxymyristoyl)-glucosamine N-acyltransfer |
| 37 | 99629 | 33622 | 34110 | MCA100374 | g1574669 | 1.00E-31 | thioredoxin, putative |
| 37 | 99629 | 32014 | 33450 | MCA100375 | g1573139 | e-105 | amino acid carrier protein, putative |
| 37 | 99629 | 2692 | 5811 | MCA100461 | g438854 | 0 | envD homologue; ORFB |
| 37 | 99629 | 5884 | 7308 | MCA100564 | g3184190 | 3.00E-77 | OprM |
| 37 | 99629 | 8308 | 9618 | MCA100566 | g1061260 | 2.00E-68 | putative protein |
| 37 | 99629 | 9973 | 11343 | MCA100567 | g1788397 | e-165 | orf, hypothetical protein |

TABLE 1-continued

| Contig | Size | Start | End | Locus ID | Identifier | P-value | Description |
|---|---|---|---|---|---|---|---|
| 37 | 99629 | 11391 | 12323 | MCA100568 | g2314272 | 6.00E-88 | cytosine specific DNA methyltransferase (BSP6IM) |
| 37 | 99629 | 2 | 532 | MCA100700 | g1786393 | 5.00E-27 | orf, hypothetical protein |
| 37 | 99629 | 56471 | 57733 | MCA100776 | g1651420 | e-145 | Serine-tRNA ligase (EC 6.1.1.11) |
| 37 | 99629 | 57951 | 59921 | MCA100777 | g2367177 | 0 | transketolase 1 isozyme |
| 37 | 99629 | 60119 | 60835 | MCA100778 | g3417448 | 1.00E-67 | UMP kinase |
| 37 | 99629 | 60950 | 61501 | MCA100779 | g3417449 | 1.00E-63 | ribosome recycling factor |
| 37 | 99629 | 61598 | 62323 | MCA100780 | g1786371 | 5.00E-54 | orf, hypothetical protein |
| 37 | 99629 | 62522 | 63199 | MCA100781 | g1262332 | 5.00E-39 | CDP-diglyceride synthetase |
| 37 | 99629 | 63358 | 64560 | MCA100782 | g1786369 | 3.00E-85 | putative ATP-binding component of a transport system |
| 37 | 99629 | 64584 | 65951 | MCA100783 | g1552753 | 8.00E-83 | hypothetical |
| 37 | 99629 | 34923 | 35243 | MCA100789 | g142304 | 3.00E-52 | ferredoxin I |
| 37 | 99629 | 1269 | 2564 | MCA100852 | g532310 | 1.00E-61 | 42 kDa protein |
| 37 | 99629 | 26942 | 30208 | MCA101055 | g2367096 | 0 | isoleucine tRNA synthetase |
| 37 | 99629 | 83288 | 84046 | MCA101084 | g1789140 | 3.00E-18 | orf, hypothetical protein |
| 37 | 99629 | 30484 | 31758 | MCA101163 | g4062560 | e-147 | Uracil transport protein |
| 37 | 99629 | 38692 | 40539 | MCA101256 | | | |
| 37 | 99629 | 40499 | 41389 | MCA101257 | | | |
| 37 | 99629 | 43223 | 46123 | MCA101259 | g1574225 | 0 | valyl-tRNA synthetase (valS) |
| 37 | 99629 | 46207 | 47085 | MCA101260 | g303628 | e-161 | MboI methyltransferase A |
| 37 | 99629 | 47093 | 47932 | MCA101261 | g303629 | e-151 | MboI endonuclease |
| 37 | 99629 | 47937 | 48755 | MCA101262 | g303630 | e-145 | MboI methyltransferase C |
| 37 | 99629 | 50795 | 51373 | MCA101265 | g46024 | 2.00E-25 | helA |
| 37 | 99629 | 26437 | 26910 | MCA101360 | g151348 | 3.00E-35 | signal peptidase II |
| 37 | 99629 | 25749 | 26177 | MCA101361 | g151349 | 2.00E-26 | ORF149 |
| 37 | 99629 | 24426 | 25547 | MCA101362 | g1835114 | 1.00E-95 | homoserine O-acetyltransferase |
| 37 | 99629 | 23029 | 23605 | MCA101364 | g4062259 | 6.00E-14 | Sel-1 protein |
| 37 | 99629 | 20479 | 22755 | MCA101365 | g308942 | 0 | major outer membrane protein |
| 37 | 99629 | 18600 | 20063 | MCA101366 | g38720 | 0 | IMP dehydrogenase |
| 37 | 99629 | 17326 | 18006 | MCA101368 | g3135321 | 7.00E-33 | putative thiol:disulfide interchange protein precursor |
| 37 | 99629 | 15653 | 16846 | MCA101369 | g45329 | 8.00E-97 | homoserine dehydrogenase |
| 37 | 99629 | 14813 | 15373 | MCA101370 | g1790296 | 1.00E-55 | orf, hypothetical protein |
| 37 | 99629 | 13917 | 14735 | MCA101371 | g606086 | 6.00E-72 | ORF_f286 |
| 37 | 99629 | 78730 | 80198 | MCA101417 | g141886 | 0 | acetaldehyde dehydrogenase II |
| 37 | 99629 | 80403 | 81914 | MCA101418 | g2635246 | e-118 | similar to sodium/proton-dependent alanine carrier prot |
| 37 | 99629 | 82372 | 82926 | MCA101419 | g3322862 | 1.00E-33 | Tp70 protein |
| 37 | 99629 | 84049 | 84567 | MCA101421 | | | |
| 37 | 99629 | 98444 | 98752 | MCA101422 | g216636 | 3.00E-21 | ribosomal protein L21 |
| 37 | 99629 | 85377 | 86027 | MCA101423 | g4102010 | 2.00E-38 | putative transposase |
| 37 | 99629 | 86093 | 86667 | MCA101424 | g4512224 | 2.00E-26 | Similar to IS1301 of *Neisseria meningitidis* |
| 37 | 99629 | 86955 | 88568 | MCA101426 | g1747491 | 0 | alxA |
| 37 | 99629 | 88573 | 89919 | MCA101427 | g1685099 | 4.00E-56 | HSDS |
| 37 | 99629 | 91158 | 94300 | MCA101429 | g1685100 | 0 | HSDR |
| 37 | 99629 | 94381 | 95240 | MCA101430 | g1786518 | 6.00E-66 | putative oxidoreductase |
| 37 | 99629 | 95287 | 95940 | MCA101431 | g1574733 | 5.00E-72 | NAD(P)H-flavin oxidoreductase |
| 37 | 99629 | 96051 | 97094 | MCA101432 | g1303964 | 2.00E-70 | YqjM |
| 37 | 99629 | 97366 | 98229 | MCA101433 | g150233 | 6.00E-30 | nahR protein precursor |
| 37 | 99629 | 98820 | 99074 | MCA101440 | g216637 | 2.00E-28 | ribosomal protein L27 |

TABLE 1-continued

| Contig | Size | Start | End | Locus ID | Identifier | P-value | Description |
|---|---|---|---|---|---|---|---|
| 37 | 99629 | 13079 | 13333 | MCA101463 | g1518927 | 6.00E-28 | ferredoxin |
| 37 | 99629 | 13439 | 13879 | MCA101466 | g1575483 | 3.00E-23 | Lporfx |
| 37 | 99629 | 12334 | 13065 | MCA101598 | g4155637 | 9.00E-79 | putative |
| 37 | 99629 | 53924 | 54736 | MCA101923 | g765096 | 2.00E-94 | heat-shock sigma factor |
| 37 | 99629 | 36268 | 37779 | MCA101924 | g1787309 | e-103 | putative virulence factor |
| 37 | 99629 | 37994 | 38530 | MCA101929 | g4079828 | 8.00E-45 | N-acetyl-anhydromuramyl-L-alanine amidase |
| 37 | 99629 | 41474 | 42911 | MCA101936 | g2633081 | e-119 | similar to 2-oxoglutarate/malate translocator |
| 37 | 99629 | 48799 | 49662 | MCA1d1938 | g580726 | 7.00E-63 | Portion of hypothetical protein |
| 37 | 99629 | 52121 | 52933 | MCA101939 | g3513356 | 3.00E-39 | hypothetical protein |
| 37 | 99629 | 89930 | 91132 | MCA102002 | | | |
| 38 | 94750 | 82819 | 83559 | MCA100037 | g1573162 | 3.00E-71 | tRNA (guanine-N1)-methyltransferase (trmD) |
| 38 | 94750 | 83736 | 84065 | MCA100220 | g1800011 | 8.00E-36 | ribosomal protein L19 |
| 38 | 94750 | 84195 | 84599 | MCA100221 | g145063 | 8.00E-31 | two-subunit pilin precursor |
| 38 | 94750 | 38362 | 39300 | MCA100287 | | | |
| 38 | 94750 | 39368 | 40069 | McA100288 | g39705 | 3.00E-27 | fimC |
| 38 | 94750 | 37413 | 38177 | McA100301 | g1573311 | 4.00E-49 | conserved hypothetical protein |
| 38 | 94750 | 36351 | 37259 | MCA100302 | g1786208 | 7.00E-49 | putative regulator |
| 38 | 94750 | 43520 | 43906 | MCA100403 | g1055071 | 7.00E-33 | C23G10.2 gene product |
| 38 | 94750 | 40106 | 42352 | MCA100405 | g147345 | e-140 | primosomal protein n' |
| 38 | 94750 | 601 | 1360 | MCA100435 | g2633826 | 1.00E-30 | similar to hypothetical proteins |
| 38 | 94750 | 1401 | 2000 | MCA100436 | g1001747 | 1.00E-40 | alkaline phosphatase-like |
| 38 | 94750 | 2433 | 3071 | MCA100437 | g1574697 | 4.00E-12 | cell division protein (ftsQ) |
| 38 | 94750 | 3143 | 4201 | MCA100438 | g2738588 | 5.00E-23 | cell division protein |
| 38 | 94750 | 77707 | 78381 | MCA100467 | g1079807 | 9.00E-42 | RstA |
| 38 | 94750 | 79179 | 80048 | MCA100469 | g1742648 | 4.00E-37 | Sensor protein RstB (EC 2.7.3.—) |
| 38 | 94750 | 81833 | 82078 | MCA100471 | g1573164 | 3.00E-25 | ribosomal protein S16 (rpS16) |
| 38 | 94750 | 82288 | 82782 | MCA100472 | g1573163 | 7.00E-26 | conserved hypothetical protein |
| 38 | 94750 | 29640 | 30077 | MCA100521 | g4164224 | 3.00E-55 | ferric uptake regulator |
| 38 | 94750 | 30269 | 31297 | MCA100522 | g151490 | 7.00E-90 | twitching motility protein |
| 38 | 94750 | 31720 | 32301 | MCA100523 | g454838 | 7.00E-51 | ORF 6; putative |
| 38 | 94750 | 32364 | 33974 | MCA100524 | g1653472 | e-120 | NH(3)-dependent NAD(+) synthetase |
| 38 | 94750 | 25258 | 27037 | MCA100546 | g2735093 | 0 | ubiquitous surface protein A 2 |
| 38 | 94750 | 27198 | 28070 | MCA100547 | g2677632 | 1.00E-66 | methionine regulatory protein MetR |
| 38 | 94750 | 28330 | 28986 | MCA100548 | g1799710 | 3.00E-47 | dedA protein |
| 38 | 94750 | 70429 | 71286 | MCA100628 | g669111 | 9.00E-79 | alternate atpB CDS |
| 38 | 94750 | 71347 | 71586 | MCA100629 | g1573462 | 1.00E-14 | ATP synthase F0, subunit c (atpE) |
| 38 | 94750 | 71683 | 72144 | MCA100630 | g581814 | 4.00E-30 | uncF (AA 1-156) |
| 38 | 94750 | 72160 | 72699 | MCA100631 | g48336 | 9.00E-26 | uncH (AA 1-177) |
| 38 | 94750 | 72749 | 74284 | MCA100632 | g1790172 | 0 | membrane-bound ATP synthase, F1 sector, alpha-subunit |
| 38 | 94750 | 74372 | 75238 | MCA100633 | g1790171 | 3.00E-96 | membrane-bound ATP synthase, F1 sector, gamma-subunit |
| 38 | 94750 | 75694 | 77103 | MCA100635 | g1573457 | 0 | ATP synthase F1, subunit beta (atpD) |
| 38 | 94750 | 77188 | 77586 | MCA100636 | g1573456 | 2.00E-16 | ATP synthase F1, subunit epsilon (atpC) |
| 38 | 94750 | 42399 | 43304 | MCA100808 | g1788771 | 1.00E-66 | orf, hypothetical protein |
| 38 | 94750 | 23867 | 24892 | MCA101243 | g1573514 | e-106 | O-sialoglycoprotein endopeptidase (gcp) |
| 38 | 94750 | 29005 | 29400 | MCA101264 | g1033113 | 1.00E-11 | ORF_o113 |

TABLE 1-continued

| Contig | Size | Start | End | Locus ID | Identifier | P-value | Description |
|---|---|---|---|---|---|---|---|
| 38 | 94750 | 4673 | 5742 | MCA101528 | g216509 | 3.00E-82 | cell division protein fstZ |
| 38 | 94750 | 5866 | 6756 | MCA101529 | g1574235 | 1.00E-42 | conserved hypothetical protein |
| 38 | 94750 | 7767 | 8792 | MCA10153i | g440089 | e-137 | RecA |
| 38 | 94750 | 9699 | 11027 | MCA101533 | g3876615 | e-112 | Similar to Yeast D-lactate dehydrogenase (SW:DLD1_YEAST) |
| 38 | 94750 | 11050 | 11592 | MCA101534 | | | |
| 38 | 94750 | 11674 | 12723 | MCA101535 | | | |
| 38 | 94750 | 12838 | 13641 | MCA101536 | g1573029 | 1.00E-27 | conserved hypothetical protein |
| 38 | 94750 | 13667 | 14434 | MCA101537 | g1789177 | 1.00E-42 | putative enzyme |
| 38 | 94750 | 14676 | 15545 | MCA101538 | g1574480 | e-101 | 2,3,4,5-tetrahydropyridine-2-carboxylate N-succinyltransf |
| 38 | 94750 | 16830 | 17747 | MCA101540 | g1572971 | 3.00E-93 | lipoate biosynthesis protein A (lipA) |
| 38 | 94750 | 18269 | 19222 | MCA101542 | g1786681 | 2.00E-89 | ferrochelatase: final enzyme of heme biosynthesis |
| 38 | 94750 | 19956 | 21070 | MCA101544 | g1652222 | 9.00E-44 | hypothetical protein |
| 38 | 94750 | 21261 | 23480 | MCA101545 | g1030696 | 0 | isocitrate dehydrogenase |
| 38 | 94750 | 44197 | 46308 | MCA101565 | g1574600 | 9.00E-78 | guanosine-3',5'-bis(diphosphate) 3'-pyrophosphohydrolase |
| 38 | 94750 | 46693 | 46932 | MCA101566 | g1574602 | 1.00E-14 | DNA-directed RNA polymerase, omega chain (rpoZ) |
| 38 | 94750 | 47038 | 47643 | MCA101567 | g290498 | 2.00E-50 | 5'guanylate kinase |
| 38 | 94750 | 47816 | 48742 | MCA101568 | g216456 | e-110 | hypothetical 34.8 K protein (PIR:JE0403) |
| 38 | 94750 | 48853 | 50493 | MCA101569 | g1789259 | e-124 | ssDNA exonuclease, 5' --> 3' specific |
| 38 | 94750 | 50589 | 51176 | MCA101570 | g290496 | 2.00E-33 | o223 |
| 38 | 94750 | 51346 | 52017 | MCA101572 | g2984272 | 3.00E-19 | hypothetical protein |
| 38 | 94750 | 52519 | 53892 | MCA101574 | g2340815 | 0 | L-2,4-diaminobutyrate: 2-ketoglutarate 4-aminotransferase |
| 38 | 94750 | 54051 | 55967 | MCA101575 | g4454667 | e-134 | methyltransferase |
| 38 | 94750 | 55995 | 58601 | MCA101576 | g4454668 | 0 | restriction endonuclease |
| 38 | 94750 | 58652 | 60190 | MCA101577 | g893355 | 0 | L-2,4-diaminobutyrate decarboxylase |
| 38 | 94750 | 60278 | 62041 | MCA101578 | g472402 | e-128 | UVR excinuclease subunit C |
| 38 | 94750 | 62223 | 62858 | MCA101579 | g1573552 | 2.00E-44 | phosphoglycolate phosphatase (gph) |
| 38 | 94750 | 63199 | 63741 | MCA101580 | | | |
| 38 | 94750 | 63889 | 64746 | MCA101581 | g1786337 | 1.00E-42 | putative tRNA synthetase |
| 38 | 94750 | 64772 | 65185 | MCA101582 | g1786338 | 4.00E-43 | dnaK suppressor protein |
| 38 | 94750 | 65335 | 66003 | MCA101583 | g882562 | 1.00E-23 | icc gene product |
| 38 | 94750 | 66160 | 66916 | MCA101584 | g1573380 | 3.00E-27 | conserved hypothetical integral membrane protein |
| 38 | 94750 | 66967 | 67674 | MCA101585 | g1736501 | 1.00E-47 | Sulfate transport ATP-binding protein CysA. |
| 38 | 94750 | 67700 | 68140 | MCA101586 | g1790480 | 7.00E-20 | putative regulator |
| 38 | 94750 | 69471 | 69878 | MCA101588 | | | |
| 38 | 94750 | 75267 | 75602 | MCA101681 | | | |
| 38 | 94750 | 68546 | 69241 | MCA101853 | g1788164 | 3.00E-16 | putative adhesin |
| 38 | 94750 | 34301 | 34576 | MCA101890 | | | |
| 38 | 94750 | 35674 | 36312 | MCA101892 | | | |
| 38 | 94750 | 87827 | 89506 | MCA101940 | g409365 | 0 | urocanase |
| 38 | 94750 | 89601 | 91106 | MCA101941 | g151274 | e-164 | histidine ammonia-lyase (hutH) precursor (gtg start codon (E.C. 4.3.1.3) |
| 38 | 94750 | 91634 | 92272 | MCA101942 | g149204 | 5.00E-35 | histidine utilization repressor G |

TABLE 1-continued

| Contig | Size | Start | End | Locus ID | Identifier | P-value | Description |
|---|---|---|---|---|---|---|---|
| 38 | 94750 | 92575 | 93723 | MCA101946 | g4106576 | e-109 | ORF9, highly similar to imidazolone propionate hydrolase |
| 38 | 94750 | 15658 | 16503 | MCA101947 | g2285919 | 1.00E-13 | K5L + K6L |
| 38 | 94750 | 6816 | 7307 | MCA101948 | g1321618 | 6.00E-16 | |
| 38 | 94750 | 80209 | 81537 | MCA101953 | g3402275 | 1.00E-51 | EnvZ protein |
| 38 | 94750 | 85007 | 87612 | MCA101955 | g2367097 | 0 | aconitate hydrase B |
| 39 | 100848 | 79190 | 79684 | MCA100004 | g1835603 | 1.00E-30 | 15 kDa protein |
| 39 | 100848 | 77575 | 78220 | MCA100013 | g49095 | 2.00E-47 | triosephosphate isomerase |
| 39 | 100848 | 33560 | 34450 | MCA100033 | g1786984 | 3.00E-38 | putative transcriptional regulator LYSR-type |
| 39 | 100848 | 16050 | 17411 | MCA100152 | g154205 | e-139 | phosphomannomutase |
| 39 | 100848 | 38007 | 39128 | MCA100236 | g1574558 | 2.00E-27 | conserved hypothetical protein |
| 39 | 100848 | 39149 | 40258 | MCA100237 | g1790713 | 7.00E-15 | orf, hypothetical protein |
| 39 | 100848 | 13324 | 14526 | MCA100260 | g1788092 | 4.00E-39 | putative amino acid/amine transport protein |
| 39 | 100848 | 14586 | 15035 | MCA100261 | | | |
| 39 | 100848 | 15091 | 15930 | MCA100262 | g1773171 | 4.00E-38 | similar to *M. tuberculosis* MTCY277.09 |
| 39 | 100848 | 36123 | 37547 | MCA100305 | g2984771 | e-101 | PhpA |
| 39 | 100848 | 34625 | 35815 | MCA100306 | g409800 | e-132 | tyrosine aminotransferase |
| 39 | 100848 | 89115 | 89381 | MCA100389 | g429056 | 1.00E-26 | ribosomal protein S15 |
| 39 | 100848 | 89607 | 91682 | MCA100390 | g3650364 | 0 | polyribonucleotide nucleotidyltransferase |
| 39 | 100848 | 91827 | 92300 | MCA100391 | g2959336 | 4.00E-46 | hypothetical protein |
| 39 | 100848 | 92532 | 92957 | MCA100392 | g1100876 | 5.00E-19 | hypothetical OrfY |
| 39 | 100848 | 92969 | 93382 | MCA100393 | g1789538 | 2.00E-08 | orf, hypothetical protein |
| 39 | 100848 | 93467 | 94066 | MCA100394 | g1789540 | 1.00E-06 | putative periplasmic protein |
| 39 | 100848 | 28411 | 29109 | MCA100525 | g41638 | 3.00E-64 | PufX protein |
| 39 | 100848 | 30030 | 30761 | MCA100527 | g1742082 | 8.00E-54 | Internalin B |
| 39 | 100848 | 30895 | 32214 | MCA100528 | g537059 | e-129 | ORF_f447 |
| 39 | 100848 | 32302 | 33378 | MCA100529 | g2916960 | 2.00E-46 | chaA |
| 39 | 100848 | 94363 | 94614 | MCA100761 | g415661 | 4.00E-14 | putative; ORF3 |
| 39 | 100848 | 94621 | 95874 | MCA100762 | g415662 | e-141 | UDP-N-acetylglucosamine 1-carboxyvinyl transferase |
| 39 | 100848 | 95992 | 96555 | MCA100763 | g2636005 | 8.00E-43 | ATP phosphoribosyl transferase |
| 39 | 100848 | 96820 | 98121 | MCA100764 | g2983343 | e-101 | histidinol dehydrogenase |
| 39 | 100848 | 98225 | 99295 | MCA100765 | g440346 | 3.00E-99 | histidinol phosphate aminotransferase |
| 39 | 100848 | 99499 | 100359 | MCA100766 | g2984079 | 1.00E-41 | fumarate hydratase (fumarase) |
| 39 | 100848 | 79796 | 81271 | MCA100801 | g1789560 | e-128 | transcription pausing; L factor |
| 39 | 100848 | 81439 | 84168 | MCA100802 | g3850831 | 0 | initiation factor IF2-alpha |
| 39 | 100848 | 86548 | 86931 | MCA100804 | g606107 | 2.00E-17 | P15B |
| 39 | 100848 | 86964 | 87845 | MCA100805 | g1574748 | 2.00E-54 | tRNA pseudouridine 55 synthase (truB) |
| 39 | 100848 | 67997 | 69420 | MCA100815 | g717082 | e-139 | glutamyl-tRNA synthetase |
| 39 | 100848 | 69744 | 70682 | MCA100816 | g42318 | 8.00E-73 | orfB |
| 39 | 100848 | 70742 | 71092 | MCA100817 | | | |
| 39 | 100848 | 71246 | 73027 | MCA100818 | g840842 | 2.00E-81 | penicillin-binding protein 3 |
| 39 | 100848 | 73207 | 74637 | MCA100819 | g1574688 | 2.00E-74 | UDP-N-acetylmuramyl-tripeptide synthetase (murE) |
| 39 | 100848 | 74755 | 76140 | MCA100820 | g1786274 | 9.00E-76 | D-alanine:D-alanine-adding enzyme |
| 39 | 100848 | 76209 | 77270 | MCA100821 | g1574690 | e-105 | phospho-N-acetylmuramoyl-pentapeptide-transferase E |

TABLE 1-continued

| Contig | Size | Start | End | Locus ID | Identifier | P-value | Description |
|---|---|---|---|---|---|---|---|
| 39 | 100848 | 18959 | 19780 | MCA100862 | g1789144 | 2.00E-46 | orf, hypothetical protein |
| 39 | 100848 | 19920 | 20072 | MCA100863 | g973208 | 4.00E-09 | unknown |
| 39 | 100848 | 20368 | 21621 | MCA100864 | g3650360 | 3.00E-58 | polynucleotide adenylyltransferase |
| 39 | 100848 | 22089 | 22535 | MCA100865 | g1573012 | 4.00E-30 | 2-amino-4-hydroxy-6-hydroxymethyldihydro-pteridine-pyroph |
| 39 | 100848 | 22769 | 23563 | MCA100866 | g3970812 | 2.00E-74 | 3-methyl-2-oxobutanoate hydroxymethyltransferase |
| 39 | 100848 | 23576 | 24412 | MCA100867 | g854607 | 2.00E-64 | putative pantoate--beta-alanine ligase |
| 39 | 100848 | 24556 | 25401 | MCA100868 | g4138364 | 3.00E-59 | ORF284 |
| 39 | 100848 | 25460 | 26035 | MCA100869 | g4467403 | 2.00E-23 | hsdS protein (AA 1-410) |
| 39 | 100848 | 26235 | 26776 | MCA100870 | g4155604 | 4.00E-16 | putative |
| 39 | 100848 | 29173 | 29787 | MCA100902 | g606319 | 7.00E-20 | 27 kD protein in ECDAMOPRA |
| 39 | 100848 | 155 | 772 | MCA100959 | | | |
| 39 | 100848 | 787 | 1221 | MCA100960 | | | |
| 39 | 100848 | 2287 | 2865 | MCA100962 | g1789409 | 3.00E-18 | orf, hypothetical protein |
| 39 | 100848 | 3088 | 4974 | MCA100963 | g4176381 | 0 | topoisomerase IV subunit |
| 39 | 100848 | 5074 | 5685 | MCA100964 | g2622643 | 3.00E-33 | imidazoleglycerol-phosphate synthase |
| 39 | 100848 | 5692 | 6273 | MCA100965 | g38667 | 3.00E-57 | hisB |
| 39 | 100848 | 6509 | 7017 | MCA100966 | g41474 | 2.00E-43 | fms |
| 39 | 100848 | 7147 | 8805 | MCA100967 | g1800021 | 2.00E-69 | DNA repair protein RecN |
| 39 | 100848 | 8859 | 3404 | MCA100968 | g1789317 | 1.00E-30 | orf, hypothetical protein |
| 39 | 100848 | 9428 | 9826 | MCA100969 | g1789318 | 1.00E-23 | orf, hypothetical protein |
| 39 | 100848 | 9901 | 10368 | MCA100970 | | | |
| 39 | 100848 | 10483 | 10698 | MCA100971 | g1789881 | 1.00E-15 | orf, hypothetical protein |
| 39 | 100848 | 10775 | 11650 | MCA100972 | g2645800 | 3.00E-62 | site-specific recombinase |
| 39 | 100848 | 17947 | 18870 | MCA100983 | g1781241 | 1.00E-99 | cysK |
| 39 | 100848 | 27386 | 27973 | MCA100985 | g1814074 | 1.00E-34 | DsbA |
| 39 | 100848 | 40307 | 41437 | MCA101057 | g1657573 | 3.00E-49 | hypothetical protein |
| 39 | 100848 | 41491 | 41649 | MCA101058 | | | |
| 39 | 100848 | 41663 | 42544 | MCA101059 | g1773136 | 2.00E-52 | acyl-coA thioesterase II |
| 39 | 100848 | 42892 | 45303 | MCA101060 | g1573755 | e-124 | glycerol-3-phosphate acyltransferase (plsB) |
| 39 | 100848 | 45434 | 46276 | MCA101061 | g3372537 | 1.00E-61 | UTP-glucose-1-phosphate uridylyltransferase |
| 39 | 100848 | 46369 | 47937 | MCA101062 | g927386 | e-163 | glucose-6-phosphate isomerase |
| 39 | 100848 | 48368 | 48901 | MCA101063 | g3559950 | 1.00E-20 | UDP-glucose 6-dehydrogenase |
| 39 | 100848 | 49598 | 49843 | MCA101064 | | | |
| 39 | 100848 | 50331 | 50846 | MCA101065 | | | |
| 39 | 100848 | 64882 | 65763 | MCA101402 | g2661442 | 4.00E-80 | YafJ |
| 39 | 100848 | 62805 | 63572 | MCA101404 | g38674 | 2.00E-91 | cyclase |
| 39 | 100848 | 62144 | 62566 | MCA101405 | g1773099 | 2.00E-42 | probable riboflavin synthase beta chain |
| 39 | 100848 | 61547 | 61969 | MCA101406 | g1574763 | 4.00E-17 | N utilization substance protein B (nusB) |
| 39 | 100848 | 60480 | 61445 | MCA101407 | g2329840 | 1.00E-50 | thiamine-monophosphate kinase |
| 39 | 100848 | 59736 | 60230 | MCA101408 | g1574765 | 4.00E-19 | phosphatidylglycero-phosphatase A (pgpA) |
| 39 | 100848 | 58735 | 59224 | MCA101410 | g2769574 | 4.00E-22 | methylase |
| 39 | 100848 | 56628 | 57614 | MCA101412 | g580766 | 1.00E-54 | BepI modification methylase (AA 1 - 403) |
| 39 | 100848 | 54681 | 55580 | MCA101414 | g1573822 | 8.00E-37 | conserved hypothetical protein |
| 39 | 100848 | 52655 | 54490 | MCA101415 | g2654003 | 0 | glucosamine synthase |
| 39 | 100848 | 51555 | 52574 | MCA101416 | g1429254 | e-111 | UDP-glucose 4-epimerase |

TABLE 1-continued

| Contig | Size | Start | End | Locus ID | Identifier | P-value | Description |
|---|---|---|---|---|---|---|---|
| 39 | 100848 | 11886 | 13143 | MCA101479 | g1787337 | e-109 | 3-oxoacyl-[acyl-carrier-protein] synthase II |
| 39 | 100848 | 88447 | 88902 | MCA101792 | g940802 | 1.00E-15 | outer membrane protein |
| 39 | 100848 | 93930 | 94229 | MCA101810 | | | |
| 39 | 100848 | 50855 | 51313 | MCA101869 | | | |
| 39 | 100848 | 56357 | 56563 | MCA101870 | | | |
| 39 | 100848 | 63863 | 64879 | MCA101871 | g3089616 | 4.00E-13 | homoserine kinase homolog |
| 39 | 100848 | 65763 | 66659 | MCA101872 | | | |
| 39 | 100848 | 78259 | 78561 | MCA102126 | | | |
| 4 | 2642 | 463 | 783 | MCA100115 | g290546 | 1.00E-07 | f135 |
| 4 | 2642 | 954 | 1610 | MCA100117 | g2960085 | 3.00E-15 | hypothetical protein Rv3661 |
| 4 | 2642 | 1764 | 2642 | MCA101198 | g154276 | 8.00E-96 | peptide chain release factor 2 |
| 40 | 119211 | 50160 | 50753 | MCA100057 | g4062767 | 2.00E-34 | ZK688.3 protein |
| 40 | 119211 | 50865 | 51788 | MCA100058 | g1359474 | 1.00E-81 | homology to hydrolases |
| 40 | 119211 | 51852 | 52013 | MCA100059 | g599606 | 5.00E-24 | rubredoxin |
| 40 | 119211 | 8413 | 8958 | MCA100065 | g4337446 | 1.00E-58 | ECORLD-ORF1; encoded by M30388 and Z29635 |
| 40 | 119211 | 10888 | 11190 | MCA100146 | g1573418 | 2.00E-24 | conserved hypothetical protein |
| 40 | 119211 | 10282 | 10866 | MCA100147 | g1573419 | 2.00E-46 | recombination protein (recR) |
| 40 | 119211 | 9069 | 10181 | MCA100148 | g1788105 | 6.00E-35 | RNase D, processes tRNA precursor |
| 40 | 119211 | 106 | 690 | MCA100179 | g3861026 | 1.00E-13 | unknown |
| 40 | 119211 | 693 | 1781 | MCA100180 | g606171 | 6.00E-92 | ORF_f375 |
| 40 | 119211 | 1850 | 2371 | MCA100181 | g1742876 | 3.00E-28 | ORF-ID:o329#2; similar to [A40360] |
| 40 | 119211 | 2693 | 3697 | MCA100182 | g2634701 | 1.00E-61 | NAD(P)H-dependent glycerol-3-phosphate dehydrogenase |
| 40 | 119211 | 7778 | 8185 | MCA100367 | g145892 | 2.00E-18 | biotin carboxyl carrier protein |
| 40 | 119211 | 6422 | 7750 | MCA100368 | g405541 | e-152 | biotin carboxylase |
| 40 | 119211 | 5139 | 6181 | MCA100369 | g1786881 | 2.00E-94 | putative ATP-binding protein in pho regulon |
| 40 | 119211 | 4544 | 4891 | MCA100370 | g1786880 | 4.00E-13 | orf, hypothetical protein |
| 40 | 119211 | 27651 | 28547 | MCA100431 | g151405 | e-111 | phaseolotoxin sensitive octase |
| 40 | 119211 | 26345 | 26839 | MCA100433 | g2632225 | 9.00E-15 | YkuD protein |
| 40 | 119211 | 76550 | 76939 | MCA100482 | g304913 | 3.00E-26 | urf2 |
| 40 | 119211 | 114141 | 114743 | MCA100510 | g286176 | 7.00E-28 | negative regulator of pyocin genes |
| 40 | 119211 | 115659 | 116633 | MCA100512 | | | |
| 40 | 119211 | 116611 | 117456 | MCA100513 | | | |
| 40 | 119211 | 117460 | 118032 | MCA100514 | | | |
| 40 | 119211 | 22301 | 24235 | MCA100948 | g1574757 | e-143 | ABC transporter, ATP-binding protein |
| 40 | 119211 | 21230 | 22201 | MCA100949 | g1872207 | 2.00E-35 | HtrB homolog |
| 40 | 119211 | 20793 | 21170 | MCA100950 | g2634659 | 4.00E-42 | aspartate 1-decarboxylase |
| 40 | 119211 | 17870 | 18673 | MCA100952 | g1052830 | 6.00E-63 | indoleglycerol phosphate synthetase |
| 40 | 119211 | 16782 | 17798 | MCA100953 | g143784 | 3.00E-42 | tryptophanyl tRNA synthetase (EC 6.1.1.2) |
| 40 | 119211 | 15955 | 16656 | MCA100954 | g410131 | 8.00E-22 | ORFX7 |
| 40 | 119211 | 15289 | 15762 | MCA100955 | g410132 | 3.00E-14 | ORFX8 |
| 40 | 119211 | 14182 | 15102 | MCA100956 | g1574128 | 5.00E-73 | conserved hypothetical protein |
| 40 | 119211 | 77032 | 77787 | MCA101016 | g1573017 | 1.00E-50 | tRNA delta(2)-isopentenylpyrophosphate transferase |
| 40 | 119211 | 78161 | 78421 | MCA101017 | g1065627 | 3.00E-30 | yersinia multiple regulator |
| 40 | 119211 | 78982 | 79953 | MCA101019 | g1789588 | 4.00E-68 | putative isomerase |
| 40 | 119211 | 80020 | 80511 | MCA101020 | g2367202 | 6.00E-33 | orf, hypothetical protein |
| 40 | 119211 | 80545 | 81120 | MCA101021 | | | |
| 40 | 119211 | 81173 | 81667 | MCA101023 | g606139 | 6.00E-15 | ORF_o185 |
| 40 | 119211 | 81698 | 82408 | MCA101024 | g2317737 | 3.00E-87 | putative ABC transporter ATP-binding protein |

TABLE 1-continued

| Contig | Size | Start | End | Locus ID | Identifier | P-value | Description |
|---|---|---|---|---|---|---|---|
| 40 | 119211 | 82528 | 86061 | MCA101025 | g2766693 | 0 | proline dehydrogenase |
| 40 | 119211 | 88029 | 89999 | MCA101028 | g1161059 | 3.00E-57 | protease |
| 40 | 119211 | 90522 | 92645 | MCA101031 | | | |
| 40 | 119211 | 60578 | 62242 | MCA101150 | g1574163 | e-112 | dihydrolipoamide acetyltransferase (aceF) |
| 40 | 119211 | 48773 | 50050 | MCA101214 | g154288 | e-142 | 5-phosphoribosylglycin-amide synthetase |
| 40 | 119211 | 47317 | 48624 | MCA101215 | g3087737 | 9.00E-44 | ABC1 protein |
| 40 | 119211 | 44031 | 44555 | MCA101218 | g1573090 | 1.00E-48 | DNA polymerase III, epsilon subunit (dnaQ) |
| 40 | 119211 | 43024 | 43593 | MCA101220 | g396335 | 3.00E-37 | No definition line found |
| 40 | 119211 | 42522 | 42941 | MCA101221 | g1742695 | 3.00E-34 | Ferredoxin II. |
| 40 | 119211 | 40605 | 40901 | MCA101223 | g1787504 | 7.00E-22 | orf, hypothetical protein |
| 40 | 119211 | 38672 | 40519 | MCA101224 | g1799717 | 7.00E-74 | similar to [SwissProt Accession Number P44246] |
| 40 | 119211 | 37107 | 37787 | MCA101226 | g3861231 | 6.00E-49 | unknown |
| 40 | 119211 | 114989 | 115282 | MCA101355 | | | |
| 40 | 119211 | 92788 | 93711 | MCA101469 | g1573776 | e-104 | cell division protein (ftsY) |
| 40 | 119211 | 93897 | 94241 | MCA101470 | g2313803 | 2.00E-27 | methylated-DNA--protein-cysteine methyltransferase |
| 40 | 119211 | 94362 | 95357 | MCA101471 | g47870 | 2.00E-94 | dihydroorotate oxidase |
| 40 | 119211 | 95392 | 95904 | MCA101472 | | | |
| 40 | 119211 | 95970 | 97439 | MCA101473 | g1788651 | e-171 | amidophosphoribosyl-transferase = PRPP amidotransferase |
| 40 | 119211 | 97996 | 98835 | MCA101475 | g1944158 | 5.00E-36 | lytic transglycosylase |
| 40 | 119211 | 99306 | 101294 | MCA101476 | g1592818 | 0 | uvrB |
| 40 | 119211 | 101328 | 101969 | MCA101477 | | | |
| 40 | 119211 | 102078 | 105977 | MCA101480 | g1574781 | 2.00E-44 | exodeoxyribonuclease V, beta chain (recB) |
| 40 | 119211 | 106602 | 108041 | MCA101482 | g3142727 | 3.00E-49 | exodeoxyribonuclease V subunit |
| 40 | 119211 | 108251 | 109219 | MCA101483 | g3885440 | 1.00E-86 | ybdG homolog |
| 40 | 119211 | 109659 | 110585 | MCA101484 | g148275 | 5.00E-16 | Exonuclease VII large subunit |
| 40 | 119211 | 111005 | 111736 | MCA101485 | g2072699 | 4.00E-74 | pvdS |
| 40 | 119211 | 118395 | 118646 | MCA101541 | | | |
| 40 | 119211 | 118082 | 118393 | MCA101543 | | | |
| 40 | 119211 | 52375 | 53448 | MCA101589 | g151446 | e-112 | P-protein |
| 40 | 119211 | 53505 | 54374 | MCA101590 | g410055 | 2.00E-43 | cyclohexadienyl dehydrogenase |
| 40 | 119211 | 54495 | 55763 | MCA101591 | g2634678 | e-101 | 5-enolpyruvoylshikimate-3-phosphate synthase |
| 40 | 119211 | 55862 | 56695 | MCA101592 | g1906367 | 4.00E-64 | hypothetical protein |
| 40 | 119211 | 56723 | 57088 | MCA101593 | g1789438 | 1.00E-10 | putative kinase |
| 40 | 119211 | 57079 | 57510 | MCA101594 | | | |
| 40 | 119211 | 57818 | 60442 | MCA101595 | g2564217 | 0 | pyruvate dehydrogenase (lipoamide) |
| 40 | 119211 | 62595 | 63365 | MCA101597 | g1789363 | 4.00E-78 | orf, hypothetical protein |
| 40 | 119211 | 67710 | 68651 | MCA101599 | g1788765 | 7.00E-77 | thiosulfate binding protein |
| 40 | 119211 | 69040 | 70197 | MCA101600 | g3978474 | e-115 | MetZ homolog |
| 40 | 119211 | 70448 | 71575 | MCA101601 | g1574510 | e-157 | ribonucleoside diphosphate reductase, beta chain (nrdB) |
| 40 | 119211 | 71681 | 71902 | MCA1G1602 | g1788568 | 2.00E-08 | orf, hypothetical protein |
| 40 | 119211 | 73244 | 74389 | MCA101604 | g498170 | 3.00E-87 | carboxynorspermidine decarboxylase |
| 40 | 119211 | 74602 | 75804 | MCA101605 | g1001125 | 3.00E-74 | hypothetical protein |
| 40 | 119211 | 75957 | 76511 | MCA101606 | g4155434 | 7.00E-36 | putative |
| 40 | 119211 | 112492 | 112878 | MCA101770 | | | |
| 40 | 119211 | 112942 | 113109 | MCA101771 | | | |
| 40 | 119211 | 118691 | 119050 | MCA101772 | | | |
| 40 | 119211 | 119052 | 119211 | MCA101774 | | | |
| 40 | 119211 | 18727 | 20568 | MCA101814 | g141801 | 1.00E-83 | anthranilate phosphoribosyltransferase (EC 2.4.2.18) |

TABLE 1-continued

| Contig | Size | Start | End | Locus ID | Identifier | P-value | Description |
|---|---|---|---|---|---|---|---|
| 40 | 119211 | 11382 | 13633 | MCA101815 | g1799581 | 0 | ribonucleoside-diphosphate reductase 1 alpha (EC1.17.4.1) |
| 40 | 119211 | 63531 | 66164 | MCA101886 | g1573962 | 2.00E-39 | exodeoxyribonuclease V, gamma chain (recC) |
| 40 | 119211 | 44757 | 45182 | MCA101959 | g1552784 | 1.00E-34 | ribonuclease H |
| 40 | 119211 | 45397 | 45936 | MCA101960 | g3861372 | 2.00E-09 | possible protoporphyrinogen oxidase (hemk) |
| 40 | 119211 | 46032 | 47180 | MCA101961 | g2293312 | 3.00E-21 | YtfP |
| 40 | 119211 | 24876 | 26252 | MCA101962 | g598251 | 0 | outer membrane protein E |
| 40 | 119211 | 29114 | 29992 | MCA101964 | g2983572 | 5.00E-19 | 3-oxoacyl-[acyl-carrier-protein] synthase III |
| 40 | 119211 | 31377 | 32036 | MCA101965 | g580875 | 3.00E-59 | ipa-57d |
| 40 | 119211 | 32139 | 32588 | MCA101967 | g1788911 | 3.00E-35 | putative deaminase |
| 40 | 119211 | 32677 | 33342 | MCA101968 | g1574149 | 2.00E-50 | cytidylate kinase 1 (cmkA) |
| 40 | 119211 | 33597 | 35186 | MCA101969 | g1651439 | 0 | 30S ribosomal protein S1. |
| 40 | 119211 | 35506 | 35781 | MCA101970 | g399670 | 2.00E-16 | integration host factor beta subunit |
| 40 | 119211 | 36355 | 37032 | MCA101971 | g805068 | 6.00E-56 | OMP decarboxylase |
| 40 | 119211 | 37969 | 38598 | MCA101972 | g2635898 | 2.00E-17 | similar to hypothetical proteins |
| 40 | 119211 | 86419 | 87177 | MCA102059 | | | |
| 40 | 119211 | 3811 | 4308 | MCA102109 | g1001123 | 6.00E-08 | hypothetical protein |
| 40 | 119211 | 24430 | 24660 | MCA102111 | | | |
| 40 | 119211 | 35812 | 36213 | MCA102116 | | | |
| 40 | 119211 | 30377 | 31330 | MCA102117 | | | |
| 41 | 269223 | 188318 | 189049 | MCA10C014 | g2181957 | 5.00E-43 | hypothetical protein Rv3300c |
| 41 | 269223 | 77773 | 79113 | MCA100035 | g149757 | 0 | outer membrane protein CD |
| 41 | 269223 | 255725 | 256996 | MCA100036 | g882710 | e-118 | N-acetylglutamate synthase |
| 41 | 269223 | 1764 | 2576 | MCA100054 | g1573276 | 2.00E-46 | pyrroline-5-carboxylate reductase (proC) |
| 41 | 269223 | 195583 | 196011 | MCA100074 | g1001829 | 4.00E-15 | hypothetical protein |
| 41 | 269223 | 82057 | 82719 | MCA100076 | g987642 | 5.00E-49 | ribonuclease III |
| 41 | 269223 | 79399 | 80121 | MCA100078 | g1788917 | 1.00E-61 | pyridoxine biosynthesis |
| 41 | 269223 | 127128 | 128444 | MCA100098 | g407186 | 3.00E-75 | DnaA protein |
| 41 | 269223 | 192138 | 192839 | MCA100103 | g2108342 | 1.00E-89 | OmpR protein |
| 41 | 269223 | 191142 | 192041 | MCA100104 | g1788499 | 6.00E-42 | orf, hypothetical protein |
| 41 | 269223 | 126337 | 126468 | MCA100112 | g147682 | 7.00E-16 | ribosomal protein L34 |
| 41 | 269223 | 125896 | 126168 | MCA100113 | g581462 | 2.00E-13 | homologous to E. coli rnpA |
| 41 | 269223 | 125582 | 125788 | MCA100114 | g2898108 | 2.00E-15 | 9–10 kDa protein-like |
| 41 | 269223 | 193168 | 195417 | MCA100121 | g1098475 | e-171 | region E; orf; homologous to E. coli o622, U18997 |
| 41 | 269223 | 254370 | 255644 | MCA100131 | g1574371 | e-100 | glutamate permease (gltS) |
| 41 | 269223 | 4189 | 4955 | MCA100190 | g147322 | 2.00E-77 | acetyl-CoA carboxylase |
| 41 | 269223 | 41968 | 43620 | MCA100198 | g2367384 | 0 | putative ATP-binding component of a transport system |
| 41 | 269223 | 40805 | 41419 | MCA100200 | g2231726 | 2.00E-41 | macrophage infectivity potentiator |
| 41 | 269223 | 189796 | 190944 | MCA100247 | g1789473 | e-107 | putative transport protein |
| 41 | 269223 | 185949 | 186641 | MCA100307 | g1574175 | 3.00E-48 | 16s pseudouridylate 516 synthase (rsuA) |
| 41 | 269223 | 184967 | 185572 | MCA100308 | g3135321 | 5.00E-12 | putative thiol:disulfide interchange protein precursor |
| 41 | 269223 | 183536 | 184672 | MCA100309 | g1389759 | 2.00E-94 | DnaJ |
| 41 | 269223 | 37916 | 38281 | MCA100355 | g3323226 | 2.00E-21 | T. pallidum predicted coding region TP0895 |
| 41 | 269223 | 227863 | 230013 | MCA100365 | g391839 | 0 | alpha-subunit of HDT |
| 41 | 269223 | 230052 | 231215 | MCA100366 | g391840 | e-146 | beta-subunit of HDT |

TABLE 1-continued

| Contig | Size | Start | End | Locus ID | Identifier | P-value | Description |
|---|---|---|---|---|---|---|---|
| 41 | 269223 | 36803 | 37561 | MCA100439 | g1468939 | 7.00E-60 | meso-2,3-butanediol dehydrogenase (D-acetoin forming) |
| 41 | 269223 | 34942 | 36237 | MCA100441 | g1657503 | e-106 | similar to *S. aureus* mercury(II) reductase |
| 41 | 269223 | 33813 | 34805 | MCA100442 | g1001812 | 4.00E-72 | hypothetical protein |
| 41 | 269223 | 32952 | 33533 | MCA100443 | g1789819 | 2.00E-49 | orf, hypothetical protein |
| 41 | 269223 | 164675 | 165019 | MCA100454 | g2635307 | 3.00E-08 | ysmA |
| 41 | 269223 | 94670 | 95482 | MCA100483 | g1573330 | e-120 | iron (chelated) ABC transporter, periplasmic-binding prot |
| 41 | 269223 | 95485 | 96356 | MCA100484 | g1573329 | e-115 | iron (chelated) ABC transporter, ATP-binding prot (yfeB) |
| 41 | 269223 | 96387 | 97214 | MCA100485 | g1573328 | e-100 | iron (chelated) ABC transporter, permease prot (yfeC) |
| 41 | 269223 | 97272 | 98081 | MCA100486 | g1245467 | 1.00E-87 | YfeD |
| 41 | 269223 | 231781 | 232396 | MCA100534 | g2340007 | 1.00E-28 | YlbK protein |
| 41 | 269223 | 233066 | 233581 | MCA100536 | g2342534 | 8.00E-45 | PAPS reductase |
| 41 | 269223 | 233689 | 234591 | MCA100537 | g1322409 | 9.00E-89 | cysD |
| 41 | 269223 | 234772 | 236025 | MCA100538 | g1322410 | e-100 | cysN |
| 41 | 269223 | 236187 | 238250 | MCA100539 | g2367254 | 0 | DNA helicase |
| 41 | 269223 | 66114 | 68632 | MCA100556 | g1574437 | e-153 | cell division protein FtsK-related protein |
| 41 | 269223 | 69114 | 69851 | MCA100558 | g2668599 | 2.00E-78 | ATPase |
| 41 | 269223 | 70011 | 70676 | MCA100559 | g1787088 | 8.00E-34 | arginine 3rd transport system periplasmic binding prot |
| 41 | 269223 | 70868 | 71533 | MCA100560 | g769794 | 2.00E-40 | artJ |
| 41 | 269223 | 75715 | 77502 | MCA100597 | g1790302 | 0 | putative GTP-binding factor |
| 41 | 269223 | 74090 | 75439 | MCA100598 | g1573640 | e-127 | UDP-N-acetylglucosamine pyrophosphorylase (glmU) |
| 41 | 269223 | 73356 | 74006 | MCA100599 | g496542 | 1.00E-48 | OccM |
| 41 | 269223 | 71723 | 73317 | MCA100600 | g1787085 | 1.00E-36 | arginine 3rd transport system periplasmic binding prot |
| 41 | 269223 | 2850 | 4010 | MCA100637 | g971394 | 6.00E-27 | similar to Acc. No. D26185 |
| 41 | 269223 | 176444 | 178372 | MCA100657 | g606286 | e-158 | ORF_o637 |
| 41 | 269223 | 179340 | 180227 | MCA100659 | g1789752 | 5.00E-45 | orf, hypothetical protein |
| 41 | 269223 | 180371 | 181150 | MCA100660 | g1185002 | 2.00E-47 | dihydrodipicolinate reductase |
| 41 | 269223 | 181240 | 182331 | MCA100661 | g304266 | 1.00E-45 | cystathionine beta-lyase |
| 41 | 269223 | 182445 | 183365 | MCA100662 | g2634328 | 3.00E-89 | similar to sodium-dependent transporter |
| 41 | 269223 | 178416 | 179237 | MCA100692 | g2293347 | 2.00E-12 | DnaJ |
| 41 | 269223 | 39931 | 40560 | MCA100773 | g451652 | 1.00E-45 | unknown |
| 41 | 269223 | 244876 | 245628 | MCA101070 | g4186118 | 2.00E-24 | type 4 prepilin peptidase |
| 41 | 269223 | 303 | 1001 | MCA101092 | g4155349 | 1.00E-27 | phosphomethylpyrimidine kinase |
| 41 | 269223 | 129669 | 130736 | MCA101112 | g150880 | 2.00E-37 | putative |
| 41 | 269223 | 82887 | 83588 | MCA101125 | g1788921 | 8.00E-43 | leader peptidase (signal peptidase I) |
| 41 | 269223 | 111855 | 112940 | MCA101128 | g150708 | 1.00E-99 | [ribB] gene products |
| 41 | 269223 | 268513 | 268884 | MCA101181 | g1224005 | 7.00E-40 | ORF2; sim. to N-terminal phosphoribosyl c-AMP hydrolase |
| 41 | 269223 | 268096 | 268443 | MCA101182 | g1224006 | 6.00E-28 | ORF3; sim. to C-terminal phosphoribosyl c-AMP hydrolase |
| 41 | 269223 | 267596 | 268026 | MCA101183 | g1224007 | 2.00E-18 | ORF4 |
| 41 | 269223 | 266565 | 267230 | MCA101184 | g1224008 | 3.00E-59 | ORF5; mutations in this gene affect the culture pH |
| 41 | 269223 | 264696 | 266135 | MCA101185 | g2577963 | 5.00E-86 | YerD protein |

TABLE 1-continued

| Contig | Size | Start | End | Locus ID | Identifier | P-value | Description |
|---|---|---|---|---|---|---|---|
| 41 | 269223 | 263394 | 264128 | MCA101187 | g149205 | 6.00E-36 | histidine utilization repressor C (hutC) |
| 41 | 269223 | 260788 | 261690 | MCA101189 | g1573236 | 8.00E-61 | conserved hypothetical protein |
| 41 | 269223 | 259547 | 260607 | MCA101190 | g413953 | 1.00E-87 | ipa-29d |
| 41 | 269223 | 258434 | 259207 | MCA101191 | g413952 | 4.00E-45 | ipa-28d |
| 41 | 269223 | 44402 | 44662 | MCA101279 | | | |
| 41 | 269223 | 45635 | 47095 | MCA101281 | g1498192 | 8.00E-54 | putative |
| 41 | 269223 | 52663 | 52923 | MCA101283 | g1652924 | 3.00E-10 | pterin-4a-carbinolamine dehydratase |
| 41 | 269223 | 53084 | 55264 | MCA101284 | g4176379 | 0 | topoisomerase IV subunit |
| 41 | 269223 | 59095 | 59403 | MCA101288 | | | |
| 41 | 269223 | 59601 | 62384 | MCA101289 | g1573871 | 0 | DNA polymerase I (polA) |
| 41 | 269223 | 196489 | 197751 | MCA101331 | g141770 | 0 | citrate synthase precursor |
| 41 | 269223 | 250144 | 254073 | MCA101372 | g1788909 | 0 | phosphoribosylformyl-glycine amide synthetase |
| 41 | 269223 | 248757 | 249935 | MCA101373 | g2632881 | 1.00E-41 | similar to bicyclomycin resistance protein |
| 41 | 269223 | 246950 | 248584 | MCA101374 | g3220230 | e-135 | type IV pilus assembly protein TapB |
| 41 | 269223 | 245649 | 246836 | MCA101375 | g3025702 | 1.00E-56 | pilus assembly protein PilC |
| 41 | 269223 | 244092 | 244709 | MCA101377 | g1573909 | 1.00E-33 | conserved hypothetical protein |
| 41 | 269223 | 240255 | 243272 | MCA101379 | g1736781 | e-111 | Acriflavin resistance protein D. |
| 41 | 269223 | 239100 | 239612 | MCA101381 | g550460 | 4.00E-18 | membrane fusion protein |
| 41 | 269223 | 128505 | 129656 | MCA101382 | g45691 | 7.00E-61 | dnaN protein (AA 1-367) |
| 41 | 269223 | 131062 | 133455 | MCA101384 | g41646 | 0 | gyrase B (AA 1-804) |
| 41 | 269223 | 133644 | 135200 | MCA101385 | g1573186 | 0 | GMP synthase (guaA) |
| 41 | 269223 | 136888 | 137169 | MCA101388 | g1001663 | 2.00E-16 | rare lipoprotein A |
| 41 | 269223 | 137351 | 137692 | MCA101389 | g1652134 | 2.00E-23 | FKBP-type peptidyl-prolyl cis-trans isomerase |
| 41 | 269223 | 137915 | 139009 | MCA101390 | g2983314 | 3.00E-63 | ornithine decarboxylase |
| 41 | 269223 | 139063 | 140330 | MCA101391 | g1789996 | 4.00E-99 | alanine-alpha-ketoisovalerate transaminase C |
| 41 | 269223 | 140389 | 140727 | MCA101392 | g2407234 | 8.00E-26 | similar to *H. influenzae* U32836 |
| 41 | 269223 | 140754 | 141998 | MCA101393 | g1787438 | e-138 | D-amino acid dehydrogenase subunit |
| 41 | 269223 | 142379 | 144201 | MCA101394 | g1790427 | 0 | thiamin biosynthesis, pyrimidine moiety |
| 41 | 269223 | 144333 | 146159 | MCA101395 | g1574084 | 0 | ABC transporter, ATP-binding protein |
| 41 | 269223 | 146383 | 147726 | MCA101396 | g2635428 | e-130 | argininosuccinate lyase |
| 41 | 269223 | 147971 | 148915 | MCA101397 | g41666 | e-100 | porphobilinogen deaminase (AA 1 - 313) |
| 41 | 269223 | 149877 | 150605 | MCA101399 | g1573875 | 4.00E-46 | conserved hypothetical protein |
| 41 | 269223 | 38460 | 38705 | MCA101530 | g42543 | 1.00E-13 | pspE protein |
| 41 | 269223 | 31815 | 32798 | MCA101546 | g1001340 | 4.00E-54 | hypothetical protein |
| 41 | 269223 | 28035 | 30956 | MCA101548 | g4377308 | e-118 | Zinc Metalloprotease (insulinase family) |
| 41 | 269223 | 26681 | 27871 | MCA101549 | g2367234 | e-107 | orf. hypothetical protein |
| 41 | 269223 | 25873 | 26463 | MCA101550 | g1573078 | 1.00E-36 | phosphatidylglycero-phosphate synthase (pgsA) |
| 41 | 269223 | 23781 | 24791 | MCA101552 | g1657863 | 0 | NAD repressor/NMN transporter NadRp |
| 41 | 269223 | 23259 | 23432 | MCA101553 | g2636024 | 5.00E-09 | yvlC |
| 41 | 269223 | 19781 | 22992 | MCA101554 | g1657862 | 0 | glycyl-tRNA synthetase alpha subunit |
| 41 | 269223 | 18833 | 19485 | MCA101555 | g1787111 | 1.00E-42 | leucyl, phenylalanyl-tRNA-protein transferase |

TABLE 1-continued

| Contig | Size | Start | End | Locus ID | Identifier | P-value | Description |
|---|---|---|---|---|---|---|---|
| 41 | 269223 | 17415 | 18665 | MCA101556 | g3284000 | 0 | serine hydroxymethyltransferase |
| 41 | 269223 | 16824 | 17255 | MCA101557 | g43231 | 1.00E-10 | chorismate-pyruvate lyase |
| 41 | 269223 | 14797 | 16386 | MCA101558 | g2662054 | e-171 | isocitrate lyase |
| 41 | 269223 | 12474 | 14624 | MCA101559 | g1906369 | 0 | hypothetical protein |
| 41 | 269223 | 8656 | 11007 | MCA101561 | g1651530 | e-160 | Ribonuclease e (EC 3.1.4.—) (RNase E). |
| 41 | 269223 | 6766 | 7716 | MCA101563 | g1573385 | 5.00E-64 | conserved hypothetical protein |
| 41 | 269223 | 5116 | 6546 | MCA101564 | g4200042 | e-112 | exopolyphosphatase |
| 41 | 269223 | 91641 | 91808 | MCA101609 | g208931 | 1.00E-16 | ORF16-lacZ fusion protein |
| 41 | 269223 | 88129 | 88366 | MCA101611 | g1334480 | 4.00E-14 | unique orf |
| 41 | 269223 | 86216 | 86662 | MCA101614 | g1573906 | 3.00E-65 | H. influenzae predicted coding region HI0882 |
| 41 | 269223 | 83997 | 85778 | MCA101615 | g1572960 | 0 | GTP-binding membrane protein (lepA) |
| 41 | 269223 | 80995 | 81894 | MCA101618 | g1572957 | 1.00E-80 | GTP-binding protein (era) |
| 41 | 269223 | 175707 | 176225 | MCA101619 | g560723 | 5.00E-22 | Mip = 24 kda macrophage infectivity potentiator protein |
| 41 | 269223 | 174030 | 174176 | MCA101621 | g1894774 | 5.00E-16 | rubredoxin |
| 41 | 269223 | 172917 | 173972 | MCA101622 | g1789065 | 1.00E-42 | putative oxidoreductase |
| 41 | 269223 | 171413 | 172576 | MCA101623 | g2150108 | 2.00E-85 | periplasmic substrate binding protein |
| 41 | 269223 | 170503 | 171255 | MCA101624 | g2150109 | 5.00E-61 | integral membrane protein |
| 41 | 269223 | 169728 | 170423 | MCA101625 | g48972 | 2.00E-64 | nitrate transporter |
| 41 | 269223 | 169168 | 169497 | MCA101626 | g1574579 | 3.00E-30 | conserved hypothetical protein |
| 41 | 269223 | 167480 | 168979 | MCA101627 | g3005690 | 7.00E-91 | gamma-glutamylcysteine synthetase |
| 41 | 269223 | 165388 | 166755 | MCA101629 | g1573076 | e-121 | conserved hypothetical protein |
| 41 | 269223 | 164248 | 164496 | MCA101631 | g1573769 | 9.00E-08 | conserved hypothetical protein |
| 41 | 269223 | 153230 | 153748 | MCA101633 | g1573022 | 8.00E-20 | heat shock protein (grpE) |
| 41 | 269223 | 151115 | 153019 | MCA101634 | g2522264 | 0 | DnaK |
| 41 | 269223 | 198632 | 198931 | MCA101637 | g2239247 | 1.00E-18 | SdhC protein |
| 41 | 269223 | 198958 | 199290 | MCA101638 | g42924 | 5.00E-19 | succinate dehydrogenase hydrophobic subunit |
| 41 | 269223 | 199379 | 201199 | MCA101639 | g3273345 | 0 | fumarate reductase flavoprotein subunit |
| 41 | 269223 | 201300 | 201977 | MCA101640 | g2239250 | 1.00E-96 | succinate dehydrogenase putative iron sulphur subunit |
| 41 | 269223 | 202407 | 205205 | MCA101641 | g39232 | 0 | 2-oxoglutarate dehydrogenase |
| 41 | 269223 | 205326 | 206555 | MCA101642 | g39283 | e-131 | succinyltransferase |
| 41 | 269223 | 206648 | 208090 | MCA101643 | g151345 | e-155 | dihydrolipoamide dehydrogenase |
| 41 | 269223 | 212826 | 214043 | MCA101645 | | | |
| 41 | 269223 | 214142 | 215374 | MCA101646 | | | |
| 41 | 269223 | 216050 | 218155 | MCA101648 | g148698 | 3.00E-92 | prolyl endopeptidase |
| 41 | 269223 | 218735 | 220828 | MCA101650 | g1573174 | e-147 | oligopeptidase A (prlC) |
| 41 | 269223 | 221075 | 221800 | MCA101651 | g1787008 | 8.00E-40 | orf, hypothetical protein |
| 41 | 269223 | 221952 | 222545 | MCA101652 | g882483 | 3.00E-50 | ORF__o197 |
| 41 | 269223 | 222757 | 224055 | MCA101653 | g1773120 | e-105 | trigger factor |
| 41 | 269223 | 224295 | 224885 | MCA101654 | g1773121 | 1.00E-84 | ATP-dependent Clp proteinase |
| 41 | 269223 | 224934 | 226208 | MCA101655 | g1573717 | e-149 | ATP-dependent Clp protease, ATP-binding subunit |

TABLE 1-continued

| Contig | Size | Start | End | Locus ID | Identifier | P-value | Description |
|---|---|---|---|---|---|---|---|
| 41 | 269223 | 123662 | 125293 | MCA101656 | g45709 | e-133 | homologous to *E. coli* 60 K |
| 41 | 269223 | 122095 | 123465 | MCA101657 | g45710 | e-113 | homologous to *E. coli* 50 K |
| 41 | 269223 | 121548 | 121988 | MCA101658 | g42148 | 1.00E-46 | orf1 |
| 41 | 269223 | 120490 | 121497 | MCA101659 | g581147 | 4.00E-80 | orf2, homologue to *B. subtilis* ribG |
| 41 | 269223 | 119545 | 120186 | MCA101660 | g150707 | 3.00E-49 | riboflavin synthetase alpha subunit |
| 41 | 269223 | 118437 | 119363 | MCA101661 | g3328155 | 4.00E-69 | methionyl-tRNA formyltransferase |
| 41 | 269223 | 117032 | 118369 | MCA101662 | g1573620 | 7.00E-65 | sun protein (sun) |
| 41 | 269223 | 115305 | 116708 | MCA101663 | g2160269 | e-153 | threonine synthase |
| 41 | 269223 | 114048 | 115172 | MCA101664 | g1574014 | 2.00E-44 | DNA processing chain A (dprA) |
| 41 | 269223 | 113447 | 114028 | MCA101665 | g2367210 | 1.00E-19 | orf, hypothetical protein |
| 41 | 269223 | 110508 | 111677 | MCA101668 | g1460081 | 3.00E-85 | hypothetical protein Rv2559c |
| 41 | 269223 | 109304 | 109822 | MCA101670 | g402362 | 3.00E-15 | hypothetical protein |
| 41 | 269223 | 105340 | 106233 | MCA101673 | g1354827 | 3.00E-67 | arginase |
| 41 | 269223 | 104054 | 105262 | MCA101674 | g790956 | e-145 | ornithine aminotransferase |
| 41 | 269223 | 103248 | 103808 | MCA101675 | g1628369 | 2.00E-10 | gepB |
| 41 | 269223 | 101499 | 102242 | MCA101677 | g4154851 | 3.00E-72 | putative |
| 41 | 269223 | 100074 | 101222 | MCA101678 | g1573761 | 2.00E-75 | conserved hypothetical protein |
| 41 | 269223 | 98638 | 99816 | MCA101679 | g1574452 | e-120 | tyrosyl tRNA synthetase (tyrs) |
| 41 | 269223 | 44008 | 44328 | MCA101794 | | | |
| 41 | 269223 | 257352 | 257930 | MCA101931 | | | |
| 41 | 269223 | 238243 | 238896 | MCA101934 | | | |
| 41 | 269223 | 239645 | 239932 | MCA101937 | | | |
| 41 | 269223 | 243516 | 244079 | MCA101943 | | | |
| 41 | 269223 | 44993 | 45466 | MCA101954 | | | |
| 41 | 269223 | 186833 | 187384 | MCA101958 | g42358 | 5.00E-21 | pepQ product, proline dipeptidase |
| 41 | 269223 | 187980 | 188180 | MCA101973 | g3322357 | 1.00E-08 | dnaK suppressor, putative |
| 41 | 269223 | 211262 | 211762 | MCA101976 | g529727 | 7.00E-09 | heme receptor |
| 41 | 269223 | 55427 | 56215 | MCA101978 | g1788125 | 8.00E-47 | putative enzyme |
| 41 | 269223 | 56337 | 57158 | MCA101979 | g4155762 | 3.00E-16 | putative |
| 41 | 269223 | 57227 | 58789 | MCA101980 | g1574592 | 0 | peptide chain release factor 3 (prfC) |
| 41 | 269223 | 62725 | 65282 | MCA101981 | g1574197 | 0 | DNA topoisomerase I (topA) |
| 41 | 269223 | 106832 | 107182 | MCA102132 | | | |
| 41 | 269223 | 113110 | 113376 | MCA102133 | g1788096 | 5.00E-11 | orf, hypothetical protein |
| 41 | 269223 | 24857 | 25618 | MCA102137 | g1651338 | 7.00E-08 | PnuC protein |

TABLE 1-continued

| Contig | Size | Start | End | Locus ID | Identifier | P-value | Description |
|---|---|---|---|---|---|---|---|
| 41 | 269223 | 31241 | 31690 | MCA102138 | | | |
| 41 | 269223 | 135356 | 136573 | MCA102139 | | | |
| 41 | 269223 | 262656 | 262982 | MCA102143 | | | |
| 41 | 269223 | 148933 | 149691 | MCA102146 | g496215 | 5.00E-12 | uropprphyrinogen-III-synthase |
| 41 | 269223 | 155575 | 156525 | MCA102147 | | | |
| 41 | 269223 | 156368 | 159940 | MCA102148 | | | |
| 41 | 269223 | 160109 | 161479 | MCA102149 | | | |
| 41 | 269223 | 161476 | 162411 | MCA102150 | | | |
| 41 | 269223 | 162428 | 163453 | MCA102151 | | | |
| 41 | 269223 | 163450 | 164040 | MCA102152 | | | |

TABLE 2

| Locus ID | End | Locus ID | End | Locus ID | End | Locus ID | End |
|---|---|---|---|---|---|---|---|
| MCA1c0001 | 5' | MCA1c0005 | 5' | MCA1c0022 | 5' | ND | ND |
| MCA1c0001 | 3' | ND | ND | MCA1c0022 | 3' | ND | ND |
| MCA1c0002 | 5' | ND | ND | MCA1c0023 | 5' | ND | ND |
| MCA1c0002 | 3' | MCA1c0039 | 3' | MCA1c0023 | 3' | ND | ND |
| MCA1c0003 | 5' | ND | ND | MCA1c0024 | 5' | ND | ND |
| MCA1c0003 | 3' | ND | ND | MCA1c0024 | 3' | ND | ND |
| MCA1c0004 | 5' | ND | ND | MCA1c0025 | 5' | ND | ND |
| MCA1c0004 | 3' | MCA1c0009 | 5' | MCA1c0025 | 3' | ND | ND |
| MCA1c0005 | 5' | MCA1c0001 | 5' | MCA1c0026 | 5' | MCA1c0015 | 3' |
| MCA1c0005 | 3' | ND | ND | MCA1c0026 | 3' | ND | ND |
| MCA1c0006 | 5' | ND | ND | MCA1c0027 | 5' | ND | ND |
| MCA1c0006 | 3' | MCA1c0033 | 5' | MCA1c0027 | 3' | ND | ND |
| MCA1c0007 | 5' | ND | ND | MCA1c0028 | 5' | MCA1c0029 | 3' |
| MCA1c0007 | 3' | ND | ND | MCA1c0028 | 3' | ND | ND |
| MCA1c0008 | 5' | ND | ND | MCA1c0029 | 5' | ND | ND |
| MCA1c0008 | 3' | MCA1c0012 | 3' | MCA1c0029 | 3' | MCA1c0028 | 5' |
| MCA1c0009 | 5' | MCA1c0004 | 3' | MCA1c0030 | 5' | MCA1c0009 | 3' |
| MCA1c0009 | 3' | MCA1c0030 | 5' | MCA1c0030 | 3' | ND | ND |
| MCA1c0010 | 5' | ND | ND | MCA1c0031 | 5' | ND | ND |
| MCA1c0010 | 3' | ND | ND | MCA1c0031 | 3' | ND | ND |
| MCA1c0011 | 5' | ND | ND | MCA1c0032 | 5' | ND | ND |
| MCA1c0011 | 3' | ND | ND | MCA1c0032 | 3' | ND | ND |
| MCA1c0012 | 5' | ND | | MCA1c0033 | 5' | MCA1c0006 | 3' |
| MCA1c0012 | 3' | MCA1c0008 | 3' | MCA1c0033 | 3' | ND | ND |
| MCA1c0013 | 5' | ND | | MCA1c0034 | 5' | MCA1c0036 | 3' |
| MCA1c0013 | 3' | ND | | MCA1c0034 | 3' | ND | ND |
| MCA1c0014 | 5' | ND | | MCA1c0035 | 5' | ND | ND |
| MCA1c0014 | 3' | ND | | MCA1c0035 | 3' | ND | ND |
| MCA1c0015 | 5' | ND | | MCA1c0036 | 5' | ND | ND |
| MCA1c0015 | 3' | MCA1c0026 | 5' | MCA1c0036 | 3' | MCA1c0034 | 5' |
| MCA1c0016 | 5' | MCA1c0019 | 3' | MCA1c0037 | 5' | ND | ND |
| MCA1c0016 | 3' | ND | | MCA1c0037 | 3' | ND | ND |
| MCA1c0017 | 5' | ND | | MCA1c0038 | 5' | ND | ND |
| MCA1c0017 | 3' | ND | | MCA1c0038 | 3' | MCA1c0018 | 5' |
| MCA1c0018 | 5' | MCA1c0038 | 3' | MCA1c0039 | 5' | ND | ND |
| MCA1c0018 | 3' | MCA1c0021 | 3' | MCA1c0039 | 3' | MCA1c0002 | 3' |
| MCA1c0019 | 5' | ND | | MCA1c0040 | 5' | ND | ND |
| MCA1c0019 | 3' | MCA1c0016 | 5' | MCA1c0040 | 3' | ND | ND |
| MCA1c0020 | 5' | ND | | MCA1c0041 | 5' | ND | ND |
| MCA1c0020 | 3' | ND | | MCA1c0041 | 3' | ND | ND |
| MCA1c0021 | 5' | ND | ND | | | | |
| MCA1c0021 | 3' | MCA1c0018 | 3' | | | | |

SEQUENCE LISTING

The patent contains a lengthy "Sequence Listing" section. A copy of the "Sequence Listing" is available in electronic form from the USPTO web site (http://seqdata.uspto.gov/sequence.html?DocID=6632636B1). An electronic copy of the "Sequence Listing" will also be available from the USPTO upon request and payment of the fee set forth in 37 CFR 1.19(b)(3).

What is claimed is:

1. A purified or isolated nucleic acid consisting essentially of a nucleotide sequence that encodes the same 3-ketoacyl-ACP-reductase encoded by nucleotides 31291 to 31908 of SEQ ID NO:13 or a nucleotide sequence fully complementary thereto.

2. A recombinant construct comprising a nucleotide sequence that encodes the same 3-ketoacyl-ACP-reductase encoded by nucleotides 31291 to 31908 of SEQ ID NO:13, or a nucleotide sequence fully complementary thereto, operably linked to a promoter.

3. A method of making 3-ketoacyl-ACP-reductase of *Moraxella catarrahalis* comprising:

obtaining a nucleic acid consisting essentially of a nucleotide sequence that encodes the same 3-ketoacyl-ACP-reductase encoded by nucleotides 31291 to 31908 of SEQ ID NO:13;

inserting said nucleic acid in an expression vector such that said nucleic acid is operably linked to a promoter; and introducing said expression vector into a host cell whereby said host cell produces the protein encoded by said nucleic acid.

4. The method of claim 3, further comprising isolating the protein.

5. The method of claim 3, wherein said nucleic acid sequence consists essentially of nucleotides 31291 to 31908 of SEQ ID NO:13 or a nucleotide sequence fully complementary thereto.

6. A method for constructing a host cell that expresses 3-ketoacyl-ACP-reductase of Moraxella catarrahalis comprising introducing a recombinant construct comprising a promoter operably linked to a nucleic acid comprising a nucleotide sequence that encodes the same 3-ketoacyl-ACP-reductase encoded by nucleotides 31291 to 31908 of SEQ ID NO:13 into said cell.

7. The method of claim 6, wherein said nucleic acid sequence consists essentially of nucleotides 31291 to 31908 of SEQ ID NO:13 or a nucleotide sequence fully complementary thereto.

8. The purified or isolated nucleic acid of claim 1 wherein said nucleic acid sequence consists essentially of nucleotides 31291 to 31908 of SEQ ID NO:13 or a nucleotide sequence fully complementary thereto.

9. An isolated expression construct comprising nucleotides 31291 to 31908 of SEQ ID NO:13 which encodes 3-ketoacvl-ACP-reductase, or a nucleotide sequence fully complementary thereto, operably linked to a promoter.

10. A vector comprising the purified or isolated nucleic acid of any one of claims 1 or 8.

11. The vector of claim 10, wherein the isolated nucleic acid is operably linked to a promoter.

12. The vector of claim 11, wherein the vector is an expression vector.

13. A cultured cell line comprising the vector of claim 10.

14. A purified or isolated oligonucleotide consisting essentially of a fragment of a nucleic acid having the nucleotide sequence of nucleotides 31291 to 31908 of SEQ ID NO:13 or a sequence complementary thereto, wherein said oligonucleotide is at least 22 nucleotides in length.

* * * * *